US009018158B2

(12) United States Patent
Onsoyen et al.

(10) Patent No.: US 9,018,158 B2
(45) Date of Patent: Apr. 28, 2015

(54) ALGINATE OLIGOMERS FOR USE IN OVERCOMING MULTIDRUG RESISTANCE IN BACTERIA

(75) Inventors: Edvar Onsoyen, Sandvika (NO); Rolf Myrvold, Sandvika (NO); Arne Dessen, Sandvika (NO); David Thomas, Cardiff (GB); Timothy Rutland Walsh, Cardiff (GB)

(73) Assignee: Algipharma AS, Sandvika (NO)

( * ) Notice: Subject to any disclaimer, the term of this patent is extended or adjusted under 35 U.S.C. 154(b) by 184 days.

(21) Appl. No.: 13/376,164

(22) PCT Filed: Jun. 3, 2010

(86) PCT No.: PCT/GB2010/001097
§ 371 (c)(1),
(2), (4) Date: Jan. 26, 2012

(87) PCT Pub. No.: WO2010/139957
PCT Pub. Date: Dec. 9, 2010

(65) Prior Publication Data
US 2012/0122768 A1 May 17, 2012

(30) Foreign Application Priority Data

Jun. 3, 2009 (GB) .................................. 0909557.1
Aug. 7, 2009 (GB) .................................. 0913829.8
Oct. 14, 2009 (GB) .................................. 0917995.3

(51) Int. Cl.
A01N 37/18 (2006.01)
A61K 38/04 (2006.01)
A61K 31/7048 (2006.01)
A61K 31/7052 (2006.01)
A61K 31/734 (2006.01)
A61K 45/06 (2006.01)

(52) U.S. Cl.
CPC ......... *A61K 31/7048* (2013.01); *A61K 31/7052* (2013.01); *A61K 31/734* (2013.01); *A61K 45/06* (2013.01)

(58) Field of Classification Search
None
See application file for complete search history.

(56) References Cited

U.S. PATENT DOCUMENTS

| 4,225,592 A | 9/1980 | Lakatos et al. |
| 5,166,137 A | 11/1992 | Otterlei et al. |
| 5,169,840 A | 12/1992 | Otterlei et al. |
| 5,192,362 A | 3/1993 | Harvey et al. |
| 5,683,991 A | 11/1997 | Guggenbichler et al. |
| 6,121,441 A | 9/2000 | Simensen et al. |
| 6,339,075 B1 | 1/2002 | King et al. |
| 6,395,307 B1 | 5/2002 | Banning et al. |
| 6,407,226 B1 | 6/2002 | Simensen et al. |
| 6,641,740 B2 | 11/2003 | Cornelius et al. |
| 7,208,141 B2 * | 4/2007 | Montgomery .................. 424/45 |
| 7,671,100 B2 | 3/2010 | Gaserod et al. |
| 7,671,101 B2 | 3/2010 | Gaserod et al. |
| 7,671,102 B2 | 3/2010 | Gaserod et al. |
| 7,674,837 B2 | 3/2010 | Gaserod et al. |
| 7,758,856 B2 | 7/2010 | Hughes et al. |
| 7,776,839 B2 | 8/2010 | Del Buono et al. |
| 7,790,699 B2 | 9/2010 | Melvik et al. |
| 2003/0013678 A1 | 1/2003 | Lang et al. |
| 2003/0022863 A1 | 1/2003 | Stahl et al. |
| 2003/0224070 A1 | 12/2003 | Sweazy et al. |
| 2004/0073964 A1 | 4/2004 | Ellington et al. |
| 2004/0224922 A1 | 11/2004 | King |
| 2010/0068290 A1 | 3/2010 | Ziegler et al. |
| 2010/0305062 A1 * | 12/2010 | Onsoyen et al. .................. 514/54 |

FOREIGN PATENT DOCUMENTS

| DE | 268865 A1 | 1/1987 |
| EP | 0324720 A1 | 7/1989 |
| EP | 0 506 326 A2 | 9/1992 |
| EP | 0590746 A1 | 4/1994 |
| EP | 1234584 A1 | 8/2002 |
| EP | 1714660 A1 | 10/2006 |
| EP | 1745705 A1 | 1/2007 |
| FR | 7576 M | 3/1968 |
| GB | 1042379 | 9/1966 |
| GB | 2430881 A | 4/2007 |
| JP | 05-252970 | 10/1993 |

(Continued)

OTHER PUBLICATIONS

Kitamikado, M. et al. 1993 "Bacteriostatic Action of Oligosaccharides Prepared from Alginate by Enzymatic Degradation" *Nippon Suisan Gakkaishi—Bulletin of the Japanese Society of Scientific Fisheries* 59: 315-320.

Hu, X. et al. 2005 "Antibacterial activity of lyase-depolymerized products of alginate" *Journal of Applied Phycology* 17: 57-60.

Office Action in corresponding Chinese Application No. CN 200880118093.0 dated Nov. 29, 2012.

Office Action in corresponding Chinese Application No. CN 201080034492.6 dated Oct. 24, 2012.

Office Action in corresponding Russian Application No. 2010120766 dated Sep. 26, 2012.

(Continued)

*Primary Examiner* — Dirk Bass
(74) *Attorney, Agent, or Firm* — Knobbe, Martens, Olson & Bear, LLP

(57) ABSTRACT

The invention provides a method of overcoming resistance to at least one antibiotic in a multidrug resistant bacterium, said method comprising contacting said bacterium with an alginate oligomer together with the antibiotic. The multidrug resistant bacterium may be on an animate or inanimate surface and both medical and non-medical uses and methods are provided. In one aspect the invention provides an alginate oligomer for use together with at least one antibiotic in treating a subject infected, suspected to be infected, or at risk of infection, with a multidrug resistant bacterium to overcome resistance to the antibiotic in said multidrug resistant bacterium. In another aspect the method can be used to combat contamination of a site with multidrug resistant bacteria, e.g. for disinfection and cleaning purposes.

41 Claims, No Drawings

(56) References Cited

FOREIGN PATENT DOCUMENTS

| | | |
|---|---|---|
| JP | 09208472 | 8/1997 |
| JP | 2005145885 | 11/2003 |
| JP | 2008285431 | 5/2007 |
| KR | 20000032630 | 11/1998 |
| WO | WO 88/09794 A1 | 12/1988 |
| WO | WO 91/11205 A1 | 8/1991 |
| WO | WO 94/09124 A1 | 4/1994 |
| WO | WO 95/18145 A1 | 7/1995 |
| WO | WO 98/02488 A1 | 1/1998 |
| WO | WO 98/51342 A1 | 11/1998 |
| WO | WO 98/51710 A1 | 11/1998 |
| WO | WO 01/15672 A2 | 3/2001 |
| WO | WO 01/66084 A2 | 9/2001 |
| WO | WO 03/045402 A1 | 6/2003 |
| WO | WO 03/046199 A2 | 6/2003 |
| WO | WO 2004/011628 A1 | 2/2004 |
| WO | WO 2005/023176 A2 | 3/2005 |
| WO | WO 2005/079210 A2 | 9/2005 |
| WO | WO 2006/120705 A2 | 11/2006 |
| WO | WO 2007/039754 A1 | 4/2007 |
| WO | WO 2007/039760 A2 | 4/2007 |
| WO | WO 2008/006658 A1 | 1/2008 |
| WO | WO 2008/071407 A2 | 6/2008 |
| WO | WO 2008/082948 A2 | 7/2008 |
| WO | WO 2008/125828 A2 | 10/2008 |
| WO | WO 2009/018060 A1 | 2/2009 |
| WO | WO 2009/032433 A1 | 3/2009 |
| WO | WO 2009/068841 A2 | 6/2009 |

OTHER PUBLICATIONS

Alkawash, M.A. et al. 2006 "Alginate lyase enhances antibiotic killing of mucoid *Pseudomonas aeruginosa* in biofilms" *APMIS*, 114(2):131-138.
Appleman, M.D. et al. 2000 "In vitro activities of nontraditional antimicrobials against mutiresistant *Acinetobacter baumannii* strains isolated in an intensive care unit outbreak" *Antimicrobial Agents and Chemotherapy* 44: 1035-1040.
Araque-Calderon, Y. et al. 2008 "Antibiotic resistance patterns and SDS-PAGE protein profiles of *Burkholderia cepacia* complex isolates from nosocomial and environmental sources in Venezuela" *Med Sci Monit* 14: BR49-55.
Banning, D. et al. 1997 "Oscillatory and thermorheological characterization of alginate/mucin mixes" *Pharmacy and Pharmacology*, 49(Supp. 4) Poster 65.
Cannon, C. et al. 2006 "Emerging Pulmonary Infections in Cystic Fibrosis" *US Respiratory Disease*, pp. 27-29.
Cuenca, F.F. et al. 2003 "Actividad in vitro de azitromicina frente a aislamientos clinicos de *Acinetobacter baumannii*" *Rev Esp Quimioterap* 16: 204-208.
Dizbay, M. et al. 2009 "Nosocomial *Burkholderia cepacia* infections in a Turkish university hospital: a five-year surveillance" *J Infect Dev Ctries* 3: 273-277.
Djordjevic, D. et al. 2002 "Microtiter Plate Assay for Assessment of *Listeria monocytogenes* Biofilm Formation" *Appl Environ Microbiol* 68:2950-2958.
Donlan, R. M. et al. 2002 "Biofilms: Survival Mechanisms of clinically Relevant Microorganisms" *Clin. Mic. Rev.* 15(2):167-193.
Dunne, W.M. Jr. 2002 "Bacterial Adhesion: Seen Any good Biofilms Lately?" *Clinical Microbiology Reviews*, 15(2):155-166.
Ertesvåg, H. et al. 1999 "Mannuronan C-5-Empimerases and Their Application for in Vitro and in Vivo Design of New Alginates Useful in Biotechnology" *Metabolic Engineering* 1:262-269.
Ferguson, D. et al. 2007 "Phenotypic, molecular and antibiotic resistance profiling of nosocomial *Pseudomonas aeruginosa* strains isolated from two Irish Hospitals" J Medicine vol. 1. (available online at: http://www.scientificjournals.org/journals2007/articles/1055.htm.
Flo, T. et al. 2000 "Involvement of CD14 and β2-Integrins in Activating Cells with Soluble and Particulate Lipopolysaccharides and Mannuronic Acid Polymers" *Infection and Immunity*, 68(12):6770-6776.

Fernandez-Cuenca, F. et al. 2003 "In vitro activity of Azithromycin in combination with Amikacin, Ceftazidime, Ciprofloxacin or Imipenem against clinical isolates of *Acinetobacter baumannii*" *Chemotherapy* 49: 24-26.
Gimmestad, M et al. 2003 "The *Pseudomonas fluorescens* AlgG Protein, but not its Mannuronan C-5-Epimerase Activity, is needed for Alginate Polymer Formation" *Journal of Bacteriology*, 185(12):3515-3523.
Gimmestad, M. et al. 2006 "Identification and Characterization of an *Azotobacter vinelandii* Type I Secretion System Responsible for Export of the AlgE-Type Mannuronan C-5-Epimerases" *Journal of Bacteriology*, 188(15):5551-5560.
Head, N.E. et al. 2004 "Cross-Sectional Analysis of Clinical and Environmental Isolates of *Pseudomonas aeruginosa*: Biofilm Formation, Virulence, and Genome Diversity" *Infection and Immunity* 72(1):133-144.
Jahr T.G. et al. 1997 "Induction of Tumor Necrosis Factor Production from Monocytes Stimulated with Mannuronic Acid Polymers and Involvement of Lipopolysaccharide-Binding Protein, CD14, and Bactericidal/Permeability-increasing Factor" *Infection and Immunity* 65(1):89-94.
Kitamikado, M. et al 1992 "Two Types of Bacterial Alginate Lyases" *Appl Environ Microbiol* 58(8):2474-2478.
Lasa, I. 2006 "Towards the identification of the common features of bacterial biofilm development" *International Microbiology*, 9:21-28.
McGowan, J.E. Jr. "Resistance in nonfermenting gram-negative bacteria: multidrug resistance to the maximum" *Am J Infection Control* 34: S29-S37.
Moore, J.E. et al. 2001 "Antibiotic resistance in *Burkholderia cepacia* at two regional cystic fibrosis centres in Northern Ireland: is there a need for synergy testing?" *J Antimicrobial Chemotherapy* 48: 315-329.
Moskowitz, S.M. et al. 2004 "Clinically Feasible Biofilm Susceptibility Assay for Isolates of *Pseudomonas aeruginosa* from Patients with Cystic Fibrosis" *Journal of Clinical Microbiology* 42(5):1915-1922.
Mrsny R.J., et al. 1994 "Addition of a Bacterial Alginate Lyase to Purulent CF Sputum In Vitro Can Result in the Disruption of Alginate and Modification of Sputum Viscoelasticity" *Pulmonary Pharmacology*, 7:357-366.
Murata, K et al. 1992 "Continuous Depolymerization of Alginates by a Non-Support Bioreactor System Containing Flocculated Bacterial Cells" *Journal of Fermentation and Bioengineering* 73(2):172-174.
Otterlei, M et al. 1991 Induction fo Cytokine Production from Human Monocytes Stimulated with Alginate *Journal of Immunotherapy*, 10:286-291.
Qiu, D, et al. 2007 "Regulated proteolysis controls mucoid conversion in *Pseudomonas aeruginosa*" *Proc Natl Acad Sci USA* 104(19):8107-8112.
Remminghorst, U. et al. 2006 "Bacterial alginates: from biosynthesis to applications" *Biotechnology Letters* 28:1701-1712.
Strugala et al. 2004, "Bioactive Properties of Epimerised Alginates" *Gums and Stabilisers for the Food Industry* 12:84-94.
Tang, J. X. et al. 2005 "Anionic poly(amino acid)s dissolve F-actin and DNA bundles, enhance DNase activity, and reduce the viscosity of cystic fibrosis sputum" *American Journal of Physiology—Lung, Cellular and Molecular Physiology* 289: L599-L605.
Thibault, F.M. et al. 2004 "Antibiotic susceptibility of 65 isolates of *Burkholderia pseudomallei* and *Burkholderia mallei* to 35 antimicrobial agents" *J Antimicrobial Chemotherapy* 54: 1134-1138.
Ying, Q-L et al. 1996 "Alginate, the Slime Exopolysaccharide of *Pseudomonas aeruginosa*, Binds Human Leukocyte Elastase, Retards Inhibition by α-Proteinase Inhibitor, and Accelerates Inhibition by Secretory Leukoprotease Inhibitor" American *Journal of Respiratory Cell and Molecular Biology*, 15:283-291.
Yu, H. et al. 2002 "Persistent Infections and Immunity in Cystic Fibrosis" *Frontiers in Bioscience* 7:d442-457.
Office Action in related United Kingdom Patent Application No. GB1122180.1, dated Jan. 20, 2012.
Office Action in related United Kingdom Patent Application No. GB1122180.1, dated Jul. 10, 2012.
Office Action in related European Patent Application No. 08 875 658.0-2103, dated Jun. 19, 2012.

(56) References Cited

OTHER PUBLICATIONS

Emanuel, C. et al. 2012 "OligoG, a Novel Antimicrobial Alginate Oligosaccharide, Impedes Biofilm Development by Inhibition of Bacterial Motility" Poster No. F-2062 at IACC, San Francisco, Sep. 9-12, 2012.

Khan S. et al. 2010 "Synergistic Activity of OligoG with Anti-Gram-Negative Antibiotics against *Pseudomonas aeruginosa* and *Burkholderia* spp." Poster No. F1-1601 at ICAAC, Boston, Sep. 12-15, 2010.

Khan S. et al. 2010 "Effect of OligoG on Disruption of *Acinetobacter baumannii* Biofilms and Overcoming Multi-Drug Resistance" Poster No. F1-1602 at ICAAC, Boston, Sep. 12-15, 2010.

Khan S. et al. 2010 "Activity of OligoG Alginate Against Gram-Positive Bacteria, Alone and in Combination with Anti-Gram Positive Antibiotics" Poster No. F1-1600 at ICAAC, Boston, Sep. 12-15, 2010.

Khan, S. et al. 2011 "The Antimicrobial Effect of Alginate Oligosaccharides for the Treatment of Multi-Drug Resistant Bacterial Infections may be due to Cell Wall Disruption?" Poster No. F1-154 at ICAAC, Chicago, Sep. 17-20, 2011.

Powell, L. et al. 2012 "The Effects of the Alginate Oligosaccharide Oligo-G on the Surface and Rheological Properties of Gram-Negative Bacterial Biofilms using Atomic Force Microscopy" Poster at European Cystic Fibrosis Conference, Jun. 11, 2012.

Sletta, H. et al. 2011 "The Ability of Novel Alginate Oligosaccharides to Impair Fungal Adherence, Biofilm Formation and Potentiate Conventional Anti-Fungal Therapy in vitro" Poster No. F1-155 at ICAA, Chicago, Sep. 17-20, 2011.

Fridkin, S.K. and Jarvis, W.R. 1996 "Epidemiology of Nosocomial Fungal Infections" *Clinical Microbiology Reviews* 9: 499-511.

Sakai, S. et al. 2002 "Permeability of alginate/sol-gel synthesized aminopropyl-silicate/alginate membrane templated by calcium-alginate gel" *J Membrane Sci* 205: 183-189.

\* cited by examiner

ALGINATE OLIGOMERS FOR USE IN OVERCOMING MULTIDRUG RESISTANCE IN BACTERIA

The present invention relates to alginate oligomers for use together with (or in combination or conjunction with) an antibiotic to overcome (in the sense of reducing) resistance to the antibiotic in a multidrug resistant (MDR) bacterium. Whilst a principal and important use of the present invention is in the treatment or prevention of bacterial infections with MDR bacteria, namely a medical use, the invention also encompasses such use of alginate oligomers in non-medical settings (e.g. in vitro). The invention thus provides alginate oligomers for use together with (or in combination or conjunction with) an antibiotic for the treatment or prevention of an MDR bacterial infection in a subject, or for combating MDR resistant bacteria in vitro (for example in combating the microbial contamination (i.e. colonisation) of an abiotic site with MDR bacteria).

Ever since antibiotics were first used it was appreciated that bacteria could display intrinsic resistance to these drugs or could develop resistance to these drugs. Resistance of a bacterium to an antibiotic can be viewed as a substantially greater tolerance, or reduced susceptibility, to the antibiotic compared to a sensitive bacterium or a typical or a wild type version of the bacterium. In some cases a bacterium can be completely unaffected by exposure to an antibiotic. In this instance the bacterium can be considered fully resistant to that antibiotic.

Multidrug resistance (MDR) in bacteria describes the situation where a bacterium is resistant to at least three classes of drugs, specifically in the context of bacteria, at least three classes of anti-microbial (or more specifically anti-bacterial) agents, and particularly in the context of the present invention, at least three classes of antibiotics. Antibiotics in one class are functionally unrelated, structurally unrelated, or both, to antibiotics in a different class. MDR in bacteria is thus often termed multiple anti-bacterial drug resistance or multiple antibiotic resistance. The terms are used interchangeably in the art and herein. Bacteria displaying multi-drug resistance phenotypes (or multiple antibacterial/antibiotic drug resistance phenotypes) are referred to as MDR bacteria (or sometimes MAR bacteria). Again, these terms are used interchangeably in the art and herein.

Antibiotic resistance mechanisms are numerous. For instance, resistance may arise from impermeability mechanisms which physically prevent the antibiotic reaching its site of action in or on the bacterium; efflux mechanisms which prevent effective amounts of the antibiotic reaching its site of action in or on the bacterium by rapidly removing the antibiotic from the bacterium; metabolic mechanisms which breakdown the antibiotic or convert the antibiotic into a harmless (or less harmful) compound, or a compound more easily excreted; bypass mechanisms in which the bacterium uses alternative pathways to those inhibited by the antibiotic; or through the bacterium having a form of the antibiotic target (e.g. enzyme) that is less sensitive to the antibiotic or not having the target at all.

Resistance to a particular antibiotic or class of antibiotic may be intrinsic to the bacterium, but it can also be developed or acquired. Generally intrinsic resistance may be seen to a particular type or class of antibiotic, but the number of different antibiotic classes to which resistance is seen is usually restricted. Resistance to numerous classes of antibiotics (including to multiple classes of antibiotics, which is defined herein as at least three classes of antibiotics) may be an acquired (or developed) phenomenon, but this is not exclusively the case. Thus, in the case of MDR bacteria, the bacteria may acquire or develop resistance to particular antibiotic classes (e.g., to one or more or two or more classes, for example additional classes, or to 3 or more classes), or in certain cases the bacteria may be intrinsically resistant to multiple classes. The resistant phenotype of MDR bacteria can differ from typical or wild type bacteria, but certain bacteria can be considered MDR on account of their intrinsic resistance profile, e.g. *Burkholderia* species including *Burkholderia cepacia*, *Burkholderia mallei*, and *Burkholderia pseudomallei*.

Development (or acquisition) of resistance can be through mutation. For instance, this may involve changes in the structure of the target of the antibiotic that reduces the sensitivity of the target to the antibiotic. It can also be a mutation in a pathway involved in the regulation of the cellular machinery involved in the metabolism or efflux of the antibiotic. It can also be a mutation in the constituents of the outer layers (e.g. the membranes/walls) of the bacterium that effects the permeability of the antibiotic into the bacterium. In some instances multiple mutations must accumulate in order for a bacterium to become resistant to a particular antibiotic or class thereof.

Development of resistance can also be through the transfer of a resistance mechanism from another organism, e.g. another bacterium (this is sometimes referred to as acquired resistance, but as used herein the term "acquired resistance" includes any means or mechanism by which the resistance arises, including by transfer or by mutation). This is usually, although not exclusively, though the transfer from organism to organism of mobile nucleic acids encoding the resistance mechanism (e.g. β-lactamase).

As a consequence of the inherent selective pressure antibiotics exert on a bacterial population, the use of antibiotics selects for resistant members of that population. The sequential use of different antibiotics in a treatment regime can therefore give rise to MDR bacteria.

Many MDR species and strains of bacteria exist today. Bacterial genera from which MDR species and strains pose significant problems for human and animal health include, but are not limited to *Pseudomonas*, *Acinetobacter*, *Burkholderia*, *Klebsiella*, *Providencia*, and *Staphylococcus*

*Pseudomonas* is a genus of strictly aerobic, gram-negative bacteria of relatively low virulence. Nevertheless, *Pseudomonas* species can act as opportunistic pathogens and infections have been reported with *Pseudomonas aeruginosa*, *Pseudomonas oryzihabitans*, *Pseudomonas luteola*, *Pseudomonas anguilliseptica* and *Pseudomonas plecoglossicida*.

*P. plecoglossicida* and *P. anguilliseptica* are fish pathogens. *P. oryzihabitans* can be a human pathogen causing peritonitis, endophthalmitis, septicemia and bacteriaemia. Similar infections can be caused by *P. luteola*. The majority of *Pseudomonas* infections in humans are, however, caused by *P. aeruginosa*.

*P. aeruginosa* is a widespread and extremely versatile bacteria that can be considered a part of the natural flora of a healthy subject and is capable of colonising most man-made environments. This ubiquity and versatility has seen colonisation of healthcare environments by *P. aeruginosa*. Problematically, the same versatility enables *P. aeruginosa* to act as an opportunistic human pathogen in impaired subjects, most commonly immunocompromised patients (e.g. those with, cystic fibrosis or AIDS) and patients with a compromised barrier to infections (e.g. those with chronic wounds and burns and those with in-dwelling medical devices such as intravenous lines, urinary catheters, dialysis catheters, endotracheal tubes).

*P. aeruginosa* infection can affect many different parts of the body, but infections typically target the respiratory tract, the GI tract, the urinary tract and surface wounds and burns and in-dwelling medical devices. This problem is compounded by the presence of intrinsic resistance to many of the β lactam antibiotics. Acquired resistance of certain strains to further antibiotics is also being reported. The ability of certain strains of *P. aeruginosa* to form biofilms adds further to these problems because biofilm-dwelling bacteria are often more resistant to anti-microbials than their non-biofilm counterparts. As such, there is an urgent need for safe and effective treatments for *Pseudomonas* infections and contamination and, in particular, treatments that overcome antibiotic resistance, particularly β-lactam resistance, in *Pseudomonas* species.

*Burkholderia* is a genus of gram-negative, motile, obligate aerobic, non-fermenting rod-shaped bacteria. *Burkholderia* species are widely distributed in nature and include animal and plant pathogens. *Burkholderia cepacia* is emerging as a human pathogen of note. *B. cepacia* has been reported to have caused necrotizing pneumonia, ventilator-associated pneumonia, bacteraemia, and infections of the skin, soft tissue, bloodstream, respiratory tract, and urinary tract in cystic fibrosis patients and hospitalised patients. *Burkholderia cepacia is* a part of a group of at least nine different species forming the *Burkholderia cepacia* complex (BCC), including *B. multivorans, B. cenocepacia, B. vietnamiensis, B. stabilis, B. ambifaria, B. dolosa, B. anthina*, and *B. pyrrocinia*

*Burkholderia pseudomallei*, is the causative agent of melioidosis, a potentially fatal community-acquired infectious disease endemic to southeast Asia, Taiwan and northern Australia. Cases have also been described in China, India, Central and South America, the Middle East, and several African countries. Incidences of the disease amongst servicemen engaged in conflicts in these areas have been reported and spread of the diseases back to the country of origin of these servicemen has been noted and is a consequence of the fact that relapses are common and the disease can remain latent for long periods before clinical manifestation.

*Burkholderia mallei*, is the causative agent of glanders, an infectious disease that primarily affecting horses, mules and donkeys, but it has been reported in other animals, e.g. dogs, cats and goats, and in particular, transmission to humans can occur. Transmission from the animal to human typically occurs by direct contact through skin abrasions, nasal and oral mucosal surfaces, or by inhalation.

Problematically, pathogenic *Burkholderia* species often display intrinsic resistance to multiple antibiotics and antibiotic classes (e.g. one or more of the aminoglycosides, β-lactams and macrolides) and persistence in betadine (a topical antiseptic used commonly in hospitals) has been noted. Acquired resistance of certain strains to further antibiotics is also being reported. As such, there is an urgent need for safe and effective treatments for *Burkholderia* infections and contamination and, in particular, treatments that overcome antibiotic resistance, particularly, β-lactam and macrolide resistance, in *Burkholderia* species.

*Providencia* is a genus of gram-negative bacilli that are responsible for a wide range of human infections. *Providencia* infections are usually nosocomial and are found predominantly in the urinary tract, often as a consequence of catheterisation. *Providencia* infections are also associated with gastroenteritis and bacteraemia and surface infections of chronic wounds and burns. They represent an emerging problem because of the increasing prevalence of strains with β-lactam antibiotic resistance due to the spread amongst *Providencia* populations of extended-spectrum beta-lactamase (ESBL).

*Providencia* species include *Providencia stuartii, Providencia sneebia, Providencia rettgeri, Providencia rustigianii, Providencia heimbachae, Providencia burhodogranariea* and *Providencia alcalifaciens. Providencia* species have been found in soil, water and sewage and in multiple animal reservoirs. Examples of *Providencia* infections in animals include neonatal diarrhoea in cattle due to *P. stuartii* infection and enteritis caused by *P. alcalifaciens* infection in dogs. *P. rettgeri* has been isolated in crocodiles with meningitis/septicaemia and in chickens with enteritis. *P. heimbachae* has been isolated in penguin faeces and aborted bovine foetuses.

In humans, *Providencia* species have been isolated from urine, stool, and blood, as well as from sputum, skin, and wound cultures. *P. stuartii* is frequently isolated in patients with indwelling urinary catheters and is known to persist in the urinary tract after bladder access is attained. *P. stuartii* can give rise to septicaemia, and commonly this is secondary to the infection of the urinary tract. *P. stuartii* has also been reported as the etiology of infective endocarditis. *P. rettgeri* has been reported to be a cause of ocular infections, including keratitis, conjunctivitis, and endophthalmitis. *P. alcalifaciens, P. rettgeri*, and *P. stuartii* have also been implicated in gastroenteritis.

*Providencia* infections with antimicrobial resistance patterns are increasing and ESBL-positive *P. stuartii* is an increasing problem in hospitalized patients. As such, there is an urgent need for safe and effective treatments for *Providencia* infections and contamination and, in particular, treatments that overcome antibiotic resistance, particularly β-lactam resistance, in *Providencia* species.

*Acinetobacter* is a genus of bacteria that are strictly aerobic non-fermentative gram-negative bacilli. *Acinetobacter* species are widely distributed in nature and can survive for long periods of time on wet or dry surfaces. *Acinetobacter* species are considered to be non-pathogenic to healthy subjects, but it is becoming increasingly apparent that *Acinetobacter* species persist in hospital environments for a long period of time and can be responsible for nosocomial infections in compromised patients. *Acinetobacter baumannii* is a frequent cause of nosocomial pneumonia, especially of late-onset ventilator associated pneumonia and it can cause various other infections including skin and wound infections, bacteraemia, and meningitis. *Acinetobacter lwoffii* has also been associated with meningitis. Other species including *Acinetobacter haemolyticus, Acinetobacter johnsonii, Acinetobacter junii, Acinetobacter radioresistens, Acinetobacter tandoii, Acinetobacter tjernbergiae, Acinetobacter towneri*, or *Acinetobacter ursingii* have also been linked to infection. Of particular note is the prevalence of *Acinetobacter baumannii* infections in US serviceman stationed in the Middle East, e.g. Iraq. Of concern is the fact that many *Acinetobacter* strains appear to be multidrug resistant, thus making the combat of *Acinetobacter* infections and contamination difficult. As such, there is an urgent need for safe and effective treatments for *Acinetobacter* infections and contamination.

*Klebsiella* is a genus of non-motile, gram-negative, rod shaped bacteria *Klebsiella* species are ubiquitous in nature. In humans, they may colonize the skin, pharynx, and gastrointestinal tract and may be regarded as normal flora in many parts of the colon, the intestinal tract and in the biliary tract.

*Klebsiella* species include, *Klebsiella granulomatis, Klebsiella oxytoca, Klebsiella pneumoniae, Klebsiella singapo-*

*rensis*, and *Klebsiella variicola*, although *K. pneumoniae* and *K. oxytoca* are the members of this genus responsible for most human infections. Such infections include pneumonia, bacteraemia, thrombophlebitis, urinary tract infection, cholecystitis, diarrhoea, upper respiratory tract infection, wound infection, osteomyelitis, and meningitis. Rhinoscleroma and ozena are two other infections caused by *Klebsiella* species. Rhinoscleroma is a chronic inflammatory process involving the nasopharynx, whereas ozena is a chronic atrophic rhinitis characterized by necrosis of nasal mucosa and mucopurulent nasal discharge.

Klebsiellae often contribute to nosocomial infections. Common sites include the urinary tract, lower respiratory tract, biliary tract, and wounds. The presence of invasive devices, in particular respiratory support equipment and urinary catheters, increase the likelihood of nosocomial infection with *Klebsiella* species. Sepsis and septic shock may follow entry of organisms into the blood from these sources.

*K. pneumoniae* is an important cause of community-acquired pneumonia in elderly persons and subjects with impaired respiratory host defences. *K. oxytoca* has been implicated in neonatal bacteraemia, especially among premature infants and in neonatal intensive care units. Increasingly, the organism is being isolated from patients with neonatal septicaemia.

Problematically, resistance of *Klebsiella* species to antibiotics is increasing. As such, there is an urgent need for safe and effective treatments for *Klebsiella* infections and contamination and, in particular, treatments that overcome antibiotic resistance in *Klebsiella* species.

Antibiotics are a key tool in the clinical management of bacterial infections, e.g. those involving the genera mentioned above. Unfortunately, the number of antibiotics available to physicians is finite and has remained largely unchanged for many years. Resistance of a bacterium to an antibiotic reduces the number of antibiotics available to treat the bacterium. Bacteria resistant to multiple antibiotics are therefore proportionately more difficult to treat. Continued use of antibiotics inevitably selects for MDR bacteria and so there is an urgent need for techniques by which MDR phenotypes can be overcome. The inventors have surprisingly found that alginate oligomers can achieve this. Alginates are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate).

Alginates have been isolated from marine brown algae (e.g. certain species of *Durvillea, Lessonia* and *Laminaria*) and bacteria such as *Pseudomonas aeruginosa* and *Azotobacter vinelandii*. Other pseudomonads (e.g. *Pseudomonas fluorescens, Pseudomonas putida*, and *Pseudomonas mendocina*) retain the genetic capacity to produce alginates but in the wild they do not produce detectable levels of alginate. By mutation these non-producing pseudomonads can be induced to produce stably large quantities of alginate.

Alginate is synthesised as polymannuronate and G residues are formed by the action of epimerases (specifically C-5 epimerases) on the M residues in the polymer. In the case of alginates extracted from algae, the G residues are predominantly organised as G blocks because the enzymes involved in alginate biosynthesis in algae preferentially introduce the G neighbouring another G, thus converting stretches of M residues into G-blocks. Elucidation of these biosynthetic systems has allowed the production of alginates with specific primary structures (WO 94/09124, Gimmestad, M et al, Journal of Bacteriology, 2003, Vol 185(12) 3515-3523 and WO 2004/011628).

Alginates are typically isolated from natural sources as large high molecular weight polymers (e.g. an average molecular weight in the range 300,000 to 500,000 Daltons). It is known, however, that such large alginate polymers may be degraded, or broken down, e.g. by chemical or enzymatic hydrolysis to produce alginate structures of lower molecular weight. Alginates that are used industrially typically have an average molecular weight in the range of 100,000 to 300,000 Daltons (such alginates are still considered to be large polymers) although alginates of an average molecular weight of approximately 35,000 Daltons have been used in pharmaceuticals.

It has now been found that alginate oligomers can be used to overcome antibiotic resistance and render bacteria that are MDR (resistant to multiple classes of antibiotics) susceptible to antibiotics (more specifically susceptible to antibiotic(s) to which they are resistant) and so the use of alginate oligomers together with antibiotics constitutes a highly effective approach to the combat of contamination and infections caused by MDR bacteria.

Accordingly, in a first aspect the invention provides a method of overcoming resistance to at least one antibiotic in an MDR bacterium, said method comprising contacting said bacterium with an alginate oligomer together with (or in conjunction or combination with) the antibiotic.

More particularly, the contacting step may comprise contacting the bacterium (more particularly the bacteria) with an alginate oligomer at the same, or substantially the same, time or prior to contacting the bacterium with the antibiotic in an amount effective to overcome the resistance of the bacteria to the antibiotic. In particular, the step of contacting the bacterium with the alginate oligomer may include administering the alginate oligomer to a subject, and in particular to a subject in need of such treatment (e.g. a subject infected with, suspected to be infected with, or at risk of infection with, an MDR bacterium).

Thus the invention provides an alginate oligomer for use together with (or in combination or conjunction with) at least one antibiotic in treating a subject infected, suspected to be infected, or at risk of infection, with an MDR bacterium to overcome resistance to the antibiotic in said MDR bacterium.

This aspect of the invention also provides a method of treating a subject infected, suspected to be infected, or at risk of infection, with an MDR bacterium to overcome resistance to the antibiotic in said MDR bacterium, said method comprising administering an effective amount of the antibiotic to said subject together with an effective amount of said alginate oligomer.

By "use together" it is particularly meant that a pharmaceutically effective amount of the alginate oligomer and a pharmaceutically effective amount of the antibiotic are administered in a manner that results in the bacterium (more particularly the bacteria) being contacted with an alginate oligomer at the same, or substantially the same, time or prior to being contacted with the antibiotic. Any clinically acceptable dosing regime may be used to achieve this. The skilled man would be able to take into account any relevant variable factors (e.g. the routes of administration, the bioavailability, and the pharmacokinetics of the oligomer and the antibiotic being used, the subject's physical state, the location of the bacterium, etc.) in order to design an appropriate dosing regime for a particular subject. In one embodiment, a pharmaceutically effective amount of the alginate oligomer is administered at the same or substantially the same time as or prior to administering a pharmaceutically effective amount of the antibiotic. In other embodiments the oligomer is administered separately to and after the antibiotic. The skilled man would readily be able to design his dosing regime to maximise the effect of the alginate oligomer and antibiotic he is using in overcoming the resistance of the target MDR bacterium to the antibiotic. He would also be able to select optimal combinations of the two active agents depending on the particular clinical situation he is faced with. "Use together" does not imply that the respective agents are present in the same formulation or composition, and accordingly even if used, or administered, at the same or substantially the same time, the alginate oligomer and antibiotic need not, indeed most likely will not, be present in the same composition or formulation, but may be administered separately. Thus "separate" use/administration includes use/administration at the same or substantially the same time, or at different times, e.g. sequentially, or at different time intervals according to the desired dosage or usage regime.

The term "infected with" (or "infected by") is used broadly herein to indicate that the subject may comprise, or contain, or carry, the bacterium in question, i.e. that the bacterium may simply be present in or on the subject, and this may include any site or location in or on the body of the subject. It is not necessary that the infection of the subject be manifest as a clinical disease (i.e. that the infection result in clinical symptoms in the subject), although this is of course encompassed. A subject who is suspected to be infected or who is at risk of infection may be a subject who has been exposed to the bacterium or to an infected subject, or a subject presenting with clinical signs or symptoms of infection (in the case of a suspected infection), or a subject who is susceptible to infection, whether generally e.g. due to the clinical status of the subject) or particularly to the bacterium in question.

Alternatively put, the invention provides the use of an alginate oligomer for the manufacture of a medicament for use together with at least one antibiotic in treating a subject infected, suspected to be infected, or at risk of infection, with an MDR bacterium to overcome resistance to the antibiotic in said MDR bacterium.

The medicament may further comprise the antibiotic (or antibiotics). The medicament may be in the form of a single composition or formulation comprising the alginate oligomer and antibiotic(s) or separate compositions or formulations may be prepared and used, each containing the alginate oligomer or the antibiotic(s), respectively.

Thus in a more particular aspect the present invention provides the use of an alginate oligomer and at least one antibiotic for the manufacture of a medicament for use in treating a subject infected, suspected to be infected, or at risk of infection, with an MDR bacterium to overcome resistance to the antibiotic in said MDR bacterium.

As noted above, the antibiotic may be applied or administered separately from the alginate oligomer.

Thus a further aspect of the present invention provides a product containing an alginate oligomer and an antibiotic (e.g. one or more antibiotics) as a combined preparation for separate, simultaneous or sequential use, in treating a subject infected, suspected to be infected, or at risk of infection, with an MDR bacterium to overcome resistance to the antibiotic in said MDR bacterium.

The antibiotic may be applied or administered simultaneously with the alginate oligomer or sequentially. As noted above, in one embodiment the antibiotic is administered at the same or substantially the same time as the alginate oligomer, and in another embodiment it is administered after the alginate oligomer. In other embodiments the oligomer is administered separately to and after the antibiotic. Included within the scope of "substantially the same time" is application or administration of the antibiotic immediately or almost immediately before or after the alginate oligomer. The term "almost immediately" may be read as including application or administration within one hour of the previous application or administration, preferably within 30 minutes. However the antibiotic may be applied or administered at least 1 hour, at least 3 hours, or at least 6 hours or more after the alginate oligomer. In these embodiments the antibiotic can be applied or administered with or without a further application of an alginate oligomer. The alginate oligomer can be applied or administered in a plurality of applications prior to or with the antibiotic, including as noted above, an application or administration immediately or almost immediately after the antibiotic. In other embodiments the antibiotic(s) may conveniently be applied or administered before the alginate oligomer, e.g. at least 1 hour, at least 3 hours, at least 6 hours before the alginate oligomer. In these embodiments the alginate oligomer can be applied or administered with or without a further application of the antibiotic. The antibiotic can be applied or administered in a plurality of applications prior to or with the alginate oligomer.

As noted above, alginates typically occur as polymers of an average molecular weight of at least 35,000 Daltons i.e. approximately 175 to approximately 190 monomer residues, although typically much higher and an alginate oligomer according to the present invention may be defined as a material obtained by fractionation (i.e. size reduction) of an alginate polymer, commonly a naturally occurring alginate. An alginate oligomer can be considered to be an alginate of an average molecular weight of less than 35,000 Daltons (i.e. less than approximately 190 or less than approximately 175 monomer residues), in particular an alginate of an average molecular weight of less than 30,000 Daltons (i.e. less than approximately 175 or less than approximately 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more units or residues and an alginate oligomer for use according to the invention will typically contain 2 to 100 monomer residues, preferably 2 to 75, preferably 2 to 50, more preferably 2 to 40, 2 to 35 or 2 to 30 residues. Thus an alginate oligomer for use according to the invention will typically have an average molecular weight of 350 to 20,000 Daltons, preferably 350 to 15,000 Daltons, preferably 350 to 10,000 Daltons and more preferably 350 to 8000 Daltons, 350 to 7000 Daltons, or 350 to 6,000 Daltons.

Alternatively put, the alginate oligomer may have a degree of polymerisation (DP), or a number average degree of polymerisation (DPn) of 2 to 100, preferably 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include any one of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

The alginate oligomer is preferably a linear oligomer.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include alginate oligomers with (e.g. containing) 30 to 70% G (guluronate) residues or 70 to 100% G (guluronate) residues. Thus, a representative alginate oligomer for use according to the present invention may contain at least 70% G residues (i.e. at least 70% of the monomer residues of the alginate oligomer will be G residues).

Preferably at least 50% or 60%, more particularly at least 70% or 75%, even more particularly at least 80, 85, 90, 91, 92, 93, 94, 95, 96, 97, 98 or 99% of the monomer residues are guluronate. In one embodiment the alginate oligomer may be an oligoguluronate (i.e. a homooligomer of G, or 100% G)

In a further preferred embodiment, the above described alginates of the invention have a primary structure wherein the majority of the G residues are in so called G-blocks. Preferably at least 50%, more preferably at least 70 or 75%, and most preferably at least 80, 85, 90, 92 or 95% of the G residues are in G-blocks. A G block is a contiguous sequence of at least two G residues, preferably at least 3 contiguous G residues, more preferably at least 4 or 5 contiguous G residues, most preferably at least 7 contiguous G residues.

In particular at least 90% of the G residues are linked 1-4 to another G residue. More particularly at least 95%, more preferably at least 98%, and most preferably at least 99% of the G residues of the alginate are linked 1-4 to another G residue.

The alginate oligomer of use in the invention is preferably a 3- to 35-mer, more preferably a 3- to 28-mer, in particular a 4- to 25-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons or 2000 to 3000 Daltons. Other representative alginate oligomers include, as mentioned above, oligomers with 7, 8, 9, 10, 11 or 12 to 50, 45, 40, 35, 28, 25, 22 or 20 residues.

It may be a single compound or it may be a mixture of compounds, e.g. of a range of degrees of polymerization. As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

The alginate oligomer of the invention may have a degree of polymerisation (DP), or a number average degree of polymerisation ($DP_n$), of 3-28, 4-25, 6-22, 8-20 or 10-15, or 5 to 18 or 7 to 15 or 8 to 12, especially 10.

The alginate oligomer of the invention may have a degree of polymerisation (DP), or a number average degree of polymerisation ($DP_n$), of 8-50, 8-40, 8-35, 8-30, 8-28, 8-25, 8-22, 8-20, 8-18, 8-16 or 8-14.

The alginate oligomer of the invention may have a degree of polymerisation (DP), or a number average degree of polymerisation ($DP_n$), of 9-50, 9-40, 9-35, 9-30, 9-28, 9-25, 9-22, 9-20, 9-18, 9-16 or 9-14.

The alginate oligomer of the invention may have a degree of polymerisation (DP), or a number average degree of polymerisation ($DP_n$), of 10-50, 10-40, 10-35, 10-30, 10-28, 10-25, 10-22, 10-20, 10-18, 10-16 or 10-14.

The alginate oligomer of the invention may have a degree of polymerisation (DP), or a number average degree of polymerisation ($DP_n$), of 12-50, 12-40, 12-35, 12-30, 12-28, 12-25, 12-22, 12-20, 12-18, 12-16 or 12-14.

The alginate oligomer of the invention may have a degree of polymerisation (DP), or a number average degree of polymerisation ($DP_n$), of 15-50, 15-40, 15-35, 15-30, 15-28, 15-25, 15-22, 15-20, 15-18 or 15-16.

The alginate oligomer of the invention may have a degree of polymerisation (DP), or a number average degree of polymerisation ($DP_n$), of 18-50, 18-40, 18-35, 18-30, 18-28, 18-25, 18-22 or 18-20.

Preferably the alginate oligomer of the invention is substantially free, preferably essentially free, of alginate oligomers having a degree of polymerisation outside of the ranges disclosed herein. This may be expressed in terms of the molecular weight distribution of the alginate oligomer of the invention, e.g. the percentage of each mole of the alginate oligomer being used in accordance with the invention which has a DP outside the relevant range. The molecular weight distribution is preferably such that no more than 10%, preferably no more than 9, 8, 7, 6, 5, 4, 3, 2, or 1% mole has a DP of three, two or one higher than the relevant upper limit for $DP_n$. Likewise it is preferred that no more than 10%, preferably no more than 9, 8, 7, 6, 5, 4, 3, 2, or 1% mole has a DP below a number three, two or one smaller than the relevant lower limit for $DP_n$.

Suitable alginate oligomers are described in WO2007/039754, WO2007/039760, WO 2008/125828, and WO2009/068841, the disclosures of which are explicitly incorporated by reference herein in their entirety.

Representative suitable alginate oligomers have a $DP_n$ in the range 5 to 30, a guluronate/galacturonate fraction ($F_G$) of at least 0.80, a mannuronate fraction ($F_M$) of no more than 0.20, and at least 95 mole % of DP no more than 25.

Further suitable alginate oligomers have a number average degree of polymerization in the range 7 to 15 (preferably 8 to 12), a guluronate/galacturonate fraction ($F_G$) of at least 0.85 (preferably at least 0.90), a mannuronate fraction ($F_M$) of no more than 0.15 (preferably no more than 0.10), and having at least 95% mole with a degree of polymerization less than 17 (preferably less than 14).

Further suitable alginate oligomers have a number average degree of polymerization in the range 5 to 18 (especially 7 to 15), a guluronate/galacturonate fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17).

Further suitable alginate oligomers have a number average degree of polymerization in the range 5 to 18, a guluronate/galacturonate fraction ($F_G$) of at least 0.92, a mannuronate fraction ($F_M$) of no more than 0.08, and having at least 95% mole with a degree of polymerization less than 20.

Further suitable alginate oligomers have a number average degree of polymerization in the range 5 to 18 (preferably 7 to 15, more preferably 8 to 12, especially about 10), a guluronate/galacturonate fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14).

Further suitable alginate oligomers have a number average degree of polymerization in the range 7 to 15 (preferably 8 to 12), a guluronate/galacturonate fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Further suitable alginate oligomers have a number average degree of polymerization in the range 5 to 18, a guluronate/galacturonate fraction ($F_G$) of at least 0.80, a mannuronate fraction ($F_M$) of no more than 0.20, and having at least 95% mole with a degree of polymerization less than 20.

Further suitable alginate oligomers have a number average degree of polymerization in the range 7 to 15, a guluronate/galacturonate fraction ($F_G$) of at least 0.85, a mannuronate fraction ($F_M$) of no more than 0.15, and having at least 95% mole with a degree of polymerization less than 17.

Further suitable alginate oligomers have a number average degree of polymerization in the range 7 to 15, a guluronate/galacturonate fraction ($F_G$) of at least 0.92, a mannuronate fraction ($F_M$) of no more than 0.08, and having at least 95% mole with a degree of polymerization less than 17.

It will thus be seen that a particular class of alginate oligomers favoured according to the present invention is alginate oligomers defined as so-called "high G" or "G-block" oligomers i.e. having a high content of G residues or G-blocks (e.g. wherein at least 70% of the monomer residues are G, preferably arranged in G-blocks). However, other types of alginate oligomer may also be used, including in particular "high M" or "M-block" oligomers or MG-block oligomers, as described further below. Accordingly, it is alginate oligomers with high proportions of a single monomer type, and with said monomers of this type being present predominantly in contiguous sequences of that monomer type, that represent oligomers that are particularly preferred, e.g. oligomers wherein at least 70% of the monomer residues in the oligomer are G residues linked 1-4 to another G-residue, or more preferably at least 75%, and most preferably at least 80, 85, 90, 92, 93, 94, 95, 96, 97, 98, 99% of the monomers residues of the oligomer are G residues linked 1-4 to another G residue. This 1-4 linkage of two G residues can be alternatively expressed as a guluronic unit bound to an adjacent guluronic unit.

In a further embodiment at least, or more particularly more than, 50% of the monomer residues of the alginate oligomer may be M residues (i.e. mannuronate or mannuronic acid). In other words the alginate oligomer will contain at least or alternatively more than 50% mannuronate (or mannuronic acid) residues. Specific embodiments thus include alginate oligomers with (e.g. containing) 50 to 70% M (mannuronate) residues or e.g. 70 to 100% M (mannuronate) residues. Further specific embodiments also include oligomers containing 71 to 85% M residues or 85 to 100% M residues. Thus, a representative alginate oligomer for use according to this embodiment of the present invention will contain more than 70% M residues (i.e. more than 70% of the monomer residues of the alginate oligomer will be M residues).

In other embodiments at least 50% or 60%, more particularly at least 70% or 75%, even more particularly at least 80, 85, 90, 95 or 99% of the monomer residues are mannuronate. In one embodiment the alginate oligomer may be an oligomannuronate (i.e. a homooligomer of M, or 100% M).

In a further embodiment, the above described alginates of the invention have a primary structure wherein the majority of the M residues are in so called M-blocks. In this embodiment preferably at least 50%, more preferably at least 70 or 75%, and most preferably at least 80, 85, 90 or 95% of the M residues are in M-blocks. An M block is a contiguous sequence of at least two M residues, preferably at least 3 contiguous M residues, more preferably at least 4 or 5 contiguous M residues, most preferably at least 7 contiguous M residues.

In particular, at least 90% of the M residues are linked 1-4 to another M residue. More particularly at least 95%, more preferably at least 98%, and most preferably at least 99% of the M residues of the alginate are linked 1-4 to another M residue.

Other preferred oligomers are alginate oligomers wherein at least 70% of the monomer residues in the oligomer are M residues linked 1-4 to another M-residue, or more preferably at least 75%, and most preferably at least 80, 85, 90, 92, 93, 94, 95, 96, 97, 98, 99% of the monomers residues of the oligomer are M residues linked 1-4 to another M residue. This 1-4 linkage of two M residues can be alternatively expressed as a mannuronic unit bound to an adjacent mannuronic unit.

In a still further embodiment, the alginate oligomers of the invention comprise a sequence of alternating M and G residues. A sequence of at least three, preferably at least four, alternating M and G residues represents an MG block. Preferably the alginate oligomers of the invention comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue. Preferably the MG block is at least 5 or 6 contiguous residues, more preferably at least 7 or 8 contiguous residues.

In a further embodiment the minority uronate in the alginate oligomer (i.e. mannuronate or guluronate) is found predominantly in MG blocks. In this embodiment preferably at least 50%, more preferably at least 70 or 75% and most preferably at least 80, 85, 90 or 95% of the minority uronate monomers in the MG block alginate oligomer are present in MG blocks. In another embodiment the alginate oligomer is arranged such that at least 50%, at least 60%, at least 70%, at least 80%, at least 85%, at least 90%, at least 95%, at least 99%, e.g. 100% of the G and M residues in the oligomer are arranged in MG blocks.

Although at its broadest, the invention extends to embodiments wherein at least 1% but less than 100% of the monomer residues of the oligomer are G residues (i.e. guluronate or guluronic acid), more particularly, and as defined further below, at least 30% of the monomer residues are G residues. Thus, at its broadest the MG block containing alginate oligomer may contain at least 1%, but less than 100%, guluronate (or guluronic acid) residues, but generally the MG block containing alginate oligomer will contain at least 30% (or at least 35, 40 or 45% or 50% G) but less than 100% G. Specific embodiments thus include MG block containing alginate oligomers with (e.g. containing) 1 to 30% G (guluronate) residues, 30 to 70% G (guluronate) residues or 70 to 99% G (guluronate) residues. Thus, a representative MG block containing alginate oligomer for use according to the present invention may contain more than 30%, but less than 70%, G residues (i.e. more than 30%, but less than 70%, of the monomer residues of the MG block alginate oligomer will be G residues).

Preferably more than 30%, more particularly more than 35% or 40%, even more particularly more than 45, 50, 55, 60 or 65%, but in each, case less than 70%, of the monomer residues of the MG block containing alginate oligomer are guluronate. Alternatively, less than 70%, more preferably less than 65% or 60%, even more preferably less than 55, 50, 45, 40 or 35%, but in each case more than 30% of the monomer residues of the MG block containing alginate oligomer are guluronate. Any range formed by any combination of these values may be chosen. Therefore for instance the MG block containing alginate oligomer can have e.g. between 35% and 65%, 40% and 60% or 45% and 55% G residues.

In another embodiment the MG block containing alginate oligomer may have approximately equal amounts of G and M residues (e.g. ratios between 65% G/35% M and 35% G/65% M, for instance 60% G/40% M and 40% G/60% M; 55% G/45% M and 45% G/55% M; 53% G/47% M and 47% G/53% M; 51% G/49% M and 49% G/51% M; e.g. about 50% G and about 50% M) and these residues are arranged predominantly, preferably entirely or as completely as possible, in an alternating MG pattern (e.g. at least 50% or at least 60, 70, 80, 85, 90 or 95% or 100% of the M and G residues are in an alternating MG sequence).

In certain embodiments the terminal uronic acid residues of the oligomers of the invention do not have a double bond, especially a double bond situated between the $C_4$ and $C_5$ atom. Such oligomers may be described as having saturated terminal uronic acid residues. The skilled man would be able to prepare oligomers with saturated terminal uronic acid residues without undue burden. This may be through the use of production techniques which yield such oligomers, or by converting (saturating) oligomers produced by processes that yield oligomers with unsaturated terminal uronic acid residues.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion and acid hydrolysis. In one favoured embodiment acid hydrolysis is used to prepare the alginate oligomers on the invention. In other embodiments enzymic digestion is used with an additional processing step(s) to saturate the terminal uronic acids in the oligomers.

Oligomers may then be separated from the polysaccharide breakdown products chromatographically using an ion exchange resin or by fractionated precipitation or solubilisation or filtration. U.S. Pat. No. 6,121,441 and WO 2008/125828, which are explicitly incorporated by reference herein in their entirety, describe a process suitable for preparing the alginate oligomers of use in the invention. Further information and discussion can be found in for example in "Handbooks of Hydrocolloids", Ed. Phillips and Williams, CRC, Boca Raton, Fla., USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from, but not limited to, *Laminaria hyperbora* and *Lessonia nigrescens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii*.

In embodiments where alginate oligomers which have primary structures in which the majority of the G residues are arranged in G-blocks rather than as single residues are required, algal sources are expected to be most suitable on account of the fact that the alginates produced in these organisms tend to have these structures. The bacterial sources may be more suitable for obtaining alginate oligomers of different structures.

The molecular apparatus involved in alginate biosynthesis in *Pseudomonas fluorescens* and *Azotobacter vinelandii* has been cloned and characterised (WO 94/09124; Ertesvag, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al, Journal of Bacteriology, 2006, Vol 188 (15), 5551-5560) and alginates of tailored primary structures can be readily obtained by manipulating these systems.

The G content of alginates (for example an algal source material) can be increased by epimerisation, for example with mannuronan C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azotobacter vinelandii* AlgE epimerases is described in detail in Ertesvag et al (supra) and Strugala et al (Gums and Stabilisers for the Food Industry, 2004, 12, The Royal Society of Chemistry, 84-94).

To obtain G-block containing alginates or alginate oligomers, epimerisation with one or more *Azotobacter vinelandii* AlgE epimerases other than $AlgE_4$ is preferred as these enzymes are capable of producing G block structures. On the other hand AlgE4 epimerase can be used to create alginates or alginate oligomers with alternating stretches of M/G sequence or primary structures containing single G residue as it has been found that this enzyme seems preferentially to epimerise individual M residues so as to produce single G residues linked to M residues rather than producing G blocks. Particular primary structures can be obtained by using different combinations of these enzymes.

Mutated versions of these enzymes or homologues from other organisms are also specifically contemplated as of use. WO 94/09124 describes recombinant or modified mannuronan C-5 epimerase enzymes (AlgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AlgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure for subsequent alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AlgE genes is disclosed in Gimmestad, M., et al, 2006 (supra). The skilled man would be able to use this teaching to produce new mutants that could be used to give rise to the alginate oligomers of the invention without undue burden.

A further approach is to delete or inactivate the endogenous epimerase genes from an *Azotobacter* or a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer products can be influenced by the culture conditions. It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in a capacity to overcome antibiotic resistance that is substantially lower than that of the unmodified oligomer. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). The skilled man would be aware of still further chemical modifications that can be made to the monosaccharide subunits of oligosaccharides and these can be applied to the alginate oligomers of the invention.

The bacterium targeted by the method of the invention can be any bacterium that is MDR, which according to the present invention means that the bacterium is resistant to at least 3, or at least 4, 5, 6, 7, 8, 9 or 10 antibiotic classes. As noted above antibiotics in different classes are structurally and/or functionally different. In other embodiments the bacterium targeted by the method of the invention can be any bacterium that has extreme drug resistance, which according to the present invention means that the bacterium is resistant to the majority of, or all, antibiotics. In particular, extreme drug resistant bacterium are resistant to at least one antibiotic of last resort (e.g. vancomycin, linezolid, etc.). The skilled man would be aware of examples of antibiotics of last resort Classes of antibiotics and representative constituents thereof include, but are not limited to the aminoglycosides (e.g. amikacin, gentamicin, kanamycin, neomycin, netilmicin, streptomycin, tobramycin); the carbacephems (e.g. loracarbef); the 1st generation cephalosporins (e.g. cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the glycylcyclines (e.g. tigecycline); the carbapenems (e.g. imipenem, meropenem, ertapenem, doripenem, panipenem/betamipron, biapenem, PZ-601); other antibiotics include chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

In preferred embodiments of the invention the MDR bacteria are resistant to three or more antibiotic classes selected from the macrolides, the β-lactams (which may include the carbapenems and/or monobactams and/or carbacephems), the tetracyclines, the polypeptide antibiotics and the quinolones. In other embodiments, the classes may include the aminoglycosides. In still further embodiments the classes may include the macrolides, the β-lactams and the quinolones. It will be noted that invention may result in the overcoming of resistance to one or more classes to which the MDR bacterium is resistant, but it is not necessarily implied that resistance is overcome to all of the classes of antibiotic to which an MDR bacterium may be resistant. Thus for example resistance to a macrolide and/or a β-lactam and/or a quinolone may be overcome in an MDR strain which is also resistant to other antibiotics e.g. aminoglycosides.

More specifically, in these embodiments the antibiotic classes may be selected from the macrolides, the monobactams, the carbapenems, the carbacephems, the 3rd and 4th generation cephalosporins, the tetracyclines, the polypeptide antibiotics and the quinolones. In more particular representative embodiments the bacteria may be resistant to three or more antibiotic classes selected from macrolides, β-lactams, and quinolones e.g. three or more antibiotic classes selected from macrolides, monobactams, carbapenems, carbacephems, 3rd and 4th generation cephalosporins, and quinolones. In other embodiments, the antibiotic classes listed above may also include the aminoglycosides. For example, the antibiotics may be selected from amikacin, gentamicin, kanamycin, neomycin, netilmicin, streptomycin, tobramycin, azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciproftoxacin, enoxacin, gatifloxacin, levofloxacin, lomefloxacin, moxifloxacin, norfloxacin, ofloxacin, and/or trovafloxacin. In particular, the MDR bacteria may be resistant to one or more antibiotics selected from amikacin, tobramycin, ceftazidime, imipenem/cilastatin, meropenem, aztreonam, oxytetracycline, colistin, azithromycin, clarithromycin, dirithromycin, erythromycin, roxithromycin, spiramycin and ciprofloxacin, and it is particularly preferred that the MDR bacteria are resistant to one or more antibiotics selected from ceftazidime, imipenem/cilastatin, meropenem, aztreonam, azithromycin, clarithromycin, dirithromycin, erythromycin, roxithromycin, spiramycin and ciprofloxacin. More preferably the MDR bacteria are resistant to one or more antibiotics selected from aztreonam, azithromycin, clarithromycin, dirithromycin, erythromycin, roxithromycin, spiramycin and ciprofloxacin.

In other embodiments the MDR bacteria are at least resistant to an antibiotic class selected from the β-lactams (e.g. the 1st and 2nd generation cephalosporins and/or monobactams) and the macrolides. Such bacteria may also be resistant to aminoglycosides and/or quinolones (e.g. fluoroquinolones). In other embodiments the MDR bacteria are at least resistant to an antibiotic selected from amikacin, gentamicin, kanamycin, neomycin, netilmicin, streptomycin, tobramycin, cefadroxil, cefazolin, cephalexin, cefaclor, cefamandole, cephalexin, cefoxitin, cefprozil, cefuroxime, azithromycin, clarithromycin, dirithromycin, erythromycin, roxithromycin, telithromycin, CarbomycinA, josamycin, kitasamycin, midecamicine, oleandomycin, spiramycin, troleandomycin and tylosin, or any combination thereof; e.g. amikacin, tobramycin, gentamicin and netilmicin, or any combination thereof.

In a particular embodiment, alginate oligomers may be used according to the present invention to overcome resistance to azithromycin and/or ciprofloxacin, or more generally the antibiotic classes to which they belong, namely macrolides (e.g. azithromycin, clarithromycin, dirithromycin, erythromycin, roxithromycin, telithromycin, CarbomycinA, josamycin, kitasamycin, midecamicine, oleandomycin, spiramycin, troleandomycin, tylosin) and quinolones (e.g. ciprofloxacin, enoxacin, gatifloxacin, levofloxacin, lomefloxacin, moxifloxacin, norfloxacin, ofloxacin, trovafloxacin).

As shown in the Examples below, alginate oligomers have been found to be particularly effective in potentiating the effects of these classes of antibiotics (namely the macrolides and/or quinolones). Additionally, alginate oligomers are particularly effective in potentiating the effects of β-lactam antibiotics, and may also potentiate the effects of other antibiotics. In the cases of the three classes of antibiotics mentioned above, namely macrolides, quinolones and/or β-lactams, alginate oligomers can be seen to have a synergistic effect with the antibiotics. More particularly, the potentiating effect of the alginate oligomers may be seen also with bacteria that are not MDR. Accordingly, more broadly viewed, the invention can be seen to relate to the use of alginate oligomers in conjunction (or combination) with a macrolide, quinolone and/or β-lactam antibiotic, e.g. to combat bacteria, more particularly to treat or combat bacterial infection and/or contamination (i.e. colonisation), or alternatively put for example, to potentiate the effect of the antibiotic. This is discussed in more detail below.

In the context of the "MDR" aspects of the present invention, the alginate oligomers of the invention may be used to overcome resistance in MDR bacteria to one or more of any of the above-mentioned antibiotics and the methods of the invention therefore encompass the use of the alginate oligomers of the invention together with an antibiotic to which an MDR bacterium is resistant to combat that MDR bacterium. In preferred embodiments of the methods of the invention the antibiotic used is an antibiotic selected from the macrolides, the β-lactams, the tetracyclines, and the quinolones. In a further embodiment the polypeptide antibiotics and/or the aminoglycosides may be included. In alternative embodiments the antibiotic does not include an aminoglycoside and/or a polypeptide antibiotic (e.g. colistin). More specifically, in the embodiments set out above, the antibiotic may be selected from the macrolides, the monobactams, the carbapenems, the carbacephems, the 3rd and 4th generation cephalosporins, the tetracyclines, and the quinolones. In more particular representative embodiments the antibiotic may be selected from macrolides, β-lactams, tetracyclines and quinolones e.g. macrolides, monobactams, carbapenems, carbacephems, 3rd and 4th generation cephalosporins, tetracyclines and quinolones. In more particular representative embodiments the antibiotic may be selected from macrolides, β-lactams and quinolones e.g. macrolides, monobactams, carbapenems, carbacephems, 3rd and 4th generation cephalosporins and quinolones. For example, the antibiotic may be selected from amikacin, gentamicin, kanamycin, neomycin, netilmicin, streptomycin, tobramycin, azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin. In particular, the antibiotic may selected from ceftazidime, imipenem/cilastatin, meropenem, aztreonam, oxytetracycline, azithromycin, clarithromycin, dirithromycin, erythromycin, roxithromycin, spiramycin and ciprofloxacin, and it is particularly preferred that the antibiotic is selected from ceftazidime, imipenem/cilastatin, meropenem, aztreonam, azithromycin, clarithromycin, dirithromycin, erythromycin, roxithromycin, spiramycin and ciprofloxacin. More preferably the antibiotic is selected from aztreonam, azithromycin, clarithromycin, dirithromycin, erythromycin, roxithromycin, spiramycin and ciprofloxacin. In other embodiments the antibiotic used is not tobramycin, amikacin and/or colistin. In other embodiments the antibiotic used is not an aminoglycoside or a polypeptide antibiotic. In other embodiments the antibiotic used is not an antibiotic that has a positive charge under the conditions in which it will be used with the alginate oligomer, e.g. antibiotics with at least 3, e.g. at least 4, 5, 6 or 7 amino (—$NH_2$) groups.

As noted above, in more general terms, the alginate oligomers of the invention are effective in potentiating the effects of antibiotics, e.g. any of those discussed above. The alginate oligomers of the invention may thus be used to increase (or improve) the efficacy of antibiotics generally. Particularly good effects have been observed with macrolides, β-lactams, tetracyclines and quinolones e.g. macrolides, monobactams, carbapenems, 3rd and 4th generation cephalosporins, tetracyclines and quinolones; and in particular ceftazidime, imipenem/cilastatin, meropenem, aztreonam, oxytetracycline, azithromycin, clarithromycin, dirithromycin, erythromycin, roxithromycin, spiramycin and ciprofloxacin. The alginate oligomers of the invention may therefore be used to increase (or improve) the efficacy (or effectiveness) of the antibiotics described herein, or more particularly the particularized subgroups thereof, particularly in inhibiting the growth of bacteria, especially MDR bacteria. For example the dose of the antibiotic being used together with the alginate oligomers of the invention may be lowered as a consequence.

With respect to azithromycin, clarithromycin, dirithromycin, erythromycin, roxithromycin and spiramycin (or more generally the macrolides as a class of antibiotics) as noted above, data presented in the Examples show more generally that alginate oligomers may potentiate the effects of these antibiotics (and this class) against a range of different bacteria. Alginate oligomers may thus be used to increase (or improve) the efficacy of these antibiotics (or more generally the antibiotic class of macrolides), for example to enable a lower dose of the antibiotic to be used.

Thus, in another aspect the invention provides a method to improve the efficacy of a macrolide antibiotic, and in particular the effectiveness (or efficacy) of a macrolide antibiotic to inhibit the growth and/or viability of bacteria (which includes inhibition of the growth of a bacterial population, as well as growth of a bacterium), said method comprising using said antibiotic together with (in conjunction or combination with) an alginate oligomer (which may be any alginate oligomer as defined herein). More particularly, the using step may comprise contacting the bacteria with an alginate oligomer at the same or substantially the same time or prior to contacting the bacteria with the macrolide antibiotic. In particular, and in accordance with the disclosures made herein (and specifically the definitions provided herein), which can be read as applying to all aspects of the present invention, the step of contacting the bacterium with the alginate oligomer may include administering the alginate oligomer to a subject. Conveniently the macrolide antibiotic is applied or administered simultaneously with the oligomer or almost immediately before or after the oligomer. However the macrolide antibiotic may be applied or administered at least 1 hour, at least 3 hours, at least 6 hours after the oligomer. In these embodiments the macrolide antibiotic can be applied or administered with or without a further application of an alginate oligomer. The oligomer can be applied or administered in a plurality of applications prior to or with the macrolide antibiotic. Other dosing regimes (e.g. where the antibiotic is administered before the oligomer) are described in more detail above and apply mutatis mutandis to this aspect of the invention.

The macrolide antibiotic may be selected from the group azithromycin, clarithromycin, dirithromycin, erythromycin, roxithromycin, telithromycin, CarbomycinA, josamycin, kitasamycin, midecamicine, oleandomycin, spiramycin, troleandromycin, tylosin. Preferably the macrolide antibiotic is an azalide macrolide, preferably azithromycin. The bacterium can be from any family, genus or species of bacteria (e.g. it may be any of the bacteria discussed and preferred above). Preferably it is an MDR bacterium as defined above. Preferably it is selected from the group *Pseudomonas* (e.g. *Pseudomonas aeruginosa*), *Staphylococcus* (e.g. *Staphylococcus aureus*), *Streptococcus* (e.g. *Streptococcus agalactiae, Streptococcus pneumoniae, Streptococcus pyogenes*), *Haemophilus* (e.g. *Haemophilus ducreyi, Haemophilus influenzae*), *Moraxella* (e.g. *Moraxella catarrhalis*), *Neisseria* (e.g. *Neisseria gonorrhoeae*), *Chlamydia* (e.g. *Chlamydia pneumoniae, Chlamydia trachomatis*), *Mycoplasma* (e.g. *Mycoplasma pneumoniae*), *Helicobacter* (e.g. *Helicobacter pylori*), *Salmonella* (e.g. *Salmonella typhi*) *Burkholderia* (e.g. *Burkholderia cepacia, Burkholderia mallei, Burkholderia pseudomallei*), *Acinetobacter* (e.g. *Acinetobacter baumannii, Acinetobacter lwoffi*), *Providencia* (e.g. *Providencia stuartii, Providencia rettgeri, Providencia alcalifaciens*), and *Klebsiella* (e.g. *Klebsiella oxytoca*).

The location of the bacterium or population is not restricted (e.g. it may be any of the locations discussed and preferred below). In one embodiment the bacterium or population will not be in a biofilm. In one embodiment the bacterium or population will be in a biofilm. Thus, the method may be an in vitro or an in vivo method. In the latter instance the method can be viewed as a method for the treatment of a bacterial infection in a subject (e.g. those bacterial infections and subjects described and preferred above or elsewhere herein), said method comprising administering to a subject a pharmaceutically effective amount of an alginate oligomer at substantially the same time as or prior to administering a pharmaceutically effective amount of a macrolide antibiotic.

Thus the invention provides an alginate oligomer for use together with (or in combination or conjunction with) a macrolide antibiotic for the treatment of a bacterial infection in a subject. "Use together" is as defined above.

Alternatively put; the invention provides the use of an alginate oligomer for the manufacture of a medicament for use together with a macrolide antibiotic in the treatment of a bacterial infection in a subject. The medicament may further comprise the macrolide antibiotic.

The medicament may be in the form of a single composition or formulation comprising the alginate oligomer and macrolide antibiotic(s) or separate compositions or formulations may be prepared and used, each containing the alginate oligomer or the macrolide antibiotic(s), respectively.

Thus in a more particular aspect the present invention provides the use of an alginate oligomer and at least one macrolide antibiotic for the manufacture of a medicament for use in the treatment of a bacterial infection in a subject.

Thus a further aspect of the present invention provides a product containing an alginate oligomer and a macrolide antibiotic (or one or more macrolide antibiotics) as a combined preparation for separate, simultaneous or sequential use in the treatment of a bacterial infection in a subject.

As noted above, in these aspects of the invention the alginate oligomer may improve the efficacy of the antibiotic, and in particular the efficacy (or effectiveness) of the antibiotic in inhibiting bacterial growth.

Improving the efficacy of the antibiotic includes any aspect of improving or enhancing the effect of the antibiotic, e.g. so that the anti-bacterial effect of the antibiotic is increased or enhanced in any way over the effect of the antibiotic seen in the absence of the alginate oligomer. This may be seen for example in a stronger effect of the antibiotic in inhibiting growth of the bacteria, requiring less antibiotic to achieve the same effect seen in the absence of alginate oligomer, or a increased effectiveness seen as increased speed or rate of action, an inhibitory effect being seen in less time than in the absence of oligomer.

The references to "improving the effectiveness of a macrolide antibiotic to inhibit the growth and/or viability of bacteria" etc. accordingly may include that the alginate oligomer renders the macrolide antibiotic, at least twice as, or at least four times, at least eight times, at least sixteen times or at least thirty two times more effective at inhibiting bacterial growth (e.g. acting as a bacteriostatic agent). Put in a different way, the oligomer may at least double, at least quadruple, at least octuple, at least sexdecuple or at least duotrigenuple the effectiveness of the macrolide antibiotic to inhibit growth of the bacteria. The inhibitory effect of the macrolide antibiotic can be measured by assessing the Minimum Inhibitory Concentration (MIC), i.e. that concentration of macrolide antibiotic that completely inhibits growth of the bacteria. A halving of the MIC corresponds to a doubling in the inhibitory effect of the macrolide antibiotic. A quartering of the MIC corresponds to a quadrupling of the inhibitory effect.

This aspect also allows the concentration of the macrolide antibiotic administered to a subject or applied to a location to be reduced whilst maintaining the same effectiveness. This can be beneficial if the macrolide antibiotic is expensive or associated with side effects. Minimising the use of antibiotics is also desirable to minimise development of resistance. In accordance with the invention the use of an alginate oligomer as described above, i.e. at the same or substantially the same time or prior to administering the macrolide antibiotic permits the antibiotic to be used at a concentration that is less than 50%, less than 25%, less than 10% or less than 5% of the amount normally administered/applied to achieve a particular level of inhibition of the growth of bacteria in the absence of the alginate oligomer.

In this aspect the alginate oligomers may be any of those discussed and in particular those stated as preferred above and the alginate oligomers will be applied to the bacteria and/or their location at a local concentration of at least 2%, at least 4%, at least 6%, at least 8% or at least 10% weight by volume.

Alginate oligomers may similarly potentiate the effects of ciprofloxacin (and the quinolones as a class of antibiotics) and aztreonam (and the β-lactams, e.g. the monobactams as a class of antibiotics), and may thus be used to increase (or improve) the efficacy of these antibiotics (or more generally the antibiotic classes of quinolones and β-lactams, e.g. the monobactams), for example to enable a lower dose of these antibiotics to be used. Accordingly, alginate oligomers may be used analogously to as described above for macrolide antibiotics to increase the efficacy of these antibiotics and the statements made above in the context of macrolides apply analogously to the quinolone and/or β-lactam antibiotic classes also.

In the context of the "MDR" aspects of the invention, in other embodiments the MDR bacterium targeted by the method of the invention is a bacterium which is resistant to at least one antibiotic that is a conventional or standard (e.g. clinically approved) treatment for (or against) that bacterium. The skilled man would be aware of the conventional and recommended antibiotics for the treatment of any particular bacterial infection or disease. Factors that dictate what is a conventional treatment are well known to the skilled man and include the nature and location of the bacterium, the intrinsic susceptibility of the bacterium, the necessary route of administration and the consequent pharmacokinetics of the antibiotics. Typically an antibiotic which is a conventional treatment for a bacterium will be an antibiotic to which a reference (i.e. typical or wild type) bacterium of that species displays no intrinsic resistance in vitro and/or in the clinical setting. As discussed below, the skilled man would be able to employ routine assays to determine this information for any antibiotic or bacterium he could not obtain standard information for from the literature or his common general knowledge.

Alternatively defined, in certain embodiments the MDR bacterium targeted in accordance with the invention is a bacterium which has acquired (developed) some or all of its antibiotic resistance. Particularly such antibiotic resistance is acquired in a clinical setting. Particular strains of bacteria which have acquired multiple antibiotic resistance are sometimes termed MDR strains as their resistant phenotype differs from that of a corresponding strain (e.g. the wild-type strain or a "typical" strain) which has not acquired multidrug resistance, but demonstrates only the innate or intrinsic resistance which is typical of the species. Therefore, in particularly preferred embodiments the bacterium targeted by the invention is a bacterium from an MDR strain of a species of bacteria (e.g. a strain known or identified in the art as MDR). In these embodiments the MDR bacterium (e.g. bacterium from an MDR strain of bacteria) targeted by the method of the invention has acquired or developed resistance to at least 1, e.g. at least 2, 3, 4, 5, 6, 7, 8, 9 or 10 structurally and/or functionally different antibiotics or antibiotic classes. In some cases, all of the antibiotic resistance of the bacterium (e.g. bacterium from an MDR strain of bacteria) is acquired or developed and none of the resistance is intrinsic, but as noted above, it is not necessarily the case that an MDR phenotype is acquired, and the MDR bacterium which is treated according to the present invention may be MDR intrinsically (or innately).

The MDR bacterium targeted according to the invention can be selected from any genera or species of bacteria. Examples of genera or species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria,*

*Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*; e.g. gram-positive bacteria such as, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes, Clostridium tetani, Clostridium perfringens, Clostridium botulinum*, and *Enterococcus* species and Gram-negative bacteria such as *Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Coxiella burnetti, Escherichia coli, Neiserria meningitidis, Neiserria gonorrhea, Haemophilus influenzae, Haemophilus ducreyi, Yersinia pestis, Yersinia enterolitica, Escherichia hirae, Burkholderia cepacia, Burkholderia mallei, Burkholderia pseudomallei, Francisella tularensis, Bacteroides fragilis, Fusobascterium nucleatum, Cowdria ruminantium, Moraxella catarrhalis, Klebsiella pneumoniae, Proteus mirabilis, Enterobacter cloacae, Serratia marcescens, Helicobacter pylori, Salmonella enteritidis, Salmonella typhi* and *Acinetobacter baumannii, Acinetobacter lwoffi, Providencia stuartii, Providencia rettgeri, Providencia alcalifaciens* and *Klebsiella oxytoca* and Gram non-responsive bacteria such as *Chlamydia trachomatis, Chlamydia psittaci.*

Preferably the MDR bacterium targeted according to the invention is selected from the following genera: *Achromobacter, Acinetobacter, Actinobacillus, Aeromonas, Agrobacterium, Alcaligenes, Alteromonas, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces, Treponem* and *Yersinia*

As noted above, the invention includes both medical and non-medical uses and hence the bacteria which may be treated or combatted according to the present invention include not only clinically-relevant strains, but any bacteria which may present a problem of colonisation or contamination. In certain aspects clinically-relevant genera, species or strains of bacteria are preferred.

In certain embodiments the MDR bacterium is selected from the genera, *Acinetobacter, Klebsiella, Providencia, Pseudomonas* and *Burkholderia*, e.g. the bacterium is from a species selected from *Acinetobacter baumannii, Acinetobacter baylyi, Acinetobacter bouvetii, Acinetobacter calcoaceticus, Acinetobacter gerneri, Acinetobacter grimontii, Acinetobacter haemolyticus, Acinetobacter johnsonii, Acinetobacter junii, Acinetobacter lwoffii, Acinetobacter parvus, Acinetobacter radioresistens, Acinetobacter schindleri, Acinetobacter tandoii, Acinetobacter tjernbergiae, Acinetobacter towneri, Acinetobacter ursingii, Klebsiella granulomatis, Klebsiella oxytoca, Klebsiella pneumoniae, Klebsiella singaporensis, Klebsiella variicola, Providencia stuartii, Providencia sneebia, Providencia rettgeri, Providencia rustigianii, Providencia heimbachae, Providencia burhodogranariea, Providencia alcalifaciens, Pseudomonas aeruginosa, Pseudomonas alcaligenes, Pseudomonas anguilliseptica, Pseudomonas argentinensis, Pseudomonas borbori, Pseudomonas citronellolis, Pseudomonas flavescens, Pseudomonas mendocina, Pseudomonas nitroreducens, Pseudomonas oleovorans, Pseudomonas pseudoalcaligenes, Pseudomonas resinovorans, Pseudomonas straminea, Pseudomonas cremoricolorata, Pseudomonas fulva, Pseudomonas monteilii, Pseudomonas mosselii, Pseudomonas oryzihabitans, Pseudomonas parafulva, Pseudomonas plecoglossicida, Pseudomonas putida, Pseudomonas balearica, Pseudomonas luteola, and Pseudomonas stutzeri, Burkholderia ambifaria, Burkholderia andropogonis, Burkholderia anthina, Burkholderia brasilensis, Burkholderia calcdonica, Burkholderia caribensis, Burkholderia caryophylli, Burkholderia cenocepacia, Burkholderia cepacia, Burkholderia dolosa, Burkholderia fungorum, Burkholderia gladioli, Burkholderia glathei, Burkholderia glumae, Burkholderia graminis, Burkholderia hospita, Burkholderia kururiensis, Burkholderia mallei, Burkholderia multivorans, Burkholderia phenazinium, Burkholderia phenoliruptrix, Burkholderia phymatum, Burkholderia phytofirmans, Burkholderia plantarii, Burkholderia pseudomallei, Burkholderia pyrrocinia, Burkholderia sacchari, Burkholderia singaporensis, Burkholderia sordidicola, Burkholderia stabilis, Burkholderia terricola, Burkholderia thailandensis, Burkholderia tropica, Burkholderia tuberum, Burkholderia ubonensis, Burkholderia unamae, Burkholderia vietnamiensis*, and *Burkholderia xenovorans*. The *Burkholderia* species are of particular note, especially *Burkholderia cepacia, Burkholderia pseudomallei* and *Burkholderia mallei*; e.g. *Burkholderia cepacia.*

Thus, the invention may be used against Gram positive or Gram negative bacteria, or indeed Gram-indeterminate bacteria. Gram-negative bacteria, for instance those particularized above, are of importance. Within the Gram-negative bacteria the Enterobacteriaceae and the Gram-negative bacteria non-fermenting bacteria are of particular note.

Enterobacteriaceae include, but are not limited to, bacteria from the genera *Alishewanella, Alterococcus, Aquamonas, Aranicola, Azotivirga, Brenneria, Budvicia, Buttiauxefia, Cedecea, Citrobacter, Cronobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pec-*

*tobacterium, Phlomobacter, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia, Yokenella*. Preferred genera of Enterobacteriaceae include *Escherichia, Klebsiella, Salmonella, Shigella, Yersinia* and *Providencia*.

Non-fermenting Gram-negative bacteria include, but are not limited to, bacteria from the genera *Pseudomonas, Acinetobacter, Stenotrophomonas* and *Burkholderia, Achromobacter, Algaligenes, Bordetella, Brevundimonas, Comamonas, Elizabethkingia* (formerly *Chryseobacterium*), *Methylobacterium, Moraxella, Ochrobactrum, Oligella, Psychrobacter, Ralstonia, Roseomonas, Shewanella, Sphingobacterium*, e.g. *Pseudomonas aeruginosa, Acinetobacter baumannii, Stenotrophomonas maltophilia*, and *Burkholderia* spp.

Preferably the bacteria may be selected from the genera *Pseudomonas, Acinetobacter, Stenotrophomonas, Burkholderia, Escherichia, Klebsiella, Providencia, Streptococcus, Staphylococcus*, e.g. *Pseudomonas aeruginosa, Acinetobacter baumannii, Stenotrophomonas maltophilia, Burkholderia* spp, *E. coli, Klebsiella pneumoniae* and *Burkholderia cepacia, Burkholderia mallei, Burkholderia pseudomallei, Acinetobacter lwoffi, Providencia stuartii, Providencia rettgeri, Providencia alcalifaciens, Klebsiella oxytoca, Pseudomonas anguilliseptica, Pseudomonas oryzihabitans, Pseudomonas plecoglossicida, Pseudomonas luteola*, and MRSA.

Results presented in the Examples below show particularly that alginate oligomers may be used together with various antibiotics against MDR strains of *Pseudomonas* and particularly MDR strains of *P. aeruginosa*. The results also show that alginate oligomers may effectively be used with various antibiotics against *Acinetobacter* species, and particularly *A. baumannii* and *A. lwoffii*; against *Burkholderia* species, and particularly *B. cepacia*; against *Providencia* species, and particularly *P. stuartii*; against *Klebsiella* species, and particularly *Klebsiella pneumonia*; against *Streptococcus*, and particularly *Streptococcus oralis*; against *Staphylococcus*, and in particular MRSA; against *Escherichia*, and particularly *Escherichia coli*, and that resistance to antibiotics in these genera/species may be overcome.

In this regard, the data more generally show that alginate oligomers may be particularly effective in potentiating (or improving/increasing the efficacy of) the effects of antibiotics against *Acinetobacter* species, and particularly *A. baumannii* and *Burkholderia* species, and particularly *B. cepacia*. This leads to the proposal that in one aspect the invention can be seen more generally to relate to use of alginate oligomers in conjunction (or combination) with an antibiotic to combat (or to inhibit the growth and/or viability of) *Acinetobacter* and/or *Burkholderia* (i.e. *Acinetobacter* and/or *Burkholderia* species in general), for example to treat or combat infection and/or contamination (i.e. colonisation) with these bacteria.

In certain aspects, the bacterium targeted by the invention may alternatively be viewed as a clinically relevant bacterium, e.g. a bacterium that is known to be associated with disease and/or infection in subjects; especially diseases and infections that are unresponsive to at least 3 structurally and/or functionally different antibiotics, or at least 3 antibiotic classes, more particularly at least 4, 5, 6, 7 8, 9 or 10 structurally and/or functionally different antibiotics or antibiotic classes conventionally used in the treatment of that disease and/or infection. More particularly, the bacterium targeted by the invention may be from a clinically relevant MDR strain of bacteria. The bacterium may cause or result in clinically significant or clinically important infections, in other words infections which are the cause of significant clinical problems. For instance, the bacterium could be a bacterium associated with nosocomial infections, infections in the respiratory tract of patients, e.g. patients suffering from cystic fibrosis, chronic obstructive pulmonary disease, congestive obstructive airway disease/congestive obstructive airway pneumonia (COAD/COAP), pneumonia, emphysema, bronchitis and sinusitis; infections in chronic wounds (including burns), device related infections associated with implantable or prosthetic medical devices e.g. prosthetic valve endocarditis or infection of lines or catheters or artificial joints or tissue replacements or endotracheal or tracheotomy tubes. Examples of these types of bacteria include *Pseudomonas aeruginosa, Acinetobacter baumannii, Stenotrophomonas maltophilia, Burkholderia* spp (e.g. *B. cepacia*), *E. coli, Klebsiella pneumoniae, Staphylococcus aureus, Methicillin Resistant Staphylococcus aureus* (MRSA), *Clostridium difficile, Mycobacterium tuberculosis, Enterococcus* and Vancomycin-Resistant *Enterococcus* and *Providencia stuartii*.

The bacterium targeted by the method of the invention may be the same as a bacterium that has previously been isolated from a subject. Thus, the bacterium is preferably a clinical strain or a clinical isolate. The bacterium targeted by the method of the invention may be present in or on a subject. The bacterium may be known or found to be MDR, or the bacterium may have developed MDR during the subject's treatment. In view of the requirement for MDR (or MDR status), which may or may not be or include acquired resistance, the bacterium to be treated according to the present invention will generally not be a conventional laboratory or reference strain, e.g. a strain such as *Pseudomonas aeruginosa* PA01 (ATCC 15692) or *Staphylococcus aureus* ATCC 6538. In another embodiment the bacterium will not be MRSA (methicillin resistant *Staphylococcus aureus*), e.g. strain 1103.

In representative embodiments the bacterium may be an MDR strain of *Pseudomonas aeruginosa* that is resistant to one or more antibiotics selected from the penicillins, cephalosporins, carbapenems, monobactams, aminoglycosides, fluoroquinolones, macrolides or polypeptides (e.g. polymyxins), more particularly cephalosporins, carbapenems, monobactams, aminoglycosides, fluoroquinolones, or macrolides, e.g. amikacin, ciprofloxacin, gentamicin, tobramycin, piperacillin, ticarcillin, colistin, oxytetracycline, meropenem, ceftazidime, aztreonam, azithromycin, clarithromycin, dirithromycin, erythromycin, roxithromycin, spiramycin and imipenem/cilastatin; particularly ciprofloxacin, colistin, oxytetracycline, meropenem, ceftazidime, aztreonam, azithromycin, clarithromycin, dirithromycin, erythromycin, roxithromycin, spiramycin and imipenem/cilastatin, and especially ciprofloxacin, meropenem, ceftazidime, aztreonam, azithromycin, clarithromycin, dirithromycin, erythromycin, roxithromycin, spiramycin and imipenem/cilastatin, e.g. aztreonam, ciprofloxacin, azithromycin, clarithromycin, dirithromycin, erythromycin, roxithromycin and spiramycin.

In other embodiments the bacterium may be an MDR strain of *Klebsiella pneumoniae* that is resistant to one or more antibiotics selected from the penicillins, cephalosporins, carbapenems, monobactams, aminoglycosides, fluoroquinolones, macrolides or polypeptides (e.g. polymyxins) e.g. cefotaxime, ceftriaxone, amikacin, gentamicin, ciprofloxacin, tobramycin, ampicillin, piperacillin, ticarcillin, colistin, meropenem, ceftazidime, aztreonam, azithromycin, clarithromycin, dirithromycin, erythromycin, roxithromycin, spiramycin, imipenem/cilastatin; cefepime, levofloxacin, norfloxacin, gatifloxacin, moxifloxacin, and ertapenem, particularly ciprofloxacin, colistin, meropenem, ceftazidime, aztreonam, azithromycin, clarithromycin, dirithromycin, erythromycin, roxithromycin, spiramycin and imipenem/cilastatin, and especially ciprofloxacin, meropenem, ceftazidime, aztreonam, azithromycin and imipenem/cilastatin, e.g. aztreonam, ciprofloxacin, azithromycin, clarithromycin, dirithromycin, erythromycin, roxithromycin and spiramycin.

In other embodiments the bacterium may be an MDR strain of *Acinetobacter baumannii* that is resistant to one or more antibiotics selected from the penicillins, cephalosporins, carbapenems, monobactams, glycylcyclines, aminoglycosides, fluoroquinolones, macrolides or polypeptides (e.g. polymyxins). e.g. imipenem/cilastatin, ampicillin, cefepime, colistin, rifampin, tigecycline, amikacin, ciprofloxacin, meropenem, ceftazidime, aztreonam, azithromycin, clarithromycin, dirithromycin, erythromycin, roxithromycin, spiramycin and imipenem/cilastatin; particularly colistin, ciprofloxacin, meropenem, ceftazidime, aztreonam, azithromycin, clarithromycin, dirithromycin, erythromycin, roxithromycin, spiramycin and imipenem/cilastatin, and especially ciprofloxacin, meropenem, ceftazidime, aztreonam, azithromycin, clarithromycin, dirithromycin, erythromycin, roxithromycin, spiramycin and imipenem/cilastatin, e.g. aztreonam, ciprofloxacin, azithromycin, clarithromycin, dirithromycin, erythromycin, roxithromycin and spiramycin.

In other embodiments the bacterium may be an MDR strain of *Providencia stuartii* that is resistant to one or more antibiotics selected from the penicillins, cephalosporins, carbapenems, monobactams, aminoglycosides, fluoroquinolones, macrolides or polypeptides (e.g. polymyxins) e.g. cefotaxime, ceftriaxone, amikacin, gentamicin, ciprofloxacin, tobramycin, ampicillin, piperacillin, ticarcillin, colistin, meropenem, ceftazidime, aztreonam, azithromycin, clarithromycin, dirithromycin, erythromycin, roxithromycin, spiramycin, imipenem/cilastatin; cefepime, levofloxacin, norfloxacin, gatifloxacin, moxifloxacin, and ertapenem, particularly ciprofloxacin, colistin, ciprofloxacin, meropenem, ceftazidime, aztreonam, azithromycin, clarithromycin, dirithromycin, erythromycin, roxithromycin, spiramycin and imipenem/cilastatin, and especially ciprofloxacin, meropenem, ceftazidime, aztreonam, azithromycin and imipenem/cilastatin, e.g. aztreonam, ciprofloxacin, azithromycin, clarithromycin, dirithromycin, erythromycin, roxithromycin and spiramycin.

In other embodiments the bacterium may be an MDR strain of *Burkholderia cepacia* that is resistant to one or more antibiotics selected from the penicillins, cephalosporins, carbapenems, monobactams, aminoglycosides, fluoroquinolones, macrolides or polypeptides (e.g. polymyxins) e.g. cefotaxime, ceftriaxone, amikacin, gentamicin, ciprofloxacin, tobramycin, ampicillin, piperacillin, ticarcillin, colistin, meropenem, ceftazidime, aztreonam, azithromycin, clarithromycin, dirithromycin, erythromycin, roxithromycin, spiramycin, imipenem/cilastatin; cefepime, levofloxacin, norfloxacin, gatifloxacin, moxifloxacin, and ertapenem, particularly ciprofloxacin, colistin, ciprofloxacin, meropenem, ceftazidime, aztreonam, azithromycin, clarithromycin, dirithromycin, erythromycin, roxithromycin, spiramycin and imipenem/cilastatin, and especially ciprofloxacin, meropenem, ceftazidime, aztreonam, azithromycin and imipenem/cilastatin, e.g. aztreonam, ciprofloxacin, azithromycin, clarithromycin, dirithromycin, erythromycin, roxithromycin and spiramycin.

The data of the Examples surprisingly shows that the alginate oligomers of the invention are particularly effective in enhancing the effects (increasing the effectiveness (or efficacy)) of antibiotics against bacteria of the genus *Burkholderia*. As discussed above, *Burkholderia* represent an important genus of bacteria since they can cause disease in humans and animals and they display intrinsic resistance to multiple classes of antibiotics (e.g. the aminoglycosides, the β lactams and/or the macrolides). *Burkholderia* organisms, especially *Burkholderia cepacia, Burkholderia pseudomallei* and *Burkholderia mallei* are therefore considered to be MDR bacteria naturally on account of the intrinsic resistance exhibited as their natural phenotype. Of course, strains of *Burkholderia* species can acquire additional resistance phenotypes. Accordingly, treatments for *Burkholderia* species that enhance the effects of antibiotics against such species are in high demand.

Thus, it is a preferred embodiment of the invention that the target bacterium is a *Burkholderia* organism, e.g. selected from *Burkholderia ambifaria, Burkholderia andropogonis, Burkholderia anthina, Burkholderia brasilensis, Burkholderia calcdonica, Burkholderia caribensis, Burkholderia caryophylli, Burkholderia cenocepacia, Burkholderia cepacia, Burkholderia dolosa, Burkholderia fungorum, Burkholderia gladioli, Burkholderia glathei, Burkholderia glumae, Burkholderia graminis, Burkholderia hospita, Burkholderia kururiensis, Burkholderia mallei, Burkholderia multivorans, Burkholderia phenazinium, Burkholderia phenoliruptrix, Burkholderia phymatum, Burkholderia phytofirmans, Burkholderia plantarii, Burkholderia pseudomallei, Burkholderia pyrrocinia, Burkholderia sacchari, Burkholderia singaporensis, Burkholderia sordidicola, Burkholderia stabilis, Burkholderia terricola, Burkholderia thailandensis, Burkholderia tropica, Burkholderia tuberum, Burkholderia ubonensis, Burkholderia unamae, Burkholderia vietnamiensis*, and *Burkholderia xenovorans*, in particular *Burkholderia cepacia, Burkholderia mallei* and *Burkholderia pseudomallei* and especially *Burkholderia cepacia.*

More generally, the use of alginate oligomers to combat *Burkholderia* (e.g. to treat or combat *Burkholderia* infection and/or contamination (i.e. colonisation)), or to increase (or improve) the efficacy of an antibiotic against *Burkholderia* represents a particular preferred and separate aspect of this invention.

Accordingly, in another aspect the invention provides a method to improve the efficacy of an antibiotic, and in particular the effectiveness (or efficacy) of an antibiotic to inhibit the growth and/or viability of a *Burkholderia* organism (which includes inhibition of the growth of a *Burkholderia* population, as well as growth of a *Burkholderia* organism), said method comprising using said antibiotic together with (in conjunction or combination with) an alginate oligomer (which may be any alginate oligomer as defined herein and especially those indicated already as being preferred; e.g. the "high G", "high M", "G-block" and "M-block" oligomers). The oligomers of use in this aspect may especially be those with the sizes, size ranges and molecular weight distributions stated as preferred above. The discussion of preferred alginate oligomers of the invention applies mutatis mutandis to this aspect of the invention.

More particularly, the using step may comprise contacting the *Burkholderia* organism with an alginate oligomer at the same or substantially the same time or prior to contacting the *Burkholderia* organism with the antibiotic. In particular, and in accordance with the disclosures made above (and specifically the definitions provided herein), which can be read as applying to all aspects of the present invention, the step of contacting the bacterium with the alginate oligomer may include administering the alginate oligomer and the antibiotic to a subject.

The antibiotic may be selected from any antibiotic disclosed above. Preferred antibiotics may be selected from the β-lactams (e.g. the carbecephems (e.g. loracarbef); the 1st generation cephalosporins (e.g. cefadroxil, cefazolin, cephalexin; 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin) the carbapenems (e.g. imipenem, meropenem, ertapenem, doripenem, panipenem/betamipron, biapenem, PZ-601)); the macrolides (e.g. azithromycin, clarithromycin, dirithromycin, erythromycin, troleandomycin); the quinolones (e.g. ciprofloxacin, enoxacin, gatifloxacin, levofloxacin, lomefloxacin, moxifloxacin, norfloxacin, ofloxacin, trovafloxacin); and the tetracyclines (e.g. demeclocycline, doxycycline, minocycline, oxytetracycline, tetracycline).

More preferably the antibiotic is selected from azithromycin, clarithromycin, dirithromycin, erythromycin, roxithromycin, telithromycin, CarbomycinA, josamycin, kitasamycin, midecamicine, oleandomycin, spiramycin, troleandromycin, tylosin, cefixime, cefdinir, cefditoren, cefoperazone, cefotaxime, cefpodoxime, ceftazidime, ceftibuten, ceftizoxime, ceftriaxone, cefepime, aztreonam, imipenem, meropenem, ertapenem, doripenem, panipenem/betamipron, biapenem, PZ-601, ciprofloxacin, enoxacin, gatifloxacin, levofloxacin, lomefloxacin, moxifloxacin, norfloxacin, ofloxacin, trovafloxacin demeclocycline, doxycycline, minocycline, oxytetracycline and tetracycline, e.g. aztreonam, ciprofloxacin, azithromycin, clarithromycin, dirithromycin, erythromycin, roxithromycin, spiramycin, oxytetracycline, ceftazidime and imipenem. In particularly preferred embodiments the antibiotic is selected from aztreonam, ceftazidime, azithromycin, clarithromycin and erythromycin In other embodiments the antibiotic used is not tobramycin, amikacin and/or colistin. In other embodiments the antibiotic used is not an aminoglycoside or a polypeptide antibiotic. In other embodiments the antibiotic used is not an antibiotic that has a positive charge under the conditions in which it will be used with the alginate oligomer, e.g. antibiotics with at least 3, e.g. at least 4, 5, 6 or 7 amino (—NH$_2$) groups.

The *Burkholderia* organism can be from any *Burkholderia* species, e.g. any of those disclosed herein, in particular the *Burkholderia* organism will be *Burkholderia cepacia*, *Burkholderia mallei* or *Burkholderia pseudomallei*, especially *Burkholderia cepacia*. In certain embodiments the *Burkholderia* organism is resistant to the antibiotic.

In one embodiment the *Burkholderia* organism or population thereof will not be in a biofilm or in the process of forming a biofilm. In another embodiment the *Burkholderia* organism or population thereof will be in a biofilm.

The method may be an in vitro or an in vivo method and may have non-medical and medical applications. In the latter instance the method can be viewed as a method for the treatment of a *Burkholderia* infection (e.g. a *Burkholderia cepacia, Burkholderia mallei* or *Burkholderia pseudomallei* infection) in a subject (e.g. those subjects described and preferred herein), said method comprising administering to a subject a pharmaceutically effective amount of an alginate oligomer together with a pharmaceutically effective amount of an antibiotic. This embodiment extends to any and all of the medical uses, diseases and locations of infection described herein when involving *Burkholderia* organisms.

Thus the invention provides an alginate oligomer for use together with (or in combination or conjunction with) an antibiotic for the treatment or prevention of a *Burkholderia* infection in a subject. The subject may be infected, suspected to be infected, or at risk of infection with *Burkholderia*. The *Burkholderia* may be of any species mentioned herein. The term "use together" should be interpreted as discussed above.

Alternatively put, the invention provides the use of an alginate oligomer for the manufacture of a medicament for use together with an antibiotic in the treatment of a *Burkholderia* infection in a subject. The medicament may further comprise the antibiotic.

The medicament may be in the form of a single composition or formulation comprising the alginate oligomer and antibiotic(s) or separate compositions or formulations may be prepared and used, each containing the alginate oligomer or the antibiotic(s), respectively.

Thus in a more particular aspect the present invention provides the use of an alginate oligomer and at least one antibiotic for the manufacture of a medicament for use in the treatment of a *Burkholderia* infection in a subject.

Thus a further aspect of the present invention provides a product containing an alginate oligomer and an antibiotic (or antibiotics) as a combined preparation for separate, simultaneous or sequential use in the treatment of a *Burkholderia* infection in a subject.

In a further embodiment of this aspect of the invention there is provided a method for combating contamination of a site with a *Burkholderia* organism, said method comprising contacting the site and/or the *Burkholderia* organism with (an effective amount of) an alginate oligomer together with (an effective amount of) at least one antibiotic. Such a method may particularly be an in vitro method, and the site may be any surface or location discussed herein.

As noted above, in these aspects of the invention the alginate oligomer may improve the efficacy of the antibiotic, and in particular the efficacy (or effectiveness) of the antibiotic in inhibiting the growth of the *Burkholderia* organism.

The references to "improving the effectiveness of an antibiotic to inhibit the growth and/or viability of a *Burkholderia* organism" should be construed in accordance with preceding discussion of what is meant by "improving the effectiveness of a macrolide antibiotic to inhibit the growth and/or viability of bacteria".

This aspect also allows the concentration of the antibiotic administered to a subject or applied to a location in order to combat a *Burkholderia* organism to be reduced whilst maintaining the same effectiveness. This can be beneficial if the antibiotic is expensive or associated with side effects. Minimising the use of antibiotics is also desirable to minimise development of resistance. In accordance with the invention the use of an alginate oligomer together with an antibiotic permits the antibiotic to be used at a concentration that is less than 50%, less than 25%, less than 10% or less than 5% of the amount normally administered/applied to achieve a particular level of inhibition of the growth of a *Burkholderia* organism in the absence of the alginate oligomer.

In this aspect the alginate oligomers may be any of those discussed and in particular those stated as preferred above and the alginate oligomers will be applied to the *Burkholderia* organism and/or their location at a local concentration of at least 2%, at least 4%, at least 6%, at least 8% or at least 10% weight by volume.

Although in certain aspects of the invention as discussed above, the bacterium may be *Acinetobacter*, in certain particular embodiments the MDR bacterium targeted by the methods of the invention is not *Acinetobacter baumannii*, or any *Acinetobacter* species. In another embodiment the antibiotic used against the *Acinetobacter baumannii*, or any *Acinetobacter* species, is not azithromycin, or any macrolide.

By "resistant to an antibiotic" it is meant that the bacterium displays a substantially greater tolerance (reduced susceptibility) to an antibiotic as compared to a reference bacterium sensitive to the antibiotic or a typical, or a wild type, version of the bacterium. Such a substantially greater tolerance may be a statistically significant decrease in susceptibility to the antibiotic, as measured for example in standard assays, such as MIC assays. In some cases, a bacterium can be completely unaffected by exposure to an antibiotic. In this instance the bacterium can be considered fully resistant to that antibiotic.

A suitable reference bacterium is Oxford *Staphylococcus aureus* (NCTC 6571) although many others are known in the art and are readily available. Typical, or wild type, versions of a bacterium can be obtained easily from laboratories and culture collections throughout the world.

Susceptibility (and conversely resistance and tolerance) to antibiotic can be measured in any convenient way, e.g. with dilution susceptibility tests and/or disk diffusion tests. The skilled man would appreciate that the extent of the difference in tolerance/susceptibility sufficient to constitute resistance will vary depending on the antibiotic and organism under test and the test used However, a resistant bacterium will preferably be at least twice, e.g. at least 3, 4, 5, 6, 10, 20, or 50 times as tolerant to the antibiotic as the reference bacterium sensitive to the antibiotic or a typical or a wild type version of the bacterium. Preferably resistance of a particular bacteria to an antibiotic is determined using bacteria which are not in a biofilm or which do not have a biofilm phenotype.

The minimum inhibitory concentration (MIC) assay (Jorgensen et al., Manual of Clinical Microbiology, 7th ed. Washington, D.C.: American Society for Microbiology, 1999; 1526-43) is a convenient dilution susceptibility test to use. This assay measures the relevant tolerance of a bacterium to antibiotics by determining the lowest concentration of antibiotic that causes complete inhibition of growth. A bacterium resistant to an antibiotic will have a substantially greater MIC value for the antibiotic than that of the reference bacterium sensitive to the antibiotic or a typical, or a wild type, version of the bacterium, e.g. the resistant bacteria will have a MIC value for the antibiotic that is at least twice or at least four times, at least eight times, at least sixteen times, at least thirty two times or at least sixty four times higher. Put in a different way, the MIC value of the resistant bacterium for the antibiotic may be at least double, at least quadruple, at least octuple, at least sexdecuple or at least duotrigenuple the MIC value of the reference bacterium sensitive to the antibiotic or a typical or a wild type version of the bacterium.

Viewed alternatively, and in the context of an in vivo bacterium and/or the treatment of a bacterial infection that is resistant to multiple antibiotic classes, a bacterium may be considered resistant to an antibiotic if the bacterium has a MIC value for the antibiotic that is greater than then maximum safe circulating concentration of the antibiotic in the subject (which may be determined easily by the skilled man). More functionally, a bacterium is resistant to an antibiotic if an infection associated with that bacterium is unresponsive (i.e. there is no change in the clinical indicia of the infection) to the maximum safe dose of the antibiotic.

"Overcoming resistance" should be construed accordingly as a measurable reduction in the above-described indicators of the resistance (or measurable increase in susceptibility or measurable decrease in tolerance) to the antibiotic displayed by the bacterium. Therefore "overcoming resistance" can alternatively be expressed as "reducing resistance". It is a reference to the observed phenotype of the target bacterium and should not necessarily be considered to equate to a reversal, to any extent, at the mechanistic level of any particular resistance mechanism. As can be seen from the Examples, alginate oligomers and antibiotics have a combinatorial, e.g. synergistic, effect that makes bacteria with a phenotype that is resistant to an antibiotic more susceptible to that antibiotic. In one embodiment the alginate oligomer will measurably reduce the MIC value of the resistant bacterium to the antibiotic, e.g. the MIC value will be at least 50%, 25%, 20%, 15%, 10%, 5%, 2% or 1% of the MIC value of the bacteria for the antibiotic before treatment in accordance with the invention.

Thus use of alginate oligomers according to the present invention may potentiate the effect of an antibiotic (or increase or improve its efficacy). It may render usable (or effective) an antibiotic previously thought not to be usable/effective against a particular organism, or an antibiotic which is not normally effective against a given organism (e.g. bacterium or bacterial species in question). It may also enable an antibiotic to be used at a reduced dose.

The effects of alginate oligomers in overcoming resistance to antibiotics or in potentiating (etc.) the effects of antibiotics may be seen irrespective of the mechanism of resistance to the antibiotic in question. Nevertheless, particularly good results have been observed with ciprofloxacin. Resistance to this antibiotic may involve accumulation of mutations, in particular in the genes encoding DNA gyrase or topoisomerase IV. Without wishing to be bound by theory, the alginate oligomers of the invention may therefore affect this accumulation process, e.g. by preventing, slowing or halting it. However, it is not to assumed from or implied by this, that alginate oligomers may have any effect on any mechanism of resistance.

In a preferred embodiment of the method of the invention the alginate oligomer overcomes resistance to at least two, e.g. at least 3, 4, 5, 6, 7, 8, 9, 10 or all of the structurally and/or functionally different antibiotics or antibiotic classes to which the bacterium is resistant. However, as noted above, it is not required, or implied, that all of the resistance of any given MDR strain is overcome. The invention may for example be effective in overcoming resistance to certain classes of antibiotic in a given MDR strain (e.g. to macrolides and/or quinolones and/or β-lactams) and this may be clinically useful, even though resistance to other antibiotics may remain. This embodiment will preferably entail the use of a plurality of antibiotics corresponding in number and identity to some or all of the antibiotic resistances overcome.

In other embodiments the method of the invention overcomes resistance in an MDR bacterium (e.g. a bacterium from an MDR strain of bacteria) to at least one antibiotic that is a conventional treatment of that bacterium. Put differently, the method of the invention may overcome resistance in an MDR bacterium (e.g. bacterium from an MDR strain of bacteria) to an antibiotic to which that bacterium has acquired or developed resistance. In these embodiments the method of the invention overcomes at least one acquired resistance in an MDR bacterium (e.g. bacterium from an MDR strain of bacteria) that has acquired resistance to at least one, e.g. at least 2, 3, 4, 5, 6, 7, 8, 9 or 10 structurally and/or functionally different antibiotics or antibiotic classes. Preferably all of the acquired antibiotic resistance of the bacterium is overcome. It will be clear to the skilled reader that the invention therefore makes possible the treatment of an MDR bacterium (e.g. bacterium from an MDR strain of bacteria) with an antibiotic that had become ineffective in the treatment of that bacterium. However, as noted above, not all resistance in an MDR phenotype may be acquired and the invention is not limited to this. Thus the invention may be used in the treatment of bacteria that are innately MDR.

The method of the invention may entail contacting the bacterium with more than one antibiotic. The additional antibiotic(s) can be any antibiotic, e.g. those listed above. The additional antibiotic(s) may be an antibiotic to which the bacterium is susceptible. The additional antibiotic(s) may be an antibiotic to which the bacterium is resistant. The additional antibiotic(s) may be used together with (in conjunction or combination with) the first or other antibiotics and/or the alginate oligomer. More particularly, the step of using may comprise contacting the bacterium with an alginate oligomer at the same or substantially the same time or prior to contacting the bacterium with some or all of the antibiotics in an amount effective to overcome the resistance of the bacteria to the antibiotic(s).

As noted above the antibiotic(s) may conveniently be applied or administered simultaneously with the alginate oligomer, or immediately or almost immediately before or after the alginate oligomer. However the antibiotic(s) may be applied or administered at a different time point e.g. least 1 hour, at least 3 hours, at least 6 hours after the alginate oligomer. It is within the skill of the medical practitioner to develop dosage regimes which optimise the effect of the alginate oligomer and antibiotic. In these embodiments the antibiotic(s) can be applied or administered with or without a further application of an alginate oligomer. The alginate oligomer can be applied or administered in a plurality of applications prior to or with the antibiotic(s). In other embodiments the antibiotic(s) may conveniently be applied or administered before the alginate oligomer, e.g. at least 1 hour, at least 3 hours, at least 6 hours before the alginate oligomer. In these embodiments the alginate oligomer can be applied or administered with or without a further application of the antibiotic(s). The antibiotic(s) can be applied or administered in a plurality of applications prior to or with the alginate oligomer. The skilled man can easily determine what would be an appropriate dosing regime for the alginate oligomer and antibiotic(s) he intends to use.

Preferred antibiotic combinations can be two or more from colistin, ciprofloxacin, meropenem, ceftazidime, aztreonam, azithromycin, clarithromycin, dirithromycin, erythromycin, roxithromycin, spiramycin and imipenem/cilastatin, amikacin, gentamicin, oxytetracycline, tobramycin and vancomycin. More particularly, these may be selected from ciprofloxacin, meropenem, ceftazidime, aztreonam, azithromycin, clarithromycin, dirithromycin, erythromycin, roxithromycin, spiramycin imipenem/cilastatin or oxytetracycline, and still more particularly from ciprofloxacin, meropenem, ceftazidime, aztreonam, azithromycin, clarithromycin, dirithromycin, erythromycin, roxithromycin, spiramycin and imipenem/cilastatin.

In preferred embodiments the bacteria is an MDR *Acinetobacter*, *Klebsiella*, or *Pseudomonas* (e.g. *Acinetobacter baumannii*, *Klebsiella pneumoniae*, or *Pseudomonas aeruginosa*) resistant to ceftazidime, ciprofloxacin and azithromycin and the antibiotics used are ceftazidime or ciprofloxacin together with azithromycin or all of ceftazidime, ciprofloxacin and azithromycin.

The location of the bacterium which may targeted in any aspect of the present invention is not restricted, and thus as indicated above, not only are medical uses covered, but also non-medical uses where the bacterium is not present on or within a clinical subject, but may for example be present at an abiotic location i.e. the invention may be carried out in vitro. The bacterium may be present on a surface. The surface is not limited and includes any surface on which a bacterium may occur. The surface may be biotic or abiotic, and inanimate (or abiotic) surfaces include any such surface which may be exposed to microbial contact or contamination. Thus particularly included are surfaces on medical equipment, or machinery, e.g. industrial machinery, or any surface exposed to an aquatic environment (e.g. marine equipment, or ships or boats or their parts or components), or any surface exposed to any part of the environment, e.g. pipes or on buildings. Such inanimate surfaces exposed to microbial contact or contamination include in particular any part of: food or drink processing, preparation, storage or dispensing machinery or equipment, air conditioning apparatus, industrial machinery, e.g. in chemical or biotechnological processing plants, storage tanks, medical or surgical equipment and cell and tissue culture equipment. Any apparatus or equipment for carrying or transporting or delivering materials is susceptible to microbial contamination. Such surfaces will include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

As noted above, medical or surgical equipment or devices represent a particular class of surface on which bacterial contamination may form. This may include any kind of line, including catheters (e.g. central venous and urinary catheters), prosthetic devices, e.g., heart valves, artificial joints, false teeth, dental crowns, dental caps and soft tissue implants (e.g. breast, buttock and lip implants). Any kind of implantable (or "in-dwelling") medical device is included (e.g. stents, intrauterine devices, pacemakers, intubation tubes (e.g. endotracheal or tracheostomy tubes), prostheses or prosthetic devices, lines or catheters). An "in-dwelling" medical device may include a device in which any part of it is contained within the body, i.e. the device may be wholly or partly in-dwelling.

The surface can be made of any material. For example it may be metal, e.g. aluminum, steel, stainless steel, chrome, titanium, iron, alloys thereof, and the like. The surface can also be plastic, for example, polyolefin (e.g., polyethylene, (Ultra-High Molecular Weight) polyethylene, polypropylene, polystyrene, poly(meth)acrylate, acrylonitrile, butadiene, ABS, acrylonitrile butadiene, etc.), polyester (e.g., polyethylene terephthalate, etc.), and polyamide (e.g., nylon), combinations thereof, and the like. Other examples include acetal copolymer, polyphenylsulfone, polysulfone, polyethermide, polycarbonate, polyetheretherketone, polyvinylidene fluoride, poly(methyl methacrylate) and poly(tetrafluoroethylene). The surface can also be brick, tile, ceramic, porcelain, wood, vinyl, linoleum, or carpet, combinations thereof, and the like. The surfaces can also be food, for example, beef, poultry, pork, vegetables, fruits, fish, shellfish, combinations thereof, and the like. The "treatment" of any such surface (i.e. the application to any such surface of an alginate oligomer together with an antibiotic) to combat infection by an MDR bacterium is encompassed by the present invention In an infection by an MDR bacterium, which may be treated according to the present invention, the bacterium may occur in or on a surface in a subject. Furthermore, outside the context of medical treatment, bacteria may also occur on biotic surfaces. Thus the invention includes the treatment of biotic surfaces. A biotic or animate surface may include any surface or interface in or on an animal, plant or fungal body. It may accordingly be viewed as a "physiological" or "biological" surface. It may be any internal or external body surface, including of any tissue or organ, which, in the case of an animal body, may include haematological or haematopoietic tissue (e.g. blood). Dead or dying (e.g. necrotic) or damaged (e.g. inflamed or disrupted or broken) tissue is particularly susceptible to bacterial contamination, and such tissue is encompassed by the term "animate" or "biotic". The surface may be a mucosal or non-mucosal surface.

Representative biotic surfaces include, but are not limited to, any surface in the oral cavity (e.g. teeth, gingiva, gingival crevice, periodontal pocket) the reproductive tract (e.g. cervix, uterus, fallopian tubes), the peritoneum, middle ear, prostate, urinary tract, vascular intima, the eye i.e. ocular tissue (e.g. the conjunctiva, corneal tissue, lachrymal duct; lachrymal gland, eyelid) the respiratory tract, lung tissue (e.g. bronchial and alveolial), heart valves, gastrointestinal tract, skin, scalp, nails and the interior of wounds, particularly chronic wounds and surgical wounds, which may be topical or internal wounds. Other surfaces include the exterior of organs, particularly those undergoing transplantation, for example, heart, lungs, kidney, liver, heart valve, pancreas, intestine, corneal tissue, arterial and venous grafts and skin.

In one aspect the surface will not be mucosal, or more particularly will not have a hyperviscous mucus coating. The skilled person will be able to determine when the mucus at a given surface is hyperviscous. In one embodiment the surface will not be the surface of a mucus-secreting tissue. More particularly in such an embodiment the surface will not be the surface of a mucus-coated tissue. The skilled person will know from his common general knowledge the tissues that secrete mucus and those that are mucus-coated.

The location may also be a location that is not a surface. In other words the bacterium can be found within an material as well as on its surface. The material can be chemically heterogeneous as well as chemically homogenous. The material can also be constructed or formed from or comprise different parts or components. The material can be a part of a larger material or entity. The material may be or comprise the materials from which the above mentioned surfaces are formed. In some instances the material can be considered to be an object, which terms covers volumes of liquids wherever found. The material may comprise any of the above described surfaces. The material may be abiotic or biotic (inanimate or animate) as is discussed above in relation to surfaces. For instance, the material might be, completely or in part, a solid, a liquid, a semi solid, a gel or a gel-sol. Thus, for example, the bacterium might be present in body fluids (e.g. blood, plasma, serum, cerebrospinal fluid, GI tract contents, semen, sputum and other pulmonary secretions); tissues (e.g. adrenal, hepatic, renal, pancreatic, pituitary, thyroid, immune, ovarian, testicular, prostate, endometrial, ocular, mammary, adipose, epithelial, endothelial, neural, muscle, pulmonary, epidermis, osseous); cell and tissue culture media; cell and tissue cultures; clinical/scientific waste materials (which can comprise any of the preceding materials); pharmaceuticals (e.g. tablets, pills, powders, lozenges, sachets, cachets, elixirs, suspensions, emulsions, solutions, syrups, aerosols, sprays, compositions for use in nebulisers, ointments, soft and hard gelatine capsules, suppositories, sterile injectable solutions, sterile packaged powders); animal or human food stuffs (e.g. meat, fish, shellfish, vegetables, cereals, diary products, fruit juices, vegetable juices, sauces, stocks, soups, confectionary, alcoholic beverages, condiments); personal hygiene products (e.g. toothpaste, mouthwash, shampoo, soap, deodorant, shower gel); cosmetics (e.g. lip gloss, eye shadow, foundation); drinking water supplies; waste water supplies; agricultural feedstuffs and water supplies; insecticide, pesticide and herbicide formulations; industrial lubricants and so on. Liquids, semi solids, gels or gel-sols are of note. The body fluids and tissues may be treated in vitro/ex vivo as well as it being possible to treat the same in vivo.

In certain embodiments the bacterium will be in a biofilm. In other embodiments the bacterium will not be in a biofilm. (e.g. will be growing planktonically). Put differently, the bacterium will be, or will not be, in a biofilm mode of growth; or will be, or will not be, in a non-biofilm mode of growth.

By "biofilm" it is meant a community of microorganisms characterized by a predominance of sessile cells that are attached to a substratum or interface or to each other (some motile cells may also be present) and that are embedded in a matrix of extracellular polymers (more specifically extracellular polymers that they have produced) characterised in that the microorganisms of this colony exhibit an altered phenotype with respect to growth rate and gene transcription (for example as compared to their "non-biofilm" or free-floating or planktonic counterparts). By "in a biofilm", it is meant that the bacterium targeted by the method of the invention is within (completely or in part), on or associated with the polymer matrix of a biofilm. Viewed differently, bacteria that are "not in a biofilm" are organisms that are either in isolation, e.g. planktonic, or if in an aggregation of a plurality of organisms, that aggregation is unorganised and/or is devoid of the matrix characteristic of a biofilm. In each case, the individual bacteria do not exhibit an altered phenotype that is observed in their biofilm dwelling counterparts.

It is well appreciated that *Acinetobacter* organisms can form a capsule from extracellular polymers (e.g. polysaccharides) that they have produced and *Acinetobacter* organisms are typically found with such a capsule. It is also well appreciated that the simple presence of a polymer capsule of an *Acinetobacter* organism is not functionally equivalent to a biofilm mode of growth and the presence of such a capsule is therefore not in itself indicative of a biofilm phenotype. Thus, it will also be appreciated that *Acinetobacter* organisms that are "not in a biofilm" may still be in contact a matrix of extracellular polymers that they have produced (i.e. the capsule), but such organisms will not exhibit an altered phenotype that is observed in their biofilm dwelling counterparts. Thus, in the particular case of *Acinetobacter*, by "in a biofilm" it is meant that the *Acinetobacter* organism is within (completely or in part), on or associated with the polymer matrix of a biofilm and has an phenotype characteristic of *Acinetobacter* organisms in a biofilm (i.e. a phenotype that is altered with respect to growth rate and gene transcription, for example as compared to "non-biofilm" or free-floating or planktonic *Acinetobacter* organisms. *Acinetobacter* organisms that are "not in a biofilm" are organisms that are either in isolation, e.g. planktonic, or if in an aggregation of a plurality of organisms, that aggregation is unorganised. In each case, the individual *Acinetobacter* organisms do not exhibit an altered phenotype that is observed in their biofilm dwelling counterparts.

From the forgoing it is clear that the methods of the invention, i.e. those described above, have medical and non-medical applications. In particular, the invention provides a method for combating contamination of a site with bacteria that are MDR, in particular the treatment in a subject of a bacterial infection that is MDR, and also a method of combating a population of MDR bacteria. Thus, the method may be an in vitro or an in vivo method. As explained in more detail below, "combating" includes both the treatment of an existing contamination or infection, and treatment to prevent a contamination or infection from occurring, i.e. both "therapeutic"/reactionary and prophylactic treatments.

Accordingly, in one aspect of the invention there is provided a method for the treatment or prevention of an infection of a subject by an MDR bacterium, said method comprising administering to said subject a pharmaceutically effective amount of an alginate oligomer together with a pharmaceutically effective amount of at least one antibiotic to which the bacterium is resistant.

Thus the invention provides an alginate oligomer for use together with (or in combination or conjunction with) at least one antibiotic in the treatment or prevention of an infection of a subject by an MDR bacterium, wherein the bacterium is resistant to the antibiotic.

The term "use together" should be construed as discussed above, although it is particularly meant that a pharmaceutically effective amount of the alginate oligomer is administered at the same or substantially the same time as or prior to, or after, administering a pharmaceutically effective amount of the antibiotic.

Alternatively put, the invention provides the use of an alginate oligomer for the manufacture of a medicament for use together with an antibiotic in the treatment or prevention of an infection of a subject by an MDR bacterium, wherein the bacterium is resistant to the antibiotic.

As noted above, the medicament may further comprise the antibiotic, and single or separate compositions or formulations may be provided and used, as discussed above.

This aspect of the invention also provides the use of an alginate oligomer together with an antibiotic in the manufacture of a medicament for use in the treatment of an infection of a subject by an MDR bacterium, wherein the bacterium is resistant to the antibiotic.

Also provided according to this aspect of the invention is a product containing an alginate oligomer and an antibiotic as a combined preparation for separate, simultaneous or sequential use in the treatment or prevention of an infection of a subject by an MDR multidrug resistant bacterium, wherein the bacterium is resistant to the antibiotic.

The MDR bacterium can be any species of bacteria, e.g. those discussed above and mentioned as preferred, e.g. a *Burkholderia* organism, e.g. *Burkholderia cepacia*. The antibiotic can be any antibiotic e.g. those discussed above and mentioned as preferred, e.g. a macrolide, e.g. azithromycin, clarithromycin, dirithromycin, erythromycin, roxithromycin or spiramycin.

The subject may be any human or non-human animal subject, but more particularly may be a vertebrate, e.g. an animal selected from mammals, birds, amphibians, fish and reptiles. The animal may be a livestock or a domestic animal, or an animal of commercial value, including laboratory animals or an animal in a zoo or game park. Representative animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, cod, haddock, sea bass and carp. Veterinary uses of the invention are thus covered. The subject may be viewed as a patient. Preferably the subject is a human.

The term "in a subject" is used broadly herein to include sites or locations inside a subject or on a subject, e.g. an external body surface, and may include in particular infection of a medical device e.g. an implanted or "in-dwelling" medical device. The term "in a patient" should be interpreted consistently with this.

The location of the infection is not restricted and may be any of the sites or locations in a subject described above. Administering the alginate oligomer and the antibiotic to the subject preferably results in the infected location being contacted with an alginate oligomer and antibiotic in amounts sufficient to treat the infection.

The infection may be acute, or alternatively chronic, e.g. an infection that has persisted for at least 5 or at least 10 days, particularly at least 20 days, more particularly at least 30 days, most particularly at least 40 days.

In this aspect of the invention the infection may occur on a surface in or on the subject (i.e. a biotic surface as discussed above) and/or a surface of a medical device, particularly an implantable or "in-dwelling" medical device, representative examples of which are discussed above.

In one embodiment the methods or uses of the invention may comprise a step in which the subject is identified (e.g. diagnosed) as having or suspected to have an MDR bacterial infection or being a candidate that is at risk of or susceptible to an MDR bacterial infection.

In particular embodiments the invention may provide for the treatment of respiratory infections, e.g. cystic fibrosis, pneumonia, COPD, COAD, COAP, bacteraemia, septicaemia, septic shock, sepsis, meningitis, or poisoning by bacterially derived toxins.

An MDR bacterial infection can occur in any subject but some subjects will be more susceptible to infection that others. Subjects who are susceptible to MDR bacterial infection include, but are not limited to, subjects whose epithelial and/or endothelial barrier is weakened or compromised, subjects whose secretion-based defences to microbial infection have been abrogated, disrupted, weakened or undermined, and subjects who are immunocompromised, immunodeficient or immunosuppressed (i.e. a subject in whom any part of the immune system is not working normally, or is working subnormally, in other words in whom any part of the immune response, or an immune activity is reduced or impaired, whether due to disease or clinical intervention or other treatment, or in any way).

Representative examples of subjects who are susceptible to MDR bacterial infection include, but are not limited to, subjects with a pre-established infection (e.g. with bacteria, viruses, fungi or parasites such as protozoa), especially subjects with HIV, subjects with bacteraemia, sepsis and subjects with septic shock; subjects with immunodeficiency, e.g. subjects preparing for, undergoing or recovering from chemotherapy and/or radiotherapy, organ (e.g. bone marrow, liver, lung, heart, heart valve, kidney, etc.) transplant subjects (including autograft, allograft and xenograft patients); subjects with AIDS; subjects resident in a healthcare institution, e.g. hospital, especially subjects in intensive care or critical care (i.e. those units concerned with the provision of life support or organ support systems to patients); subjects on respiratory ventilators; subjects suffering from trauma; subjects with burns, subjects with acute and/or chronic wounds; neonatal subjects; elderly subjects; subjects with cancer (defined broadly herein to include any neoplastic condition; malignant or non-malignant), especially those with cancers of the immune system (e.g. leukaemias, lymphomas and other haematological cancers); subjects suffering from auto-immune conditions such as rheumatoid arthritis, diabetes mellitus type I, Crohn's disease, especially those undergoing immunosuppression treatment for those diseases; subjects with reduced or abrogated epithelial or endothelial secretion (e.g. mucous, tears, saliva) and/or secretion clearance (e.g. subjects with poorly functioning cilia on mucosal tissue and/or patients with hyperviscous mucous (e.g. smokers and subjects with COPD, COAD, COAP, bronchitis, cystic fibrosis, emphysema, lung cancer, asthma, pneumonia or sinusitis)) and subjects fitted with a medical device.

MDR bacteria are commonly encountered in healthcare institutions due in part to the close proximity of subjects with bacterial infection's and the widespread-use of antibiotics. MDR bacteria, e.g. from the genera *Pseudomonas, Klebsiella, Burkholderia, Providencia* and *Acinetobacter*, are therefore often involved in nosocomial infections and accordingly the invention can be seen as providing treatments for MDR nosocomial infections.

Thus, subjects in whom MDR infections may particularly be combated according to the present invention include patients who are impaired, whether due to poor perfusion, repetitive trauma, poor nutrition, poor oxygenation or white cell dysfunction.

Of particular note are subjects that have undergone physical trauma. The trauma itself might cause a weakening in or compromisation of an epithelial and/or endothelial barrier of the subject or the subject may become immunocompromised in response to the trauma (a shock response). The term "trauma" refers broadly to cellular attack by foreign bodies and/or physical injury of cells. Included among foreign bodies are microorganisms, particulate matter, chemical agents, and the like. Included among physical injuries are mechanical injuries; thermal injuries, such as those resulting from excessive heat or cold; electrical injuries, such as those caused by contact with sources of electrical potential; and radiation damage caused, for example, by prolonged, extensive exposure to infrared, ultraviolet or ionizing radiations.

Also of particular note are subjects that have a burn. Any burn, in particular a severe burn, has a significant impact on the integrity of the epithelial and/or endothelial barrier of the subject and the subject will often become immunocompromised in response to the burn (a shock response).

Typical burn-causing agents are extremes of temperature (e.g. fire and liquids and gases at extreme temperature), electricity, corrosive chemicals, friction and radiation. The extent and duration of exposure, together with the intensity/strength of the agent, result in burns of varying severity. Scalding (i.e. trauma associated with high temperature liquids and/or gases) is considered to be a burn.

Epidermal burn severity is commonly classified in two ways. Most common is the classification by degree. First-degree burns are usually limited to erythema (redness) in the general area of the injury and a white plaque at the site of injury. The cellular trauma of these burns extends only as deep as the epidermis. Second-degree burns also display erythema in the general area of the injury but with superficial blistering of the epidermis. The cellular trauma of second-degree burns involves the superficial (papillary) dermis and may also involve the deep (reticular) dermis layer. Third-degree burns are those in which the epidermis is lost with damage to the hypodermis. Damage is typically extreme including charring. Sometimes eschar, (dry, black necrotic tissue) will be present. Third-degree burns may require grafting. In fourth-degree burns catastrophic damage of the hypodermis occurs, e.g. the hypodermis is completed lost, with damage extending to the underlying muscle, tendon, and ligament tissue. Charring and eschar are observed. Grafting is required if the burn does not prove to be fatal.

Another common classification system is the classification by thickness. "Superficial thickness" burns correspond to first degree burns. The spectrum of second degree burns is covered by two classes of "partial thickness" burns. "Partial thickness-superficial" are burns that affect the epidermis only as far as the papillary dermis. "Partial thickness-deep" are burns that affect the dermis as far as the reticular dermis. "Full thickness" burns correspond to third and fourth degree burns.

Some physical injuries, e.g. some burns, and cellular attacks by foreign bodies result in the formation of a wound. More specifically a wound may be considered to be a breach in, or denudement of, a tissue. Wounds may also be caused by a spontaneously forming lesion such as a skin ulcer (e.g. a venous, diabetic or pressure ulcer), an anal fissure or a mouth ulcer.

Wounds are typically defined as either acute or chronic. Acute wounds are wounds that proceed orderly through the three recognised stages of the healing process (i.e. the inflammatory stage, the proliferative stage and the remodelling phase) without a protracted timecourse. Chronic wounds, however, are those wounds that do not complete the ordered sequence of biochemical events of the healing process because the wound has stalled in one of the healing stages. Commonly, chronic wounds are stalled in the inflammatory phase. In accordance with a particular aspect of the present invention, a chronic wound is a wound that has not healed within at least 40 days, particularly at least 50 days, more particularly at least 60 days, most particularly at least 70 days.

As discussed above, wounds are an ideal environment for an MDR bacterial infection, particularly chronic infection, due to their lack of an epithelial barrier and the availability of substrate and surface for microbial attachment and colonisation. Problematically, infection of a wound often delays healing further and thus renders that wound more susceptible to established infection. The methods of the invention are therefore effective in the treatment and prevention of MDR bacterial infection of wounds and the use of the methods of the invention in the treatment of wounds, especially chronic wounds, represents one preferred aspect of the present invention.

Therefore, in an embodiment of the invention there is provided an alginate oligomer for use together with (or in combination or conjunction with) an antibiotic in the treatment or prevention of the infection of a subject by an MDR bacterium, wherein the bacterium is resistant to the antibiotic, particularly chronic infection by an MDR bacterium in the above-mentioned subjects, in particular in subjects with respiratory diseases or disorders e.g. cystic fibrosis, COPD, COAD, COAP, pneumonia, wounds, burns and/or traumas.

Through the ability to treat and prevent infection of wounds by an MDR bacterium the alginate oligomers and antibiotics of the invention as defined herein can remove one of the obstacles to wound healing and therefore the alginate oligomers and antibiotics defined above are also effective in the promotion of healing of acute and chronic wounds infected with or at risk of infection with an MDR bacterium which is resistant to any of said antibiotics By promotion of healing it is meant that the treatment accelerates the healing process of the wound in question (i.e. the progression of the wound through the three recognised stages of the healing process). The acceleration of the healing process may manifest as an increase in the rate of progression through one, two or all of the healing stages (i.e. the inflammatory stage, the proliferative stage and/or the remodelling phase). If the wound is a chronic wound that is stalled in one of the healing stages the acceleration might manifest as the restarting of the linear, sequential healing process after the stall. In other words, the treatment shifts the wound from a non-healing state to a state where the wound begins to progress through the healing stages. That progression after the restart may be at a normal rate or even a slower rate compared with the rate a normal acute wound would heal.

The alginate oligomers and antibiotics of the invention may be used together (or in combination or conjunction with) to treat or prevent MDR bacterial infections wherever they may occur in or on the body. Thus, in another embodiment, the infection may be an infection of a medical device by an MDR bacterium, particularly an in-dwelling medical device, e.g. endotracheal and tracheostomy tubes.

The alginate oligomers and antibiotics of the invention may be used together (or in combination or conjunction) as oral healthcare agents, for example in the control of dental plaque, e.g. to reduce it or to prevent, reduce or delay its development by inhibiting growth of MDR plaque bacteria on teeth or dental/oral prostheses. The alginate oligomers and antibiotics of the invention may also be used together (or in combination or conjunction) in the treatment and prevention of MDR infections or MDR infectious disease which may occur in the oral cavity, for example gingivitis and periodontitis Conveniently, the alginate oligomers and/or antibiotics can be applied by any oral health/oral hygiene delivery system. This may be through the use of toothpastes, dental gels, dental foams and mouthwashes. Removable dentures and other removable dental prostheses may be treated outside of the oral cavity with the same compositions or other suitable pharmaceutically acceptable compositions. The alginate oligomers and/or antibiotics can also be incorporated into compositions that are applied to the oral cavity (or applied to removable dentures and other removable dental prostheses outside of the oral cavity) to form a coating that persists on surfaces over time, or that releases the alginate oligomers and/or antibiotics from the coated surfaces over time, and which inhibit the growth of MDR bacteria in the oral cavity and on the surfaces of removable dentures and other removable dental prostheses.

Whilst the treatment of MDR bacterial infections of the lungs and respiratory tract and all areas of the body is generally covered by the present invention, in one embodiment, the medical uses of the invention are not directed to the treatment of (i) infections in the respiratory tract, e.g. in patients suffering from COPD's (chronic obstructive pulmonary diseases), in particular the sinuses and the lungs, in particular in the treatment of cystic fibrosis, chronic obstructive pulmonary disease, emphysema, bronchitis and sinusitis; (ii) in the middle ear of patients suffering from glue ear; or (iii) in the reproductive tract of female patients with impaired fertility; or (iv) in the digestive tract of patients with digestive tract malfunction (e.g. constipation).

In specific embodiments of the invention the alginate oligomers and antibiotics of the invention may be used together (or in combination or conjunction) in the treatment or prevention of native valve endocarditis, acute otitis media, chronic bacterial prostatitis, pneumonia (in particular ventilator associated pneumonia) associated with MDR bacteria; respiratory diseases associated with MDR bacteria (which may include COPD, COAD, COAP, pneumonia, cystic fibrosis and asthma); and device related MDR bacterial infections associated with implantable or prosthetic medical devices (e.g. prosthetic valve endocarditis or the infection of lines or catheters or artificial joints or tissue replacements or endotracheal or tracheotomy tubes).

In further embodiments the alginate oligomers and antibiotics of the invention are used together to control MDR infections in the eye, e.g. to reduce them, or prevent, reduce or delay their development. In particular, the alginate and antibiotics of the invention are used together to treat or prevent MDR bacterial conjunctivitis and the resultant keratoconjunctivitis sicca (also known as dry eye) that can result through the blockage of the lachrymal gland.

As mentioned previously, in certain embodiments, the above MDR bacterial infections and associated conditions are, or involve, biofilm, in other words they are biofilm infections. In other embodiments the above MDR bacterial infections and associated conditions are not, or do not involve biofilm.

In a further aspect the invention provides a method for combating contamination of a site with MDR bacteria, said method comprising contacting the site and/or the MDR bacteria with (an effective amount of) an alginate oligomer together with (an effective amount of) at least one antibiotic to which the bacteria are resistant. Such a method may particularly be an in vitro method, and the site may be any surface or location discussed above.

"Combating contamination" includes both preventative and reactionary measures or treatments and therefore covers the prevention as well as the reduction, limitation, or elimination of contamination.

By "contamination" it is meant the unwanted presence of a bacterium (e.g. an MDR bacterium) at a particular site or location. Contamination can be considered to cover colonisation of a location by a bacterium (e.g. an MDR bacterium), i.e. the establishment of a bacterium (e.g. an MDR bacterium) at a location and the expansion of the numbers of that organism by replication or the recruitment of additional bacteria, which may be of the same or of a different type. In one embodiment the colonisation process will not involve the formation of a biofilm.

The site or location of the contamination or potential contamination is not restricted and can be any of the various sites or locations described or mentioned above, e.g. it can be in vitro or in vivo, but particularly in this aspect of the invention it will be an "in vitro" or "ex vivo" site or location (e.g. an inanimate or abiotic site or location). However, the site or location may be in a subject and in which case a pharmaceutically effective amounts of the alginate oligomer and the antibiotic are administered to the subject.

In one particular embodiment the various aspects of the invention can be applied to the decontamination of clinical, scientific and industrial waste materials. In another particular embodiment the various aspects of the invention can be used to decontaminant transplant tissue (e.g. heart, lungs, kidney, liver, heart valve, pancreas, intestine, corneal tissue, arterial and venous grafts and skin) and medical devices (e.g. endotracheal and tracheostomy tubes) prior to implantation. In another embodiment the various aspects of the invention can be considered to cover the use of alginate oligomers together with antibiotics as anti-MDR bacterial preservative agents in materials, especially solutions and liquids.

In another embodiment, the methods of the invention may further comprise a step in which the bacteria being targeted will be determined as being, or alternatively not being in, or involving, a biofilm.

In other embodiments of the methods of the invention the methods may comprise a step in which it is determined (e.g. ascertained or identified) that the bacterium is resistant to a particular antibiotic(s). In a step in place of, or in addition to, the previously described step, there may be a step in which it is determined that the bacterium is an MDR bacterium. Any convenient test can be used here, for instance those described above, or any technique for identifying known and characterised bacteria (e.g. bacteria already identified as being antibiotic and/or multidrug resistant). In a further step it may be ascertained whether or not a particular resistance is acquired or intrinsic, e.g. by comparison to typical or wild type bacteria of the same species.

In any of the aspects, uses or methods of the invention the MDR bacteria and the antibiotic can be any of the bacteria and antibiotics defined above and especially any, or combinations thereof, stated as preferred. For example, the MDR bacteria may be a bacteria from an MDR strain of bacteria. Also for example, the MDR bacteria may be a *Burkholderia* organism, e.g. *Burkholderia cepacia*. Also for example the antibiotic may be a macrolide, e.g. azithromycin, clarithromycin, dirithromycin, erythromycin, roxithromycin or spiramycin.

The term "contacting" encompasses any means of delivering the alginate oligomer and the antibiotic to the MDR bacterium, whether directly or indirectly, and thus any means of applying the alginate oligomer and the antibiotic to the MDR bacterium or exposing the MDR bacterium to the alginate oligomer and the antibiotic e.g. applying the alginate oligomer and the antibiotic directly to the MDR bacterium or administering the alginate oligomer and the antibiotic to a subject within which or on which the MDR bacterium is present, e.g. a subject infected with an MDR bacterium.

More particularly the MDR bacterium will be contacted with an effective amount of the alginate oligomer and the antibiotic, more particularly an amount of the alginate oligomer and an amount of the antibiotic that together (or in combination or conjunction) overcome the resistance of the MDR bacterium to the antibiotic and therefore inhibit the viability and/or growth of the MDR bacterium and therefore treat or prevent the infection/contamination.

An "effective amount" of the alginate oligomer and the antibiotic is that amount of alginate oligomer and that amount of the antibiotic that together (or in combination or conjunction) provide measurable reduction in the resistance (or measurable increase in susceptibility or measurable decrease in tolerance) to the antibiotic displayed by the bacterium (e.g. using the above-described indicators of resistance). In certain embodiments the "effective amount" of the alginate oligomer and the antibiotic is that amount of alginate oligomer and that amount of the antibiotic that together (or in combination or conjunction) provide measurable inhibition of the growth of an MDR bacterium, or population thereof, that is being targeted, e.g. which is resistant to the antibiotic.

A "pharmaceutically effective" amount of the alginate oligomer and the antibiotic is that amount of alginate oligomer and that amount of the antibiotic that together (or in combination or conjunction) provide a measurable reduction in the resistance (or measurable increase in susceptibility or measurable decrease in tolerance) to the antibiotic displayed by the MDR bacterium (e.g. using the above-described indicators of resistance) in a subject and/or a measurable treatment or prevention of the infection by an MDR bacterium that is being targeted.

The skilled man would easily be able to determine what an effective/pharmaceutically effective amount of alginate oligomer and antibiotic would be on the basis of routine dose response protocols and, conveniently, the routine techniques for assessing microbial growth inhibition etc., as discussed below. The skilled man would, without undue burden, also be able to optimise these amounts to maximise the combinatorial effects of the alginate oligomer and antibiotic in his target system.

By "growth of an MDR bacterium" it is meant both an increase in the size of an MDR bacterium or in the amount and/or volume of the constituents of an MDR bacterium (e.g. the amount of nucleic acid, the amount of protein, the number of nuclei, the numbers or size of organelles, the volume of cytoplasm) and an increase in the numbers of the MDR bacterium, i.e. an increase in the replication of the MDR bacterium.

Typically growth of an MDR bacterium is accompanied by the enlargement of the organism. The growth of MDR bacteria can be measured with routine techniques. For instance, microscopic examination of microorganism morphology over time, or assays to measure changes in the quantities of protein or nucleic acid (e.g. DNA) in general, or the changes in the quantities of specific proteins or nucleic acids, can be used. The skilled man would easily be able to select suitable markers to follow. Conveniently, so called housekeeping genes (e.g. β-actin, GAPDH (glyceraldehyde 3-phosphate dehydrogenase), SDHA (succinate dehydrogenase), HPRT1 (hypoxanthine phosphoribosyl transferase 1), HBS1L (HBS1-like protein), AHSP (alphahaemoglobin stabilising protein), and β2M (beta-2-microglobulin)), 16S RNA and virus genes, and their expression products can be monitored.

By "replication of an MDR bacterium" or "replication of a bacterium" it is meant the act by which the (MDR) bacterium reproduces. Typically this is by binary fission where a microorganism divides into two. To support the division of the microorganism into two, binary fission is normally preceded by enlargement of the dividing microorganism and an increase in the amount and/or volume of cellular constituents. Replication results in an increase in the number of cells and so may be followed by any method of assessing microorganism numbers in a population. Another option is to follow the process in real time by visual examination with a microscope. The time it takes for microorganism to replicate (i.e. produce another version of itself) is the generation time. Generation time will depend on the conditions in which the (MDR) bacterium is found. The rate of replication can be expressed in terms of the generation time.

By "inhibiting the growth of an MDR bacterium" or "inhibiting the growth of a bacterium" it is meant that measurable growth (e.g. replication) of an (MDR) bacterium, or the rate thereof, is reduced. Preferably measurable growth (e.g. replication) of an (MDR) bacterium, or the rate thereof, is reduced by at least 50%, more preferably at least 60%, 70%, 80% or 90%, e.g. at least 95%. Preferably, measurable growth (e.g. replication) is ceased. Growth in terms of microbial size increase or expansion etc. may be inhibited independently of replication and vice versa.

Suitable doses of alginate oligomer and antibiotic will vary from subject to subject and can be determined by the physician or veterinary practitioner in accordance with the weight, age and sex of the subject, the severity of the condition, the mode of administration and also the particular alginate oligomer or antibiotic selected. Typically the alginate oligomers of the invention will be applied to the location undergoing treatment at a local concentration of at least 0.5%, preferably at least 2% or at least 4%, more preferably at least 6% and most preferably at least 10% weight by volume. Typically the antibiotic of the invention will be applied to the location undergoing treatment at a local concentration of at least 1 µg/ml, preferably at least 4, at least 8, at least 16, at least 32, at least 64, at least 128, at least 256 or at least 512, 1024, 2048 or 4096 µg/ml.

"Treatment" when used in relation to the treatment of a medical condition/infection in a subject in accordance with the invention is used broadly herein to include any therapeutic effect, i.e. any beneficial effect on the condition or in relation to the infection. Thus, not only included is eradication or elimination of the infection, or cure of the subject or infection, but also an improvement in the infection or condition of the subject. Thus included for example, is an improvement in any symptom or sign of the infection or condition, or in any clinically accepted indicator of the infection/condition (for example a decrease in wound size or an acceleration of healing time). Treatment thus includes both curative and palliative therapy, e.g. of a pre-existing or diagnosed infection/condition, i.e. a reactionary treatment.

"Prevention" as used herein refers to any prophylactic or preventative effect. It thus includes delaying, limiting, reducing or preventing the condition (which reference includes infection and contamination, as applicable, in the different aspects of the invention) or the onset of the condition, or one or more symptoms or indications thereof, for example relative to the condition or symptom or indication prior to the prophylactic treatment. Prophylaxis thus explicitly includes both absolute prevention of occurrence or development of the condition, or symptom or indication thereof, and any delay in the onset or development of the condition or symptom or indication, or reduction or limitation on the development or progression of the condition or symptom or indication.

Specifically, the alginate oligomers and antibiotics of the invention can be taken together (or in combination or conjunction) as a prophylactic treatment, for example to prevent, or at least minimise the risk, of infection or contamination by an MDR bacterium resistant to the antibiotic.

The aspect of the invention concerning the combating (treatment or prevention) of infection by an MDR bacterium is of particular utility in the care of hospitalised patients as the risk of contracting an nosocomial infection (commonly known as hospital related/acquired infection or healthcare-associated infection) by an MDR bacterium can be minimised with a prophylactic regime of the alginate oligomers and antibiotics defined herein. This aspect of the invention is also of particular utility in the care of subjects suffering from trauma, subjects with a burn and subjects with wounds, all of which, as discussed above, are more susceptible to infection by MDR bacteria than a subject that is not affected similarly.

Generally, subjects in need of treatment or prophylaxis according to the invention will be diagnosed as suffering or at risk from infection by an MDR bacterium, e.g. identified as having or at risk of developing an infection by an MDR bacterium.

Specifically, the alginate oligomers and antibiotics of the invention can be taken together (or in combination or conjunction) as a prophylactic treatment to prevent, or at least minimise the risk, of developing an infection by an MDR bacterium resistant to the chosen antibiotic(s), including for example the infection of wounds by an MDR bacterium; native valve endocarditis, acute otitis media, chronic bacterial prostatitis, associated with an MDR bacterium; infections of the respiratory tract and lungs by an MDR bacterium (e.g. cystic fibrosis, COPD, COAD, COAP, pneumonia, or other respiratory diseases) or infection of a medical (e.g. in-dwelling) medical device by an MDR bacterium.

The invention encompasses the use of a single alginate oligomer or a mixture (multiplicity/plurality) of different alginate oligomers. Thus, for example, a combination of different alginate oligomers (e.g. two or more) may be used.

The invention encompasses the use of a single antibiotic or a mixture (multiplicity/plurality) of different antibiotics. Thus, for example, a combination of different antibiotics (e.g. two or more) may be used. The MDR bacterium may be sensitive to the further antibiotic(s) used or may be resistant to the further antibiotic(s) used.

In one advantageous embodiment of the invention the alginate oligomers and antibiotic may be used in the methods of the invention in conjunction or combination with a further anti-microbial agent (hereinafter "further anti-microbial agent")

In the context of a medical use, such an anti-microbial agent may be any clinically-useful anti-microbial agent and particularly an antibiotic or an antiviral or antifungal agent. In the context of non-clinical uses, the anti-microbial agent may again be any anti-microbial agent used for such purposes, e.g. any disinfectant or antiseptic or cleaning or sterilising agent. The agents may be used separately, or together in the same composition, simultaneously or sequentially or separately, e.g. at any desired time interval.

Thus, by way of representative example, the further anti-microbial agent may be used after the alginate oligomer and/or the antibiotic, but a preceding or simultaneous or intervening use may be beneficial in some circumstances.

The choice of anti-microbial agent will of course need to be appropriate for the location undergoing treatment, but for instance anti-microbial agents, e.g. antibiotics, antifungals, antivirals, antiseptics may be used and/or sterilising conditions such as irradiation (e.g. UV, X-ray, gamma) extremes of temperature, and extremes of pH.

Representative antibiotics include those listed above, especially those stated as preferred.

Representative antiseptics include, but are not limited to chlorine bleach (sodium hypochlorite), quaternary ammonium compounds (e.g. benzalkonium chloride, cetyl trimethylammonium bromide; cetylpyridinium chloride), hydrogen peroxide, phenol compounds (e.g. TCP), alcohols (e.g. ethanol), Virkon™, iodine compounds (e.g. povidone-iodine), silver compounds (e.g. elemental silver nano/microparticles).

Antimicrobial surfactants are another class of antiseptics. These are compounds that disrupt microbial cell membranes and other structural components and therefore inhibit growth and/or viability of microorganisms. Antimicrobial surfactants and their use in antimicrobial compositions is well known in the art should further guidance be needed the discussion of antimicrobial surfactants in "Preservative-free and self-preserving cosmetics and drugs—Principles and practice", Ed. Kabara and Orth, Marcel Dekker, N.Y., N.Y., 1997, is explicitly incorporated by reference in its entirety. Antimicrobial surfactants may be anionic, cationic, non-ionic or amphoteric. Examples of antimicrobial anionic surfactants include, but are not limited to, sodium dodecyl sulfate (sodium lauryl sulfate), sodium dodecyl aminopropionic acid, sodium ricinoleate, bile acids, alkylaryl sulfonates, Grillosan DS7911, disodium undecylenic acid monoethanol amidosulfosuccinate. Examples of antimicrobial cationic surfactants include, but are not limited to, the quaternary ammionium compounds, the aminimides and chlorhexidine compounds. Examples of antimicrobial non-ionic surfactants include, but are not limited to, the monoesters of fatty acids, polyethyleneglycomonoesters of alkyldihydroxybenzoic acids, glucosamine derivatives and diethanolamides of N-lauroyl dipeptides. Examples of antimicrobial amphoteric surfactants include, but are not limited to, the alkyl betaines, the alkylamidopropylbetaines, the alkyl aminopropionates, the alkyliminodipropionates and the alkylimidazolines.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type, II interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

The further anti-microbial agent may conveniently be applied before, simultaneously with, following or between the alginate oligomer and/or the antibiotic. Conveniently the further anti-microbial agent is applied at substantially the same time as the alginate oligomer and/or the antibiotic or afterwards. For example, the further anti-microbial agent is applied at least 1 hour, preferably at least 3 hours, more preferably at least 5 and most preferably at least 6 hours after the alginate oligomer and/or the antibiotic is administered. In other embodiments the further antimicrobial may conveniently be applied or administered before the alginate oligomer and/or the antibiotic r, e.g. at least 1 hour, at least 3 hours, at least 6 hours before the alginate oligomer and/or the antibiotic. In these embodiments the alginate oligomer and/or the antibiotic can be applied or administered with or without a further application of the further antimicrobial. To optimise the anti-microbial effect of the further anti-microbial agent it can be given (e.g. administered or delivered) repeatedly at time points appropriate for the agent used. The skilled person is able to devise a suitable dosage or usage regimen. In long term treatments the alginate oligomer and/or the antibiotic can also be used repeatedly. The alginate oligomer can be applied as frequently as the antibiotic and/or the further antimicrobial agent, but will typically be less frequently. The frequency required will depend on the location of the MDR bacterium, colony composition and the anti-microbial used and the skilled person is able to optimise the dosage or usage patterns to optimise results.

In an advantageous embodiment the alginate oligomer and/or the antibiotic may be used or applied after physical removal or reduction (e.g. debridement) of the colony/population comprising the MDR bacterium causing the infection at the location undergoing treatment.

Following removal of, or an attempt to remove, the colony/population comprising the MDR bacterium, the location may be contacted with the alginate oligomer for between 0 and 24 hours, particularly 2 and 12 hours, more particularly 4 and 8 hours, most particularly 5 and 7 hours, e.g. 6 hours. Following this, the antibiotic, and if desired the further anti-microbial agent, may be applied. Such a scenario may be desirable or particularly applicable in a clinical setting. In the case of wounds infected by an MDR bacterium, the duration of incubation can be conveniently be designed to correspond to scheduled changes of the wound dressing.

Physical removal of the colony/population comprising the MDR bacterium can be carried out with any suitable surgical, mechanical or chemical means. Conveniently this can be the use of a liquid, gel, gel-sol, semi-solid compositions or gas applied at pressure to the colony/population, sonication, laser, or by abrasive implement. A composition used in the removal itself or as a wash solution before, during or afterwards may conveniently contain the alginate oligomer and/or the antibiotic.

Accordingly, in one specific embodiment there is provided a debridement or wash composition e.g. solution for wounds containing an alginate oligomer, particularly any alginate oligomer as herein defined, and/or an antibiotic, particularly any antibiotic as herein defined (e.g. a macrolide, preferably selected from azithromycin, clarithromycin, dirithromycin, erythromycin, roxithromycin or spiramycin), for use in the treatments and methods of the invention. Such a debridement composition will typically be a sterile solution, particularly an aqueous sterile solution or an oil-based sterile solution, and may additionally contain proteolysis enzymes (e.g. collagenase, trypsin, pepsin, elastase), an abrasive solid phase (e.g. colloidal silica, ground pumice, ground plant or animal shell).

Use of the alginate oligomers and the antibiotic in combination or conjunction with immunostimulatory agents may also be beneficial in the application of the methods of the invention in a clinical situation. These immunostimulatory agents may conveniently be used at timepoints corresponding to those described above in relation to anti-microbial agents and may optionally be used in combination with an alginate oligomer and/or the antibiotic and/or a further anti-microbial agent Suitable immunostimulatory agents include, but are not limited to cytokines e.g. TNF, IL-1, IL-6, IL-8 and immunostimulatory alginates, such as high M-content alginates as described for example in U.S. Pat. No. 5,169,840, WO91/11205 and WO03/045402 which are explicitly incorporated by reference herein in their entirety, but including any alginate with immunostimulatory properties.

Use of the alginate oligomers and the antibiotic in combination or conjunction with growth factors, e.g. PDGF, FGF, EGF, TGF, hGF and enzymes may also be beneficial in the medical uses of the invention. Representative examples of suitable enzymes include but are not limited to proteases, e.g. serine proteases, metalloproteases and cysteine proteases (examples of these types of proteases are listed in EP0590746, the entire contents of which are incorporated herein by reference); nucleases, e.g. DNase I and II, RNase A, H, I, II, III, P, PhyM, R; lipases and enzymes capable of degrading polysaccharides.

Use of the alginate oligomers and the antibiotic in combination or conjunction with a physiologically tolerable mucosal viscosity reducing agent could also be beneficial, e.g. a nucleic acid cleaving enzyme (e.g. a DNase such as DNase I), gelsolin, a thiol reducing agent, an acetylcysteine, sodium chloride, an uncharged low molecular weight polysaccharide (e.g. dextran), arginine (or other nitric oxide precursors or synthesis stimulators), or an anionic polyamino acid (e.g. poly ASP or poly GLU). Ambroxol, romhexine, carbocisteine, domiodol, eprazinone, erdosteine, letosteine, mesna, neltenexine, sobrerol, stepronin, tiopronin are specific mucolytics of note.

Use of the alginate oligomers and the antibiotic in combination or conjunction with alpha blockers may also be beneficial in the medical uses of the invention, in the treatment of chronic bacterial prostatitis especially. Representative examples of suitable alpha blockers include but are not limited to the selective alpha-1 blockers (e.g. doxazosin, dilodosin, prazosin, tamsulosin, alfuzosin, terazosin), and the non-selective adrenergic blockers (e.g. phenoxybenzamine, phentolamine).

Use of the alginate oligomers and the antibiotic in combination or conjunction with bronchodilators may also be beneficial in the medical uses of the invention, in the treatment of respiratory diseases associated with MDR bacteria especially (which may include COPD, COAD, COAP, pneumonia, cystic fibrosis, emphysema and asthma). Representative examples of suitable bronchodilators include but are not limited to the $\beta 2$ agonists (e.g. pirbuterol, epinephrine, salbutamol, salmeterol, levosalbutamol, clenbuterol), the anticholinergics (e.g. ipratropium, oxitropium, tiotropium) and theophylline.

Use of the alginate oligomers and the antibiotic in combination or conjunction with corticosteroids may also be beneficial in the medical uses of the invention, in the treatment of respiratory diseases associated with MDR bacteria especially (which may include COPD, COAD, COAP, pneumonia, cystic fibrosis, emphysema and asthma). Representative examples of suitable corticosteroids include but are not limited to prednisone, flunisolide, triamcinolone, fluticasone, budesonide, mometasone, beclomethasone, amcinonide, budesonide, desonide, fluocinonide, fluocinolone, halcinonide. hydrocortisone, cortisone, tixocortol, prednisolone, methylprednisolone, prednisone, betamethasone, dexamethasone, fluocortolone, aclometasone, prednicarbate, clobetasone, clobetasol, and fluprednidene.

The alginate oligomers and the antibiotic can be used optionally with any other therapeutically active agent it may be desired to use, e.g. an anti-microbial agent, an anti-inflammatory agent (e.g. an anti-inflammatory steroid), an immunostimulatory agent, a mucosal viscosity reducing agent, a growth inhibitor or an enzyme or an alpha blocker, a bronchodilator or a corticosteroid. The combined use of an alginate oligomer and an antibiotic with a further therapeutically active agent (e.g. an anti-microbial or anti-inflammatory agent, an immunostimulatory agent, a mucosal viscosity reducing agent, a growth inhibitor or an enzyme or an alpha blocker, a bronchodilator or a corticosteroid) may improve the clinical effects of the active agent and this may advantageously allow the dose (e.g. the usual or normal dose) of the further therapeutically active agent to be reduced e.g. it may be used at its normal or usual dose or at a lower dose, for example at up to 50% (or at 50%) of its normal dose.

In the case of medical use, the alginate oligomers and antibiotics of the invention may be administered to the subject in any convenient form or by any convenient means, e.g. by topical, oral, parenteral, enteral, parenteral routes or by inhalation. Preferably the alginate and antibiotics will be administered by topical, oral or parenteral routes or by inhalation. The alginate oligomers and antibiotics need not be in the same composition and need not be administered via the same route.

The skilled man will be able to formulate the alginate oligomers and the antibiotics of the invention into pharmaceutical compositions that are adapted for these routes of administration according to any of the conventional methods known in the art and widely described in the literature.

The present invention therefore also provides a pharmaceutical composition for use in any of the above-mentioned methods or uses comprising an alginate oligomer as defined herein together with at least one pharmaceutically acceptable carrier, diluent or excipient. This composition may also comprise an antibiotic as defined herein.

The present invention therefore also provides a pharmaceutical composition for use in any of the above-mentioned methods or uses comprising an antibiotic as defined herein together with at least one pharmaceutically acceptable carrier, diluent or excipient. This composition may also comprise an alginate oligomer as defined herein.

The invention also provides products (e.g. a pharmaceutical kit or a combined ("combination") product) or compositions (e.g. a pharmaceutical composition) wherein the product or composition comprises an alginate oligomer as herein defined and an antibiotic, e.g. selected from the group azithromycin, clarithromycin, dirithromycin, erythromycin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin. Preferably the antibiotic is selected from the group ceftazidime, imipenem/cilastatin, meropenem, aztreonam, oxytetracycline, colistin, azithromycin and ciprofloxacin, preferably it is azithromycin. For example, the antibiotic may be selected from amikacin, gentamicin, kanamycin, neomycin, netilmicin, streptomycin, tobramycin, azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin. In particular, antibiotic may selected from ceftazidime, imipenem/cilastatin, meropenem, aztreonam, oxytetracycline, azithromycin, clarithromycin, dirithromycin, erythromycin, roxithromycin, spiramycin and ciprofloxacin, and it is particularly preferred that the antibiotic is selected from ceftazidime, imipenem/cilastatin, meropenem, aztreonam, azithromycin, clarithromycin, dirithromycin, erythromycin, roxithromycin, spiramycin and ciprofloxacin. More preferably the antibiotic is selected from aztreonam, azithromycin, clarithromycin, dirithromycin, erythromycin, roxithromycin, spiramycin and ciprofloxacin. In other embodiments the antibiotic used is not tobramycin, amikacin and/or colistin. In other embodiments the antibiotic used is not an aminoglycoside or a polypeptide antibiotic. In other embodiments the antibiotic used is not an antibiotic that has a positive charge under the conditions in which it will be used with the alginate oligomer, e.g. antibiotics with at least 3, e.g. at least 4, 5, 6 or 7 amino (—$NH_2$) groups. These products and compositions are specifically contemplated as for use in the methods of the invention. The products and compositions can be pharmaceutical or non-pharmaceutical. Therefore the products and compositions of this aspect of the invention can be used in any of the methods of the invention.

As discussed above, the alginate oligomers and the antibiotics proposed for use according to the invention may be used in combination with each other, for example to be administered together, in a single pharmaceutical formulation or composition, or separately (i.e. for separate, sequential or simultaneous administration). Thus, the alginate oligomers and the antibiotics of the invention may be combined, e.g. in a pharmaceutical kit or as a combined ("combination") product.

Thus as noted above, further aspects of the present invention provide products containing an alginate oligomer and an antibiotic as a combined preparation for the uses defined herein. Such products may optionally further contain a further active agent.

The use of alginate oligomers as herein defined to manufacture such pharmaceutical products and pharmaceutical compositions for use in the medical methods of the invention is also contemplated.

Further active agents may also be incorporated. The above and following discussion of additional active agents and excipients and the like is directly applicable in its entirety to this aspect of the invention.

The active ingredient may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, solutions, syrups, aerosols (as a solid or in a liquid medium), sprays (e.g. nasal sprays), compositions for use in nebulisers ointments, soft and hard gelatine capsules, suppositories, sterile injectable solutions, sterile packaged powders, and the like. Sterile inhalable compositions are of particular note for use in the treatment of respiratory diseases associated with MDR bacteria (which may include COPD, COAD, COAP, pneumonia, cystic fibrosis, emphysema and asthma).

Examples of suitable carriers, excipients, and diluents are lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, and the like. Additional therapeutically active agents may be included in the pharmaceutical compositions, as discussed above in relation to combination therapies above.

In some instances it may be beneficial to administer the alginate oligomers and/or the antibiotics as defined herein to animals, e.g. to promote weight gain/growth. Administration can be achieved in the form of the pharmaceutical compositions described above, but conveniently the alginate oligomers and/or the antibiotics as defined herein may be used as a conventional feed additive, i.e. a compound that is added to animal feed in small, nutritionally inconsequential amounts. The use of feed additives in animal feeds is well established and it would be entirely routine for a skilled man to determine and use appropriate amounts of the alginates of the invention to achieve the desired effects, e.g. weight gain/growth.

The relative content of the alginate oligomer and the antibiotic can vary depending on the dosage required and the dosage regime being followed and this will depend on the subject to be treated and the location and identity of the MDR bacterium, and/or the constituents of the contamination or population comprising the MDR bacterium. Preferably, the composition will comprise an amount of alginate oligomer and an amount of antibiotic that will provide a measurable reduction in the resistance (or measurable increase in susceptibility or measurable decrease in tolerance) to the antibiotic displayed by the bacterium e.g. an amount of alginate oligomer that will at least double, at least quadruple, at least octuple, at least sexdecuple or at least duotrigecuple the susceptibility of the MDR bacterium, to the antibiotic. Put in a different way, the composition will comprise an amount of alginate oligomer and an amount of antibiotic that will provide a measurable treatment of the infection being targeted. Preferably the composition or product will comprise sufficient alginate oligomer that upon administration to a subject or application to a location, the local concentration of the oligomer will be at least 2%, preferably at least 4%, 6% or 8% and most preferably at least 10% (weight by volume). The antibiotic preferably will be present in an amount that is sufficient to provide a local concentration of at least 0.03125, 0.0625, 0.125, 0.25, 0.5, 1, 2, 4, 8, 16, 64, 128, 256, 512, 1024, 2048 or 4096 μg/ml. The skilled man would know that the amounts of alginate oligomer and/or antibiotic can be reduced if a multiple dosing regime is followed or increased to minimise the number of administrations or applications.

The compositions and products of this aspect will typically comprise between 1% and 99%, 5% and 95%, 10% and 90% or 25% and 75% alginate oligomer and 1% and 99%, 5% and 95%, 10% and 90% or 25% and 75% antibiotic, allowance being made for other ingredients.

Parenterally administrable forms, e.g., intravenous solutions, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the biopolymers and which will not interfere with the manufacture, storage or use of products.

For topical administration the alginate oligomer and/or the antibiotic can be incorporated into creams, ointments, gels, transdermal patches and the like. The alginate oligomers and/or the antibiotic can also be incorporated into medical dressings, for example wound dressings e.g. woven (e.g. fabric) dressings or non-woven dressings (e.g. gels or dressings with a gel component). The use of alginate polymers in dressings is known, and such dressings, or indeed any dressings, may further incorporate the alginate oligomers of the invention.

Accordingly, in a further specific embodiment, the invention further provides a wound dressing comprising an alginate oligomer (which may be any alginate oligomer as herein defined) and/or an antibiotic (which may be any antibiotic as herein defined) for use, where appropriate, in the treatments and methods of the invention.

Further topical systems that are envisaged to be suitable are in situ drug delivery systems, for example gels where solid, semi-solid, amorphous or liquid crystalline gel matrices are formed in situ and which may comprise the alginate oligomer and/or the antibiotic. Such matrices can conveniently be designed to control the release of the alginate oligomer and/or the antibiotic from the matrix, e.g. release can be delayed and/or sustained over a chosen period of time. Such systems may form gels only upon contact with biological tissues or fluids. Typically the gels are bioadhesive. Delivery to any body site that can retain or be adapted to retain the pre-gel composition can be targeted by such a delivery technique. Such systems are described in WO 2005/023176.

For application to oral, buccal and dental surfaces, toothpastes, dental gels, dental foams and mouthwashes are mentioned specifically. Thus, in one particular aspect is included an oral health care, or oral hygiene, composition, comprising an alginate oligomer and an antibiotic (which may be any alginate oligomer or antibiotic as defined herein), particularly a mouthwash, toothpaste, dental gel or dental foam for use, where appropriate, in the treatments and methods of the invention.

Inhalable compositions are also of note. The formulation of compositions suitable for inhalation is routine for the skilled man and has long been standard practice in the treatment of respiratory diseases. Inhalable compositions may, for instance, take the form of inhalable powders, solutions or suspensions. The skilled man would be able to select the most appropriate type of delivery system for his needs and be able to prepare a suitable formulation of the alginates and/or antibiotics of the invention for use in that system. Propellant-free nebulisable solutions and inhalable powder formulations are particularly preferred.

As noted above, a preferred composition of the invention is a debridement composition that is used in a debridement process to remove a colony or population comprising an MDR bacterium, for example from a tissue. Typically such a composition will be liquid, but gels, gel-sols, or semi-solid compositions might be used. The composition might be used to debride the colony/population (e.g. by application to the tissue under pressure) and/or may be used to bathe the tissue before, during and/or after debridement by other means such as by surgical, mechanical or chemical processes. The skilled person is readily able to formulate debridement compositions in accordance with the invention.

In the case of an MDR bacterium on an inanimate surface on in an inanimate material, the alginate oligomer and/or antibiotic may be applied to the surface or material to be treated in any convenient composition or formulation, or by any convenient means. Thus the alginate oligomer and/or antibiotic may be in liquid, gel, gel-sol, semi-solid or solid form (e.g. solutions, suspensions, homogenates, emulsions, pastes, powders, aerosols, vapours). Typically the compositions for treating such inanimate surfaces or materials will be a non-pharmaceutically acceptable composition. The choice of composition form will be dictated by the identity of the MDR bacterium on the surface or in the material and location of the surface or material. For instance, if the location is a fluid line it might be convenient to apply a fluid composition. It might also be preferred to use a composition that persists on the surface or in the part of the fluid line to be treated but that will not leach into the fluid of normal use, e.g. an adhesive gel. The skilled person is readily able to prepare suitable compositions from his common general knowledge. For instance, the alginate oligomer and/or antibiotic may be added to a paint formulation and applied to the surface to be treated, e.g. a boat hull or other part of a boat's structure that is exposed to water, or to a building or any part thereof, a tank (e.g. a storage or processing tank) or indeed to any part of any industrial machinery. Such compositions may conveniently also comprise a further anti-microbial agent, as described above, e.g. an antibiotic, chlorine bleach, TCP, ethanol, Virkon™, povidone-iodine, silver compounds, antimicrobial surfactants, etc. As the compositions need not be pharmaceutically acceptable, harsher antimicrobials can be used subject to considerations of surface damage, environmental contamination, user safety and contamination of the treated surface and interaction with the other components of the composition.

The compositions of the invention may be formulated so as to provide quick, sustained or delayed release of the active ingredient after administration to the subject/surface by employing procedures well known in the art. Adhesive compositions are also preferred. Adhesive, sustained and/or delayed release formulations may be particularly convenient.

In a further aspect the invention provides products susceptible to contamination/colonisation by MDR bacteria whose susceptible surfaces have been pretreated with an alginate oligomer and an antibiotic as defined herein.

By "pretreated" it is meant that the susceptible surface is exposed to an alginate oligomer and/or an antibiotic prior to an exposure to an MDR bacterium and that the alginate oligomer and/or antibiotic persists on the surface for a duration sufficient to prevent contamination/colonisation by an MDR bacterium for an appreciable duration of time. Preferably the alginate oligomer and/or the antibiotic will persist for substantially the useful life of the surface, e.g. the pretreatment results in a substantially permanent coating of an alginate oligomer and/or an antibiotic. Thus a pre-treated surface/product is one to which the alginate olgimer and/or antibiotic is applied and on which it remains. Such a product/surface may be a coated product/surface.

Non-limiting examples of products and surfaces susceptible to contamination/colonisation by MDR bacteria are described above. Particular mention may be made of medical devices (e.g. endotracheal or tracheostomy tubes) and food or drink processing, storage or dispensing equipment. Pretreatment can be achieved by any convenient means, for example any form of applying the alginate oligomer and/or antibiotic to the surface, notably coating the surface, e.g. spray drying, polymer coating with a polymer incorporating the alginate oligomer and/or antibiotic, and painting, varnishing or lacquering with paint, varnish or lacquer formulations containing the alginate oligomer and/or antibiotic. Such a "coating" composition (e.g. a paint, varnish or lacquer) containing an alginate oligomer and/or antibiotic represents a further aspect of the present invention. Alternatively, the alginate oligomer and/or antibiotic can be incorporated into the material from which the object or its susceptible parts are manufactured. This approach is suited to objects, or constituent parts thereof, manufactured from polymers such as plastics and silicones, e.g. the medical and surgical devices described above. Products comprising an inanimate surface comprising an alginate oligomer and/or antibiotic coating or coating composition, or incorporating an alginate oligomer and/or antibiotic are therefore contemplated. Non-limiting examples of such products and surfaces are described above. Of particular note are medical and surgical devices. This may include any kind of line, including catheters (e.g. central venous and urinary catheters), prosthetic devices e.g., heart valves, artificial joints, false teeth, dental crowns, dental caps and soft tissue implants (e.g. breast, buttock and lip implants). Any kind of implantable (or "in-dwelling") medical device is included (e.g. stents, intrauterine devices, pacemakers, intubation tubes (e.g. endotracheal or tracheostomy tubes), prostheses or prosthetic devices, lines or catheters). Further products include food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

The invention will be further described with reference to the following non-limiting Examples.

EXAMPLES

Example 1

Effect of G-Block Alginate Oligomers on the Minimum Inhibitory Concentrations of Various Antibiotics for Various Bacterial Strains Materials and Methods
Bacterial Strains Used:
 PA01 *Pseudomonas aeruginosa* ATCC 15692
 *Pseudomonas aeruginosa* ATCC 39324, mucoid type strain (R79)*

Pseudomonas aeruginosa CFA 24-1, clinical mucoid strain (R80)*
Pseudomonas aeruginosa MDR R22 from China (V1)*
Pseudomonas aeruginosa MDR 301 from Poland (V2)*
Klebsiella pneumoniae KP05 506 from India (V3)*
Acinetobacter baumannii MDR ACB from Libya (V4)*
*Non-official labels assigned for internal identification purposes only.
Abbreviations used: Pseudomonas aeruginosa, (PA); Klebsiella pneumoniae (KP); Acinetobacter baumannii (ACB)
Media and Bacterial Strains Used:

Following retrieval from −80° C. storage, bacterial colonies were grown on blood agar with 5% sheep blood and were used to inoculate tryptone soya broth (TSB) for overnight growth. Antibiotics were diluted in cation-adjusted Mueller-Hinton broth (CAMHB) or CAMHB with G-fragments (Oligo CF-5/20 90-95% G residues) at 2%, 6% or 10%. Antibiotics were pharmaceutical grade purchased from Sigma-Aldrich. OligoG CF-5/20 G-fragments were provided by Algipharma AS, Norway.
Minimum Inhibitory Concentration assay (Jorgensen et al., Manual of Clinical Microbiology, 7th ed. Washington, D.C.: American Society for Microbiology, 1999; 1526-43):

Overnight bacterial cultures as described above were diluted in sterile water until the OD625 was between 0.08 and 0.10 to confirm that the cell density was equivalent to 0.5 McFarland standard.

In experiments with single antibiotics, two-fold antibiotic serial dilutions were prepared in CAMHB or CAMHB supplemented G-fragments (Oligo CF-5/20 90-95% G residues) at 0%, 2%, 6% or 10% and were placed in duplicate wells of flat-bottom 96-well microtiter plates (100 µl in each well).

In experiments with two antibiotics (ceftazidime and azithromycin or ciprofloxacin and azithromycin), two-fold antibiotic serial dilutions were prepared in CAMHB or CAMHB supplemented with azithromycin at either 1, 2, 4, or 8 µg/ml and G-fragments at either 0%, 2%, 6% or 10% and were placed in duplicate wells of flat-bottom 96-well microtiter plates (100 µl in each well).

Bacterial cultures at 0.5 McFarland standard were diluted ten-fold in CAMHB and 5 µl added to the microtiter plates containing the antibiotic serial dilutions. Plates were wrapped in parafilm and incubated at 37° C. for 16-20 hours. MIC values for each antibiotic/antibiotic combination were determined as the lowest concentration at which there was no visible growth. Results are shown in Tables 1, 2 and 3.

TABLE 1

Minimum inhibitory concentration (MICs) of different antibiotics for different Pseudomonas aeruginosa, Klebsiella pneumoniae and Acinetobacter baumannii strains in the presence of varying concentrations of OligoCF-5/20 (0-10%). (MIC values are expressed in $\mu g\ ml^{-1}$).

| Antibiotic | | PA01 PA | R79 Mucoid PA | R80 Mucoid PA | V1* MDR R22 PA (China) | V2* MDR 301 PA (Poland) | V3* KP05 506 (India) | V4* ACB (Libya) |
|---|---|---|---|---|---|---|---|---|
| Oxytetracycline | 0 G | 8 | 8 | 8 | ND | ND | ND | ND |
| | +2% G | 4 | 4 | 8 | | | | |
| | +6% G | 4 | 4 | 4 | | | | |
| | +10% G | 4 | 2 | 4 | | | | |
| Azithromycin | 0 G | 128 | 128 | 256 | 64 | 64 | 32 | 8 |
| | +2% G | 64 | 64 | 128 | 64 | 64 | 16 | 2 |
| | +6% G | 16 | 16 | 64 | 64 | 32 | 16 | <0.25 |
| | +10% G | 4 | 4 | 8 | 32 | 16 | 8 | <0.25 |
| Ciprofloxacin | 0 G | 0.125 | 0.125 | 1 | 16 | 16 | 128 | 64 |
| | +2% G | 0.0625 | 0.0625 | 0.125 | 16 | 16 | 128 | 32 |
| | +6% G | 0.0625 | 0.03125 | 0.125 | 8 | 8 | 128 | 16 |
| | +10% G | 0.03125 | 0.03125 | 0.125 | 4 | 8 | 128 | 16 |
| Primaxin (Imipenem/ cilastatin) | 0 G | <1 | <1 | <1 | 128 | 512 | 32 | <1 |
| | +2% G | <1 | <1 | <1 | 128 | 256 | 64 | <1 |
| | +6% G | <1 | <1 | <1 | 64 | 256 | 64 | <1 |
| | +10% G | <1 | <1 | <1 | 32 | 128 | 64 | <1 |
| Meropenem | 0 G | 2 | <1 | <1 | 32 | 64 | 64 | <4 |
| | +2% G | 2 | <1 | <1 | 32 | 64 | 64 | <4 |
| | +6% G | <1 | <1 | <1 | 16 | 128 | 128 | <4 |
| | +10% G | <1 | <1 | <1 | 4 | 128 | 128 | <4 |
| Ceftazidime | 0 G | <1 | <1 | <1 | 128 | 32 | >1024 | 512 |
| | +2% G | <1 | <1 | <1 | 64 | 16 | >1024 | 512 |
| | +6% G | <1 | <1 | <1 | 32 | 8 | >1024 | 512 |
| | +10% G | <1 | <1 | <1 | 8 | 4 | >1024 | 256 |
| Aztreonam | 0 G | 8 | 2 | <1 | 32 | 64 | 2048 | 1024 |
| | +2% G | 16 | 2 | <1 | 16 | 16 | 2048 | 512 |
| | +6% G | 4 | <1 | <1 | <4 | 8 | 512 | 256 |
| | +10% G | 2 | <1 | <1 | <4 | 8 | 256 | 128 |

 Indicates increasing MIC values with increase in G-fragment concentration

 Indicates decreasing MIC values with increase in G-fragment concentration

TABLE 2

Minimum inhibitory concentration (MICs) of azithromycin for an MDR *Acinetobacter baumannii* and various strains of *Pseudomonas aeruginosa* and *Klebsiella pneumoniae* in the presence of varying concentrations of OligoCF-5/20 (0-10%).

| Antibiotic | | PA01 PA | R79 Mucoid PA | R80 Mucoid PA | V1* MDR R22 PA (China) | V2* MDR 301 PA (Poland) | V3* KP05 506 (India) | V4* ACB (Libya) |
|---|---|---|---|---|---|---|---|---|
| Azithromycin | 0 G | 128 | 128 | 256 | 64 | 64 | 32 | 8 |
| | +2% G | 64 | 64 | 128 | 64 | 64 | 16 | 2 |
| | +6% G | 16 | 16 | 64 | 64 | 32 | 16 | <0.25 |
| | +10% G | 4 | 4 | 8 | 32 | 16 | 8 | <0.25 |

 Indicates increasing MIC values with increase in G-fragment concentration

 Indicates decreasing MIC values with increase in G-fragment concentration

TABLE 3

Minimum inhibitory concentrations (MICs) of two antibiotics in combinations with each other (azithromycin with either ceftazidime or ciprofloxacin) for multi drug resistant (MDR) strains of *Pseudomonas aeruginosa* and *Acinetobacter baumannii* in the presence of varying concentrations of OligoCF-5/20 (0-10%) (MIC values are expressed in µg ml⁻¹).

| Antibiotic | | V1* MDR R22 PA (China) | V4* ACB (Libya) |
|---|---|---|---|
| Ceftazidime with azithromycin at 8 µg/ml | 0 G | 256 | 512 |
| | +2% G | 128 | <8 µg/ml Az |
| | +6% G | 32 | <8 µg/ml Az |
| | +10% G | 16 | <8 µg/ml Az |
| Ceftazidime with azithromycin at 4 µg/ml | 0 G | 128 | 1024 |
| | +2% G | 128 | <4 µg/ml Az |
| | +6% G | 64 | <4 µg/ml Az |
| | +10% G | 8 | <4 µg/ml Az |
| Ceftazidime with azithromycin at 2 µg/ml | 0 G | 128 | 1024 |
| | +2% G | 64 | 256 |
| | +6% G | 32 | 2 |
| | +10% G | 16 | <1 Cf |
| Ceftazidime with azithromycin at 1 µg/ml | 0 G | 128 | 1024 |
| | +2% G | 64 | 512 |
| | +6% G | 16 | 128 |
| | +10% G | 16 | <1 Cf |
| Ciprofloxacin with azithromycin at 8 µg/ml | 0 G | 16 | 128 |
| | +2% G | 16 | <8 µg/ml Az |
| | +6% G | 16 | <8 µg/ml Az |
| | +10% G | <8 µg/ml Az | <8 µg/ml Az |
| Ciprofloxacin with azithromycin at 4 µg/ml | 0 G | 16 | 128 |
| | +2% G | 16 | 64 Cpr, 4 Az |
| | +6% G | 8 | <4 µg/ml Az |
| | +10% G | 4 | <4 µg/ml Az |
| Ciprofloxacin with azithromycin at 2 µg/ml | 0 G | 32 | 128 |
| | +2% G | 16 | <0.25 Cpr 2Az |
| | +6% G | 16 | <0.25 Cpr |
| | +10% G | 8 | <0.25 Cpr |
| Ciprofloxacin with azithromycin at 1 µg/ml | 0 G | 16 | 64 |
| | +2% G | 16 | 32 |
| | +6% G | 8 | <0.25 Cpr |
| | +10% G | 8 | <0.25 Cpr |

 Indicates increasing MIC values with increase in G-fragment concentration

 Indicates decreasing MIC values with increase in G-fragment concentration

Results and Discussion

In general, treatment of planktonically growing MDR strains of *Pseudomonas aeruginosa*, *Klebsiella pneumoniae* and *Acinetobacter baumannii* strains with increasing concentrations of OligoG CF-5/20 lowered the MIC values of the antibiotics used (Tables 1, and 2). Oxytetracycline, azithromycin and ciprofloxacin were all shown to have decreasing MICs with increasing amounts of OligoG CF-5/20 used. Thus, in the case of these antibiotics, the data appear to show that alginate oligomers may potentiate their effects. The antibiotics tested include antibiotics common in the treatment of cystic fibrosis.

The magnitude of the effect was most pronounced for the MDR strain *Pseudomonas aeruginosa* strain R22, although all strains studied responded to treatment with the alginate oligomers and azithromycin. The results also show alginate oligomers potentiate the antibiotic azithromycin with all strains tested. Such an effect may be seen with azithromycin alone or in combination with other antibiotics.

More specifically, for the MDR *Pseudomonas* strains, primaxin (a combination of imipenem and cilastatin), azithromycin, ceftazidime, ciprofloxacin and aztreonam were all more effective when used in combination with the alginate oligomers. Two antibiotics in conjunction with alginate oligomers were more effective against KP05 506, namely, azithromycin and aztreonam, but the data from experiments using primaxin and meropenem is inconclusive. In combination with alginate oligomers, azithromycin, ceftazidime, ciprofloxacin and aztreonam showed a more positive effect on the *Acinetobacter baumannii* isolate.

The effects of azithromycin in conjunction with either ceftazidime or ciprofloxacin in the presence of alginate oligomers on the MDR R22 PA strain and the MDR *Acinetobacter baumannii* isolate were tested and the results can be seen in Table 3. In all cases MIC values of the ceftazidime or ciprofloxacin in the antibiotic combinations were reduced by various concentrations of alginate oligomer.

Example 2

The study described in Example 1 was repeated with the following strains of bacteria and antibiotics as detailed in Tables 4, 5 and 6.

Bacterial Strains
PA01 *Pseudomonas aeruginosa* ATCC 15692 (E77)
R79* Mucoid *Pseudomonas aeruginosa* ATCC 39324 ISOLATION: sputum from a cystic fibrosis patient, Boston, Mass.
R80* Mucoid *Pseudomonas aeruginosa* CFA 24-1 (CLINICAL ISOLATE from a CF patient.)
V1* R22 PSA (China) *Pseudomonas aeruginosa*
V2* MDR 301 PSA (Poland) *Pseudomonas aeruginosa*
V3* KP05 506 (India) *Klebsiella pneumoniae.*
V4* MDR ACB (Libya) *Acinetobacter baumannii*
V5* AIM-1 *E. coli*
V9* (Egypt) *Acinetobacter baumannii*
V10* (Egypt) *Acinetobacter lwoffii*
V11* 5702 (Wales) *E. coli*
V12* 5725 (Wales) *Klebsiella pneumoniae*
V22* 6056 *Acinetobacter*
V23* 1322 *Burkholderia cepacia*

*Non-official labels assigned for internal identification purposes only.

TABLE 4

Minimum inhibitory concentration (MICs) of different macrolide antibiotics for various strains of *Pseudomonas aeruginosa*, *Klebsiella pneumoniae*, *Acinetobacter baumannii* and *E. coli* displaying MDR phenotypes in the presence of varying concentrations of OligoCF-5/20 (0-10%). (MIC values are expressed in μg ml$^{-1}$).

| Antibiotic and MIC value μg/ml | % G | PA01 non MDR Pseud aerug | R79 non MDR Pseud aerug (muc.) | R80 non MDR Pseud aerug (muc.) | V1 MDR Pseud aerug (China) | V2 MDR Pseud aerug (Pol.) | V3 MDR Kleb pneum (India) | V4 MDR Acin baum (Libya) | V5 MDR *E. coli* |
|---|---|---|---|---|---|---|---|---|---|
| Erythromycin | 0 G | 128 | 128 | 512 | 128 | 128 | 1024 | 8 | 4 |
| | +2% G | 64 | 64 | 512 | 128 | 128 | 1024 | 2 | 4 |
| | +6% G | 64 | 32 | 128 | 64 | 64 | 1024 | ≤1 | ≤1 |
| | +10% G | 16 | 2 | 32 | 32 | 16 | 1024 | ≤1 | ≤1 |
| Clarithromycin | 0 G | 256 | 256 | 1024 | 256 | 512 | 256 | 8 | 4 |
| | +2% G | 128 | 128 | 512 | 128 | 256 | 256 | 4 | 4 |
| | +6% G | 64 | 32 | 256 | 64 | 128 | 256 | ≤1 | 2 |
| | +10% G | 32 | 4 | 64 | 32 | 32 | 128 | ≤1 | ≤1 |
| Spiramycin | 0 G | >1024 | >1024 | >1024 | >1024 | >1024 | 1024 | 512 | 32 |
| | +2% G | >1024 | >1024 | >1024 | >1024 | >1024 | 1024 | 64 | 32 |
| | +6% G | 1024 | 1024 | 1024 | 1024 | >1024 | 1024 | 64 | 16 |
| | +10% G | 512 | 256 | 1024 | 512 | 1024 | 512 | 32 | 8 |

 Indicates decreasing MIC values with increase in G-fragment concentration

 Indicates increasing MIC values with increase in G-fragment concentration

TABLE 5

Minimum inhibitory concentration (MICs) of different antibiotics for strains of *Burkholderia cepacia*, *Klebsiella pneumoniae*, *Acinetobacter baumannii*, *Acinetobacter lwoffii* and *E. coli* displaying MDR phenotypes in the presence of varying concentrations of OligoCF-5/20 (0-10%). (MIC values are expressed in µg ml$^{-1}$).

| Antibiotic and MIC value µg/ml | % G | V23 MDR Burk cep | V22 MDR Acin. lwoff | V9 MDR Acin. baum | V10 MDR Acin. lwoff | V11 MDR E. coli | V12 MDR Kleb pneu |
|---|---|---|---|---|---|---|---|
| Oxytetracycline | 0 G | 256 | 2 | 2 | 0.5 | 0.5 | 1 |
|  | +2% G | 128 | 2 | 2 | 0.5 | 1 | 1 |
|  | +6% G | 128 | 2 | 1 | 0.5 | 0.5 | 1 |
|  | +10% G | 32 | 8 | 4 | 0.25 | 0.5 | 1 |
| AZACTAM (Aztreonam) | 0 G | >512 | 256 | >512 | 32 | 256 | 256 |
|  | +2% G | >512 | 128 | 512 | 16 | 256 | 512 |
|  | +6% G | 512 | 64 | 256 | 4 | 256 | 128 |
|  | +10% G | 128 | 32 | 128 | 1 | 256 | 64 |
| Ciprofloxacin | 0 G | 64 | <0.25 | 64 | 0.5 | 128 | 64 |
|  | +2% G | 64 | <0.25 | 32 | 0.5 | 64 | 64 |
|  | +6% G | 64 | <0.25 | 32 | 0.25 | 128 | 256 |
|  | +10% G | 32 | <0.25 | 32 | 0.25 | 128 | 256 |
| PRIMAXIN (Imipenem/ Cilastatin) | 0 G | 32 | 8 | 1 | <0.5 | <0.5 | <0.5 |
|  | +2% G | 32 | 8 | 2 | <0.5 | <0.5 | <0.5 |
|  | +6% G | 32 | 8 | <0.5 | <0.5 | <0.5 | <0.5 |
|  | +10% G | 8 | 4 | <0.5 | <0.5 | <0.5 | <0.5 |
| Meropenem | 0 G | 64 | 256 | 16 | 1 | <0.25 | <0.25 |
|  | +2% G | 64 | 128 | 8 | 0.5 | <0.25 | <0.25 |
|  | +6% G | 32 | 128 | 8 | <0.25 | <0.25 | <0.25 |
|  | +10% G | 8 | 64 | 4 | <0.25 | <0.25 | <0.25 |
| Ceftazidime | 0 G | 64 | 16 | <512 | 2 | 128 | 64 |
|  | +2% G | 32 | 16 | 512 | 2 | 64 | 64 |
|  | +6% G | 8 | 4 | 512 | <0.5 | 32 | 16 |
|  | +10% G | <0.5 | 2 | 256 | <0.5 | 64 | 16 |
| Azithromycin | 0 G | 128 | <0.25 | 16 | <0.25 | 32 | 32 |
|  | +2% G | 64 | <0.25 | 4 | <0.25 | 16 | 8 |
|  | +6% G | 16 | <0.25 | 0.5 | <0.25 | 16 | 32 |
|  | +10% G | 4 | <0.25 | <0.25 | <0.25 | 32 | 32 |
| Erythromycin | 0 G | 512 | <0.5 | 8 | <0.5 | 512 | 512 |
|  | +2% G | 256 | <0.5 | 4 | <0.5 | 256 | 256 |
|  | +6% G | 128 | <0.5 | 1 | <0.5 | 256 | 512 |
|  | +10% G | 16 | <0.5 | <0.5 | <0.5 | 256 | 512 |

TABLE 5-continued

Minimum inhibitory concentration (MICs) of different antibiotics for strains of *Burkholderia cepacia*, *Klebsiella pneumoniae*, *Acinetobacter baumannii*, *Acinetobacter lwoffii* and *E. coli* displaying MDR phenotypes in the presence of varying concentrations of OligoCF-5/20 (0-10%). (MIC values are expressed in µg ml$^{-1}$).

| Clarithromycin | 0 G    | 512   | —  | 16  | <0.5 | 512 | 512 |
|----------------|--------|-------|----|-----|------|-----|-----|
|                | +2% G  | 256   | —  | 4   | <0.5 | 128 | 256 |
|                | +6% G  | 128   | —  | 2   | <0.5 | 256 | 256 |
|                | +10% G | 32    | —  | 1   | <0.5 | 256 | 512 |
| Spiramycin     | 0 G    | >4096 | <4 | 256 | <4   | 128 | 64  |
|                | +2% G  | 2048  | <4 | 64  | <4   | 64  | 64  |
|                | +6% G  | 2048  | <4 | 32  | <4   | 32  | 32  |
|                | +10% G | 1024  | <4 | 16  | <4   | 32  | 16  |

 Indicates decreasing MIC values with increase in G-fragment concentration

 Indicates increasing MIC values with increase in G-fragment concentration

TABLE 6

Minimum inhibitory concentration (MICs) of different antibiotics for a strain (V23) of *Burkholderia cepacia* in the presence of varying concentrations of OligoCF-5/20 (0-10%). (MIC values are expressed in µg ml$^{-1}$). Results from three separate experiments.

| Strain → <br> Antibiotic and MIC value µg/ml | % G    | Experiment 1 <br> V23 <br> (18-03-10) | Experiment 2 <br> V23 <br> (18-03-10) | Experiment 3 <br> V23 <br> (19-03-10) |
|----------------------------------------------|--------|---------------------------------------|---------------------------------------|---------------------------------------|
| Oxytetracycline                              | 0 G    | >256                                  | >256                                  | >256                                  |
|                                              | +2% G  | 256                                   | >256                                  | 256                                   |
|                                              | +6% G  | 256                                   | 256                                   | 256                                   |
|                                              | +10% G | 128                                   | 128                                   | 256                                   |
| AZACTAM (Aztreonam)                          | 0 G    | >4096                                 | >4096                                 | >4096                                 |
|                                              | +2% G  | >4096                                 | >4096                                 | >4096                                 |
|                                              | +6% G  | 1024                                  | 1024                                  | 1024                                  |
|                                              | +10% G | 256                                   | 512                                   | 128                                   |

TABLE 6-continued

Minimum inhibitory concentration (MICs) of different antibiotics for a strain (V23) of *Burkholderia cepacia* in the presence of varying concentrations of OligoCF-5/20 (0-10%). (MIC values are expressed in $\mu g \, ml^{-1}$). Results from three separate experiments.

| Antibiotic | G conc. | Exp 1 | Exp 2 | Exp 3 |
|---|---|---|---|---|
| PRIMAXIN (Imipenem/ Cilastatin) | 0 G | 128 | 256 | 256 |
| | +2% G | 128 | 128 | 256 |
| | +6% G | 64 | 128 | 256 |
| | +10% G | 32 | 64 | 128 |
| Meropenem | 0 G | 128 | 128 | 128 |
| | +2% G | 128 | 128 | 64 |
| | +6% G | 64 | 128 | 128 |
| | +10% G | 64 | 128 | 64 |
| Ceftazidime | 0 G | 128 | 64 | 64 |
| | +2% G | 64 | 64 | 32 |
| | +6% G | 16 | 32 | 16 |
| | +10% G | 8 | 32 | 4 |
| Azithromycin | 0 G | 64 | 32 | 16 |
| | +2% G | 64 | 32 | 16 |
| | +6% G | 64 | 16 | 16 |
| | +10% G | 32 | 16 | 16 |
| Erythromycin | 0 G | 512 | 256 | >512 |
| | +2% G | 256 | 256 | 128 |
| | +6% G | 128 | 64 | 64 |
| | +10% G | 64 | 64 | 16 |
| Clarithromycin | 0 G | 256 | 128 | 64 |
| | +2% G | 256 | 128 | 512 |
| | +6% G | 128 | 32 | 512 |
| | +10% G | 128 | 16 | 512 |

 Indicates decreasing MIC values with increase in G-fragment concentration

 Indicates increasing MIC values with increase in G-fragment concentration In general, Table 4 validates the results disclosed in Tables 1 and 2 in relation to the effects of OligoG CF-5/20 on the MIC's of macrolide antibiotics in a variety of planktonically growing bacteria. In virtually every combination of bacteria and macrolide, MIC values are reduced by increasing concentrations of OligoG CF-5/20. The results also show alginate oligomers potentiate the effects of the macrolide antibiotics with all bacteria tested. Such an effect may be seen with azithromycin alone or in combination with other antibiotics.

From data presented in Tables 4, 5 and 6 it can been seen that in general increasing concentrations of OligoG CF-5/20 lowered the MIC values of the antibiotics used against MDR strains of *Pseudomonas aeruginosa, Klebsiella pneumoniae, Burkholderia cepacia, Acinetobacter lwoffii, Acinetobacter baumannii* and *E. coli*. The antibiotics tested include antibiotics common in the treatment of cystic fibrosis. Aztreonam, primaxin (a combination of imipenem and cilastatin), ciprofloxacin, meropenem, ceftazidime, azithromycin, erythromycin, clarithromycin, and spiramycin were all shown to have decreasing MICs with increasing amounts of OligoG CF-5/20 used. Thus, in the case of these antibiotics, the data appear to show that alginate oligomers may potentiate their effects. The macrolides display the greatest reduction in MICs with increasing amounts of OligoG CF-5/20 used. The magnitude of the effect was most pronounced for the *Burkholderia* tested and *Acinetobacter baumannii* strain V9 and in these strains every antibiotic tested showed a reduction in MIC values with increasing concentrations of alginate oligomer.

Table 6 further validates the results with *Burkholderia* presented in Table 5. This antibiotic potentiating effect seen with alginate oligomers and *Burkholderia* is of clinical significance as these organisms are associated with human and animal disease and are difficult to treat on account of their tendency to display antibiotic resistance.

Example 3

The study described in Example 1 was repeated with the following strains of *Acinetobacter baumannii*, antibiotics and M-block alginate oligomer in place of OligoG CF-5/20 as detailed in Table 7. The M-block oligomer is 100% M with a DPn of 15 to 18.

MIC-Assay

G-block alginates (OligoG CF-5/20) were dissolved in Mueller-Hinton broth (Lab M limited, LAB114 Mueller-Hinton broth) to 1.25 times of the desired assay concentrations (2, 6 and 10%). Antibiotics were dissolved in Mueller-Hinton broth and Mueller-Hinton broth with G-block alginate at a concentration of 1.25 times the highest desired assay concentrations. Antibiotics were pharmaceutical grade purchased from Sigma-Aldrich. OligoG CF-5/20 G-fragments were provided by Algipharma AS, Norway.

TABLE 7

Minimum inhibitory concentration (MICs) of different antibiotics for a strain of *Acinetobacter baumannii* displaying an MDR phenotype and a strain of *Acinetobacter baumannii* displaying an non-MDR phenotype in the presence of varying concentrations of M-block oligomer (0-10%). (MIC values are expressed in $\mu g \ ml^{-1}$).

| Antibiotic and MIC value µg/ml | M block concentration | V4 MDR Acin baum (Libya) | V19 non MDR Acin. baum |
|---|---|---|---|
| Aztreonam | 0 M | 2048 | 64 |
|  | +2% M | 512 | 32 |
|  | +6% M | 256 | 8 |
|  | +10% M | 64 | 8 |
| Ciprofloxacin | 0 M | 64 | 64 |
|  | +2% M | 64 | 32 |
|  | +6% M | 64 | 16 |
|  | +10% M | 128 | 128 |
| Meropenem | 0 M | 16 | 8 |
|  | +2% M | 32 | 4 |
|  | +6% M | 16 | 2 |
|  | +10% M | 8 | 1 |
| Azithromycin | 0 M | 8 | 32 |
|  | +2% M | 8 | 16 |
|  | +6% M | 8 | 16 |
|  | +10% M | 2 | 16 |

 Indicates decreasing MIC values with increase in G-fragment concentration

 Indicates increasing MIC values with increase in G-fragment concentration The results displayed in Table 7 show that M-block oligomers are, like OligoG CF-5/20, also effective in lowering MIC values for a number of different antibiotics (including a macrolide) in MDR and non-MDR strains of *Acinetobacter baumannii*.

Example 4

Further MIC assays were conducted with the various strains and antibiotics recited in Tables 8 to 11 using the following protocol.

Two-fold serial dilutions of antibiotics were made in Mueller-Hinton with different concentrations of G-block alginate, and the solutions were placed in four parallel wells in Nunc 384-well micro plates (30 µl per well in Nunc 242757 microplates). A group of 8 wells with no addition of antibiotics for each G-block concentration was included on each micro plate as growth reference.

Frozen stock cultures were made from over night cultures in TSB-broth for all strains by addition of glycerol to 15% concentration prior to freezing at −80° C. At the day of analysis, overnight TSB cultures (6 ml in 50 ml tube tilted to 45-degrees angle, 200 rpm, 2.5 cm amplitude, 37° C.) were diluted in TSB until the OD600 was 0.10, and further diluted 1:40 in Mueller-Hinton broth. Each well in the 384-well assay plates was inoculated with 7.5 µl of the diluted culture. The microplates were placed in plastic bags and incubated at 37° C. The optical density at 600 nm in the microwells was measured after approximately 18 hours of incubation, and the relative growth yield in each well was calculated based on the growth in the reference groups. The MIC value was set to the highest concentration giving less than 30% growth in all 4 parallel wells within the sample groups. The microplates were further incubated for 8 hours, and optical density in the cultures was measured once more for confirmation of the estimated MIC-values.

Results

In each of Tables 8 to 11 there is a main table of basic data, and a secondary table which is a representation of the overall effect of the OligoCF-5/20 on the MIC value for each particular bacteria and antibiotic combination. In the secondary table a dark shaded box represents an overall reduction in the MIC value; a hatched boxed represents an overall increase in the MIC value; M indicates that all of the MIC values were greater than the maximum concentration of antibiotic used; L indicates that all of the MIC values were less than the minimum concentration of antibiotic used; NE indicates no effect on the MIC values was observed; ND indicates that the particular combination of antibiotic and bacteria was not tested.

Table 8. Minimum inhibitory concentration (MICs) of different antibiotics for strains of *Burkholderia cepacia* and *Pseudomonas aeruginosa* displaying MDR phenotypes in the presence of varying concentrations of OligoCF-5/20 (0-10%). (MIC values are expressed in µg ml$^{-1}$).

Table 9. Minimum inhibitory concentration (MICs) of different antibiotics for strains of *Acinetobacter baumannii* and *Acinetobacter lwoffii* displaying MDR phenotypes in the presence of varying concentrations of OligoCF-5/20 (0-10%). (MIC values are expressed in µg ml$^{-1}$).

Table 10. Minimum inhibitory concentration (MICs) of different antibiotics for strains of *Klebsiella pneumoniae* displaying MDR phenotypes in the presence of varying concentrations of OligoCF-5/20 (0-10%). (MIC values are expressed in µg ml$^{-1}$).

Table 11. Minimum inhibitory concentration (MICs) of different antibiotics for strains of *E. coli* and *Providencia stuartii* displaying MDR phenotypes in the presence of varying concentrations of OligoCF-5/20 (0-10%). (MIC values are expressed in µg ml$^{-1}$).

Table 12. Minimum inhibitory concentration (MICs) of different antibiotics for strains of *Streptococcus oralis* and *Staphylococcus aureus* (MRSA) displaying MDR phenotypes in the presence of varying concentrations of OligoCF-5/20 (0-10%). (MIC values are expressed in µg ml$^{-1}$).

TABLE 8

| Strain | G-block | Azithro-mycin | Erythro-mycin | Roxithro-mycin | Dirithro-mycin | Aztreo-nam | Ceftazi-dime | Imi-penem | Cipro-floxacin | Oxytetra-cycline |
|---|---|---|---|---|---|---|---|---|---|---|
| *Pseudomonas aeruginosa* (MDR 301, PSA, V2) MDR | 0% | 128 | >512 | >512 | >512 | 0.125 | 0.5 | 256 | 1 | 16 |
| | 2% | 64 | >512 | >512 | >512 | 0.125 | 0.125 | 256 | 0.5 | 16 |
| | 6% | 64 | 512 | >512 | 512 | 0.125 | 0.25 | 128 | 0.5 | 8 |
| | 10% | 32 | 512 | >512 | 512 | 0.0625 | 0.125 | 128 | 0.25 | 8 |
| *Pseudomonas aeruginosa* (R22, PSA, V1) MDR | 0% | 128 | >512 | >512 | >512 | 0.125 | >16 | 128 | >8 | >128 |
| | 2% | 32 | 512 | >512 | >512 | 0.125 | >16 | 128 | >8 | >128 |
| | 6% | 32 | 512 | 512 | 512 | 0.0625 | >16 | 64 | >8 | >128 |
| | 10% | 8 | 256 | 256 | 256 | 0.03125 | >16 | 16 | >8 | >128 |
| *Burkholderia cepacia* (1322, V23) MDR | 0% | 64 | 256 | 512 | 256 | >16 | >16 | >16 | >8 | 128 |
| | 2% | 32 | 128 | 512 | 256 | >16 | >16 | 16 | >8 | 128 |
| | 6% | 32 | 128 | 256 | 128 | >16 | 16 | 16 | >8 | 64 |
| | 10% | 8 | 64 | 64 | 64 | >16 | 16 | 16 | >8 | 64 |
| *Burkholderia cepacia* (LMG18941, ATCC-BAA-246) MDR | 0% | 64 | 128 | 256 | 512 | >16 | >16 | >16 | >8 | 32 |
| | 2% | 32 | 128 | 256 | 256 | >16 | 16 | >16 | >8 | 16 |
| | 6% | 16 | 64 | 256 | 256 | >16 | 16 | >16 | >8 | 32 |
| | 10% | 16 | 64 | 128 | 256 | >16 | 16 | >16 | >8 | 32 |

| Strain | Azithro-mycin | Erythro-mycin | Roxithro-mycin | Dirithro-mycin | Aztreo-nam | Ceftazi-dime | Imi-penem | Cipro-floxacin | Oxytetra-cycline |
|---|---|---|---|---|---|---|---|---|---|
| *Pseudomonas aeruginosa* (V2) | | | M | | | | | | |
| *Pseudomonas aeruginosa* (V1) | | | | | | M | | M | M |
| *Burkholderia cepacia* (V23) | | | | | M | | | M | |
| *Burkholderia cepacia* (LMG18941) | | | | | M | | M | M | NE |

TABLE 9

| Strain | G-block | Azithro-mycin | Erythro-mycin | Roxithro-mycin | Dirithro-mycin | Aztreo-nam | Ceftazi-dime | Imi-penem | Cipro-floxacin | Oxytetra-cycline |
|---|---|---|---|---|---|---|---|---|---|---|
| *Acinetobacter lwoffii* (6056, V22) MDR | 0% | <2 | <2 | 4 | <2 | 64 | 8 | 2 | <2 | <2 |
| | 2% | <2 | <2 | <2 | <2 | 32 | 4 | 2 | <2 | <2 |
| | 6% | <2 | <2 | <2 | <2 | 16 | 2 | 2 | <2 | <2 |
| | 10% | <2 | <2 | <2 | <2 | 4 | 2 | <2 | <2 | <2 |
| *Acinetobacter baumannii* (Egypt, V9) MDR | 0% | 4 | 8 | 8 | 4 | >16 | >16 | 2 | >8 | 1 |
| | 2% | <1 | 2 | 4 | <1 | >16 | >16 | <2 | >8 | 0.5 |
| | 6% | <1 | 1 | 4 | <1 | >16 | >16 | 2 | 8 | 1 |
| | 10% | <1 | <1 | 2 | <1 | >16 | >16 | <2 | 8 | 0.5 |
| *Acinetobacter baumannii* (MDR ACB, Libya, V4) | 0% | 16 | 32 | 128 | 64 | 4 | 16 | 2 | 4 | 2 |
| | 2% | 2 | 8 | 32 | 8 | 4 | 8 | 2 | 1 | 2 |
| | 6% | <1 | 4 | 16 | 2 | 1 | 8 | 2 | 1 | 2 |
| | 10% | <1 | 2 | 16 | <1 | 0.5 | 8 | <2 | 0.5 | 1 |
| *Acinetobacter lwoffii* (Egypt, V10) MDR | 0% | <1 | 1 | 4 | <1 | 8 | 2 | <2 | 0.063 | 0.5 |
| | 2% | <1 | <1 | <1 | <1 | 4 | 1 | <2 | 0.031 | 0.5 |
| | 6% | <1 | <1 | <1 | <1 | 2 | 0.25 | <2 | 0.031 | 0.5 |
| | 10% | <1 | <1 | <1 | <1 | 1 | 0.25 | <2 | 0.031 | 0.5 |
| *Acinetobacter lwoffii* (V22) | | L | L | | L | | | | L | L |
| *Acinetobacter baumannii* (V9) | | | | | | M | M | NE | | NE |
| *Acinetobacter baumannii* (V4) | | | | | | | | | | |
| *Acinetobacter lwoffii* (V10) | | L | L | | L | | | L | | NE |

TABLE 10

| Strain | G-block | Azithro-mycin | Erythro-mycin | Roxithro-mycin | Dirithro-mycin | Aztreo-nam | Ceftazi-dime | Imi-penem | Cipro-floxacin | Oxytetra-cycline |
|---|---|---|---|---|---|---|---|---|---|---|
| *Klebsiella pneumoniae* (IR25, India, V6) MDR | 0% | 128 | 512 | 1024 | 1024 | 512 | >1024 | <2 | 128 | 2 |
| | 2% | 64 | 512 | >1024 | 1024 | 256 | 1024 | 2 | 64 | 2 |
| | 6% | 32 | 256 | 1024 | 512 | 128 | >1024 | 2 | 64 | 2 |
| | 10% | 16 | 256 | >1024 | 256 | 64 | 1024 | 2 | 64 | 2 |
| *Klebsiella pneumoniae* (5712, Wales, V12) MDR | 0% | 16 | 512 | 256 | 128 | 4 | >16 | <2 | >8 | 1 |
| | 2% | 16 | 256 | 512 | 64 | 4 | 8 | <2 | >8 | 1 |
| | 6% | 16 | 256 | 512 | 64 | 4 | >16 | <2 | >8 | 1 |
| | 10% | 16 | 256 | 512 | 32 | 4 | >16 | <2 | >8 | 1 |

TABLE 10-continued

| | | | | | | | | | |
|---|---|---|---|---|---|---|---|---|---|
| *Klebsiella pneumoniae* (K3, India, V8) MDR | 0% | 16 | 128 | 512 | 256 | 512 | >1024 | 8 | 32 | 512 |
| | 2% | 8 | 128 | 256 | 128 | 256 | >1024 | 16 | 32 | 512 |
| | 6% | 16 | 128 | >1024 | 128 | 128 | >1024 | 16 | >1024 | 512 |
| | 10% | 16 | 128 | >1024 | 128 | 128 | >1024 | 8 | >1024 | 1024 |

| | | | | | | | | | |
|---|---|---|---|---|---|---|---|---|---|
| *Klebsiella pneumoniae* (V6) | | | | M | | M | | | | NE |
| *Klebsiella pneumoniae* (V12) | | NE | | | | NE | M | L | M | NE |
| *Klebsiella pneumoniae* (V8) | | NE | NE | M | | | M | NE | M | |

TABLE 11

| Strain | G-block | Azithro-mycin | Erythro-mycin | Roxithro-mycin | Dirithro-mycin | Aztreo-nam | Ceftazi-dime | Imi-penem | Cipro-floxacin | Oxytetra-cycline |
|---|---|---|---|---|---|---|---|---|---|---|
| *Escherichia coli* (5702, Wales, V11) MDR | 0% | 16 | 512 | 512 | 128 | 256 | >16 | <2 | >8 | 0.5 |
| | 2% | 16 | 256 | 128 | 64 | 256 | >16 | <2 | >8 | 0.5 |
| | 6% | 8 | 256 | 256 | 32 | 128 | >16 | <2 | >8 | 0.5 |
| | 10% | 16 | 256 | 512 | 64 | 64 | >16 | <2 | >8 | 0.25 |
| *Providencia stuartii* (IR57 India, V7) MDR | 0% | <2 | 32 | 64 | 8 | >1024 | >1024 | 16 | 128 | 128 |
| | 2% | <2 | 16 | 32 | 4 | >1024 | >1024 | 16 | 128 | 128 |
| | 6% | <2 | 16 | 32 | 4 | >1024 | >1024 | 16 | 128 | 128 |
| | 10% | <2 | 16 | 32 | 2 | >1024 | >1024 | 8 | 128 | 128 |

| | | | | | | | | | |
|---|---|---|---|---|---|---|---|---|---|
| *Escherichia coli* (V11) | | NE | | NE | | | M | L | M | |
| *Providencia stuartii* (V7) | | L | | | | M | M | | NE | NE |

TABLE 12

| Strain | G-block | Azithro-mycin | Erythro-mycin | Roxithro-mycin | Dirithro-mycin | Aztreo-nam | Ceftazi-dime | Imi-penem | Cipro-floxacin | Oxytetra-cycline |
|---|---|---|---|---|---|---|---|---|---|---|
| *Streptococcus oralis* (5610, V17) MDR | 0% | | 2 | 8 | 4 | | 8 | <0.03125 | 32 | <0.25 |
| | 2% | | 16 | 8 | 4 | | 4 | 16 | <0.0625 | <0.25 |
| | 6% | | 0.03125 | 0.03125 | <0.03125 | | 0.03125 | 1 | 2 | 0.5 |
| | 10% | | 0.0625 | 16 | 0.03125 | | 1 | <0.03125 | 2 | <0.25 |
| MRSA 1040s, U50 MDR | 0% | 512 | >1024 | >1024 | 1024 | 1024 | >16 | 0.0625 | 32 | 2 |
| | 2% | 256 | >1024 | 1024 | 512 | 1024 | 16 | 0.0625 | 32 | 2 |
| | 6% | 256 | 1024 | 512 | 512 | 512 | 8 | 0.03125 | >1024 | 1 |
| | 10% | 256 | 512 | 256 | 256 | 512 | 2 | <0.03125 | >1024 | 0.5 |

| | | | | | | | | | |
|---|---|---|---|---|---|---|---|---|---|
| *Streptococcus oralis* (5610, V17) | | ND | | | | ND | | NE | | |
| MRSA 1040s, U50 | | | | | | | | | M | |

The data presented in Tables 8 to 12 generally show that increasing concentrations of OligoCF-5/20 (0-10%) decreases MIC values for all antibiotics tested (azithromycin, erythromycin, roxithromycin, dirithromycin (macrolides) aztreonam (monobactam) ceftazidime (cephalosporin) imipenem (carbapenem), ciprofloxacin (quinolone) and oxytetracycline (tetracycline)) in one bacterial strain or another). Notably, Table 12 shows that OligoCF-5/20 reduces MIC values in Gram positive organisms (MRSA U50 and *Streptococcus oralis*). The effect is particularly pronounced with the MRSA strain tested. This highlights the general applicability of the use of alginate oligomers alongside antibiotics in the treatment of all MDR bacteria (whether Gram negative, Gram positive, or Gram test non-responsive) e.g. by overcoming the resistance of MDR bacteria to antibiotic treatments or enhancing the efficacy of those antibiotics.

The effect was most consistently observed across the antibiotics tested in the *Pseudomonas, Acinetobacter, Burkholderia* and MRSA species tested, and strains V1, V2, V23, V4 and V9 in particular. Interestingly, in this Example strains V23 and V9 showed five instances of NE (no effect) or M (MICs were above the maximum concentration of antibiotic used), however in Example 2, data shows that these five combinations of bacteria and antibiotic do in fact display reductions in MIC with increasing concentrations of OligoCF-5/20. This highlights the more specific applicability of the use of alginate oligomers alongside antibiotics in the treatment of MDR *Pseudomonas, Acinetobacter, Burkholderia* and MRSA, e.g. by overcoming the resistance these bacteria have to antibiotic treatments or enhancing the efficacy of those antibiotics against these bacteria in particular.

The effect is most consistently observed across the strains tested with the macrolides (azithromycin, erythromycin, roxithromycin, dirithromycin) and to a slightly lesser extent aztreonam, ceftazidime and ciprofloxacin. This highlights the more specific applicability of alginate oligomers to the treatment of bacteria in general, including MDR bacteria with macrolides (e.g. azithromycin, erythromycin, roxithromycin, dirithromycin) in particular, but also quinolones (e.g. ciprofloxacin), monobactams (e.g. aztreonam) and cephalosporins (e.g. ceftazidime), e.g. by overcoming the resistance in bacteria to these antibiotic treatments or by enhancing the efficacy of these antibiotics against these bacteria.

Also of significant note is the evidence provided in Table 11 that shows that OligoCF-5/20 can lower MIC values for a β-lactam (imipenem, a carbapenem) in MDR *Providencia stuartii*. β-lactam resistance in *Providencia* populations is rising and so alginate oligomers may represent a new approach to the treatment of *Providencia* infections

The invention claimed is:

1. A method of overcoming resistance to at least one antibiotic in a Gram negative, multidrug resistance (MDR) bacterium, said method comprising contacting said bacterium with an alginate oligomer having an average molecular weight of less than 30,000 Daltons together with the at least one antibiotic, wherein the resistance to at least one antibiotic is overcome or reduced, wherein the Gram negative MDR bacterium is initially resistant to at least three classes of antibiotics and wherein said initial resistance to at least three classes of antibiotics is seen in a bacterium that is not in a biofilm mode of growth.

2. The method of claim 1, said method comprising administering to a subject infected, suspected to be infected, or at risk of infection with a Gram negative MDR bacterium said alginate oligomer together with the at least one antibiotic to overcome resistance to the at least one antibiotic in said bacterium.

3. The method of claim 2 comprising separate, simultaneous or sequential administration of said alginate oligomer together with the at least one antibiotic to a subject infected, suspected to be infected, or at risk of infection, with a Gram negative MDR bacterium.

4. The method of claim 1, said method comprising contacting a site and/or said bacteria with said alginate oligomer together with the at least one antibiotic to which said bacteria are resistant.

5. The method of claim 1, wherein the bacterium is resistant to three or more classes of antibiotics selected from the group consisting of macrolides, β-lactams, tetracyclines, polypeptide antibiotics and quinolones.

6. The method of claim 5 wherein the bacterium is resistant to three or more antibiotics selected from the group consisting of azithromycin, clarithromycin, dirithromycin, erythromycin, troleandomycin, roxithromycin, spiramycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin.

7. The method of claim 1, wherein the bacterium is resistant to one or more antibiotics selected from the group consisting of ceftazidime, imipenem/cilastatin, meropenem, aztreonam, azithromycin, clarithromycin, dirithromycin, erythromycin, roxithromycin, spiramycin, oxytetracycline and ciprofloxacin.

8. The method of claim 1, wherein the bacterium is resistant to one or more antibiotics that is a conventional treatment for that bacterium.

9. The method of claim 1, wherein the bacterium is from the family Enterobacteriacee or is a non-fermenting Gram negative bacterium.

10. The method of claim 9, wherein the bacterium is selected from the genera consisting of *Pseudomonas, Acinetobacter, Stenotrophomonas, Burkholderia, Escherichia, Providencia* and *Klebsiella*.

11. The method of claim 1, wherein the bacterium is an MDR strain selected from the group consisting of *Pseudomonas aeruginosa, Klebsiella pneumoniae, Burkholderia cepacia, Providencia stuartii* or *Acinetobacter baumannii* that is resistant to one or more antibiotics selected from the group consisting of ciprofloxacin, meropenem, ceftazidime, aztreonam, azithromycin, clarithromycin, dirithromycin, erythromycin, roxithromycin, spiramycin, oxytetracycline and imipenem/cilastatin.

12. The method of claim 1, wherein the at least one antibiotic is selected from the group consisting of macrolides, β-lactams, tetracyclines, polypeptide antibiotics and quinolones.

13. The method of claim 12, wherein the at least one antibiotic is selected from the group consisting of azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin.

14. The method of claim 12, wherein the at least one antibiotic is a macrolide.

15. The method of claim 1, wherein the bacterium is *Burkholderia* sp.

16. The method of claim 15, wherein said *Burkholderia* sp. is selected from *Burkholderia cepacia, Burkholderia pseudomallei* and *Burkholderia mallei*.

17. The method of claim 15, wherein said at least one antibiotic is selected from the group consisting of azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin.

18. The method of claim 1, wherein the bacterium is a clinical strain or a clinical isolate.

19. The method of claim 1, wherein the alginate oligomer has an average molecular weight of less than 25,000 Daltons.

20. The method of claim 1, wherein the alginate oligomer has a number average degree of polymerization of 2 to 100.

21. The method of claim 1, wherein the alginate oligomer has up to 100 monomer residues.

22. The method of claim 1, wherein the alginate oligomer has at least 70% G residues.

23. The method of claim 22 wherein the alginate oligomer has at least 80% G residues.

24. The method of claim 22, wherein at least 80% of the G residues are arranged in G-blocks.

25. The method of claim 1, wherein the alginate oligomer has at least 70% M residues.

26. The method of claim 25 wherein the alginate oligomer has at least 80% M residues.

27. The method of claim 25, wherein at least 80% of the M residues are arranged in M blocks.

28. The method of claim 2, wherein the infection is of an internal or external body surface selected from the group consisting of a surface in the oral cavity, the reproductive tract, the urinary tract, the respiratory tract, the gastrointestinal tract, the peritoneum, the middle ear, the prostate, vascular intima, the eye, including the conjunctiva or corneal tissue, lung tissue, heart valves, skin, scalp, nails, the interior of wounds or the surface of adrenal, hepatic, renal, pancreatic, pituitary, thyroid, immune, ovarian, testicular, prostate, endometrial, ocular, mammary, adipose, epithelial, endothelial, neural, muscle, pulmonary, epidermis or osseous tissue; or in a body fluid selected from blood, plasma, serum, cerebrospinal fluid, GI tract contents, sputum, pulmonary secretions and semen; or in or on body tissue selected from adrenal, hepatic, renal, pancreatic, pituitary, thyroid, immune, ovarian, testicular, prostate, endometrial, ocular, mammary, adipose, epithelial, endothelial, neural, muscle, pulmonary, epidermis and osseous tissue.

29. The method of claim 2, wherein the subject is selected from the group consisting of a subject with a pre-established infection, an immunocompromised subject, a subject undergoing intensive or critical care, a subject suffering from trauma, a subject with a burn, a subject with an acute and/or chronic wound, a neonatal subject, an elderly subject, a subject with cancer, a subject suffering from an auto-immune condition, a subject with reduced or abrogated epithelial or endothelial secretion and/or secretion clearance and a subject fitted with a medical device.

30. The method of claim 29, wherein the subject is selected from the group consisting of a subject with a condition selected from HIV, sepsis, septic shock, AIDS, a cancer of the immune system, rheumatoid arthritis, diabetes mellitus type I, Crohn's disease, COPD, COAD, COAP, bronchitis, cystic fibrosis, emphysema, lung cancer, asthma, pneumonia and sinusitis, a subject preparing for, undergoing, or recovering from chemotherapy and/or radiotherapy, an organ transplant subject and a subject resident in a healthcare institution or a smoker.

31. The method of claim 29, wherein the subject is selected from the group consisting of a subject with a respiratory condition or disease.

32. The method of claim 1, wherein said bacterium is on an animate or inanimate surface or in an animate or inanimate material.

33. The method of claim 1, wherein the bacterium is on a surface selected from the group consisting of surfaces of food or drink processing, preparation, storage or dispensing machinery or equipment, surfaces of air conditioning apparatus, surfaces of industrial machinery, surfaces of storage tanks, surfaces of medical or surgical equipment, surfaces of aquatic/marine equipment or the surfaces of buildings and other structures.

34. The method of claim 33 wherein the surface is selected from the group consisting of food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls, dental waterlines, oil drilling conduits, contact lenses, contact lens storage cases, catheters, prosthetic devices and implantable medical devices.

35. The method of claim 1, wherein the bacterium is in a material selected from the group consisting of clinical/scientific waste, animal or human food stuffs, personal hygiene products, cosmetics, drinking water supplies, waste water supplies, agricultural feedstuffs and water supplies, insecticide formulations, pesticide formulations, herbicide formulations, industrial lubricants, cell and tissue culture media, and cell and tissue cultures.

36. The method of claim 10, wherein the bacterium is one of *Pseudomonas aeruginosa, Acinetobacter baumannii, Stenotrophomonas maltophilia, Burkholderia* spp, *E. coli, Providencia stuartii* and *Klebsiella pneumoniae*.

37. The method of claim 20, wherein the alginate oligomer has a number average degree of polymerization of 2 to 35.

38. The method of claim 21, wherein the alginate oligomer is a 2- to 35-mer.

39. The method of claim 31, wherein the respiratory condition or disease is selected from the group consisting of COPD, COAD, COAP, bronchitis, cystic fibrosis, emphysema, lung cancer, asthma, and pneumonia.

40. The method of claim 1, wherein the alginate oligomer has at least 85% G residues.

41. The method of claim 1, wherein the alginate oligomer has at least 90% G residues.

* * * * *